US008426367B2

(12) United States Patent
Patterson et al.

(10) Patent No.: US 8,426,367 B2
(45) Date of Patent: Apr. 23, 2013

(54) PEPTIDES SPECIFIC FOR HUMAN BLOOD OUTGROWTH ENDOTHELIAL CELLS

(75) Inventors: Cam Patterson, Chapel Hill, NC (US); Anka Veleva, Cary, NC (US); Stuart Cooper, Powell, OH (US)

(73) Assignees: The University of North Carolina at Chapel Hill, Chapel Hill, NC (US); North Carolina State University, Raleigh, NC (US); The Ohio State University Research Foundation, Columbus, OH (US)

( * ) Notice: Subject to any disclaimer, the term of this patent is extended or adjusted under 35 U.S.C. 154(b) by 572 days.

(21) Appl. No.: 12/530,137

(22) PCT Filed: Mar. 5, 2008

(86) PCT No.: PCT/US2008/055874
§ 371 (c)(1),
(2), (4) Date: Mar. 16, 2010

(87) PCT Pub. No.: WO2008/109653
PCT Pub. Date: Sep. 12, 2008

(65) Prior Publication Data
US 2010/0190703 A1     Jul. 29, 2010

Related U.S. Application Data

(60) Provisional application No. 60/892,987, filed on Mar. 5, 2007.

(51) Int. Cl.
*A61K 38/10*     (2006.01)
*A61K 38/06*     (2006.01)
*A61K 38/16*     (2006.01)
*A61K 38/04*     (2006.01)
*A61K 38/00*     (2006.01)
*A61F 13/00*     (2006.01)
*C12N 5/071*     (2010.01)

(52) U.S. Cl.
USPC ....... 514/21.5; 514/21.6; 514/21.4; 514/21.3; 424/422; 435/372; 435/810; 530/327; 530/326; 530/325; 530/324

(58) Field of Classification Search .................. None
See application file for complete search history.

(56) References Cited

U.S. PATENT DOCUMENTS 5,679,339 A    10/1997   Keith et al.
7,261,881 B1    8/2007   Sierra-Honigmann
2009/0076481 A1    3/2009   Stegmann et al.

FOREIGN PATENT DOCUMENTS

WO   WO 2005/078073 A   8/2005
WO   WO 2006/086822 A1   8/2006

OTHER PUBLICATIONS

Veleva et al. 2007. Biotech. Bioeng. 98:306-312.*
Bowie, J., et al., "Deciphering the Message in Protein Sequences: Tolerance to Amino Acid Subsitutions," *Science*, 1990, vol. 247(4948), pp. 1306-1310.
Feinglass, S., et al., "Treatment of Lupus-Induced Thrombocytopenia with Recombinant Human Interleukin-11," *Arthritis & Rheumatism*, 2001, vol. 44(1), pp. 170-175.
Gordon, M., et al., "A Phase I Trial of Recombinant Human Interleukin-11 (Neumega rhIL-11 Growth Factor) in Women With Breast Cancer Receiving Chemotherapy," *Blood*, 1996, vol. 87(9), pp. 3615-3624.
Isaacs, C., et al., "Randomized placebo-controlled study of recombinant human interleukin-11 to prevent chemotherapy-induced thrombocytopenia in patients with breast cancer receiving dose-intensive cyclophosphamide and doxorubicin," *Journal of Clinical Oncology*, 1997, vol. 15(11), pp. 3368-3377.
Ngo, J., et al., Chapter 14 "Computational Complexity, Protein Structure Prediction, and Levinthal Paradox," *The Protein Folding Problem and Tertiary Structure Prediction*, 1994, Merz, et al., eds, Birkhäuser Boston, pp. 433-506.
Tepler, I., et al., "A Randomized Placebo-Controlled Trial of Recombinant Human Interleukin-11 in Cancer Patients With Severe Thrombocytopenia Due to Chemotherapy," *Blood*, 1996, vol. 87(9), pp. 3607-3614.
Veleva, A. et al., "Selective endothelial cell attachment to peptide-modified terpolymers," *Biomaterials*, 2008, vol. 29, pp. 3656-3661.
Wang, D., et al., "A Single Amino Acid Determines Lysophospholipid Specificity of the S1P$_1$ (EDG1) and LPA$_1$ (EDG2) Phospholipid Growth Factor Receptors," *The Journal of Biological Chemistry*, 2001, vol. 276(52), pp. 49213-49220.
Wells, James A., "Additivity of Mutational Effects in Proteins," *Perspective in Biochemistry*, 1990, vol. 29(37), pp. 8509-8517.
Balestrieri et al., "Novel Challenges in Exploring Peptide Ligands and Corresponding Tissue-specific Endothelial Receptors," *European Journal of Cancer*, May 1, 2007, pp. 1242-1250, vol. 43, No. 8.

(Continued)

*Primary Examiner* — Shulamith H Shafer
(74) *Attorney, Agent, or Firm* — Alston & Bird LLP

(57) ABSTRACT

Provided herein are compositions and methods for binding outgrowth endothelial cells (OEC). The compositions consist of peptide ligands capable of binding OEC with high affinity and specificity. The compositions of the invention include peptides set forth in SEQ ID NO: 1-38 and variants and derivatives thereof. Compositions also include the nucleotide sequences encoding the peptides of the invention. The compositions find use in methods for the isolation of OEC and for the recruitment and retention of OEC to sites of therapeutic interest. Methods for the identification and isolation of other peptides capable of binding OEC are also provided.

30 Claims, 12 Drawing Sheets

OTHER PUBLICATIONS

Bussolati, B., et al., "Targeting of Human Renal Tumor-derived Endothelial Cells with Peptides Obtained by Phage Display," *Journal of Molecular Medicine*, Aug. 2007, pp. 897-906, vol. 85, No. 8.

Eggermann, J., et al., "Endothelial Progenitor Cell Culture and Differentiation in Vitro: A Methodological Comparison Using Human Umbilical Cord Blood," *Cardiovascular Research*, May 1, 2003, pp. 478-486, vol. 58, No. 2.

Hardy, et al., "Angiogenesis Induced by Novel Peptides Selected from a Phage Display Library by Screening Human Vascular Endothelial Cells Under Different Physiological Conditions," *Peptides*, Feb. 7, 2007, pp. 691-701, vol. 28, No. 3.

Hajitou et al., "Vascular Targeting: Recent Advances and Therapeutic Perspectives," *Trends in Cardiovascular Medicine*, Apr. 1, 2006, pp. 80-88, vol. 16, No. 3.

Kim et al., "RGD-peptide Presents Anti-adhesive Effect, but not Direct Pro-apoptotic Effect on Endothelial Progenitor Cells," *Archives of Biochemistry and Biophysics*, Feb. 24, 2007, pp. 40-49, vol. 459, No. 1.

Liang Shuhui et al., "Screening and Identification of Vascular-endothelial-cell-specific Binding Peptide in Gastric Cancer," *Journal of Molecular Medicine*, Sep. 2006, pp. 764-773, vol. 84, No. 9.

Lin, Y., et al., "Origins of Circulating Endothelial Cells and Endothelial Outgrowth from Blood," *Journal of Clinical Investigation*, Jan. 1, 2000, pp. 71-77, vol. 105, No. 1.

Schluesener, H.J., et al., "Selection of Recombinant Phages Binding to Pathological Endothelial and Tumor Cells of Rat Glioblastoma by In-vivo Display," *Journal of Neurological Sciences*, Sep. 15, 2004, pp. 77-82, vol. 224, No. 1-2.

Veleva, A.N., et al., "Selection and Initial Characterization of Novel Peptide Ligands that Bind Specifically to Human Blood Outgrowth Endothelial Cells," *Biotechnology and Bioengineering*, Sep. 1, 2007, pp. 306-312, vol. 98, No. 1.

\* cited by examiner

SEQUENCE LISTING

```
<160> NUMBER OF SEQ ID NOS: 47

<210> SEQ ID NO 1
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 1

His Pro Ala Ile Val His Ile Ser Pro Gln Trp Ala
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 2

Gln Met Val Tyr Gly Pro Leu Arg Ser Thr Glu Gln
 1               5                  10

<210> SEQ ID NO 3
<211> LENGTH: 12
<212> TYPE: PRT
<213> ORGANISM: Artificial Sequence
<220> FEATURE:
```

```
<223> OTHER INFORMATION: Human outgrowth endothelial cell-binding
      peptides isolated from phage library

<400> SEQUENCE: 3

Asn Ser Leu Thr Ser Glu Pro Leu Arg Tyr Gly Gly
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 4

Ala Pro Phe Ala His Ser Gly Pro Leu Ala Phe Ser
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 5

Thr Pro Leu His Pro Lys Ser Leu Met Val Trp His
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 6

Ser Asn Ser Met His Leu Met Thr Met Thr Gly Leu
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 7

Ser Val Pro Pro Arg Tyr Thr Leu Thr Leu Gln Trp
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 8

Thr Leu Asp Trp Thr Lys Pro Pro Leu Arg Ser Gly
1               5                   10

<210> SEQ ID NO 9
```

```
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 9

Ala Ser Gln Gly Tyr Pro Glu His Arg His Ala Ser
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 10

His Lys Ser Tyr Leu Pro Val Pro Ser Leu Tyr Gly
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 11

Gln Thr Thr Lys Leu His Ile Met Asp Thr Gly Phe
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 12

Ile Ser Pro Ala Pro His Leu Leu Thr Ser Arg Phe
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 13

His Gly Thr Asn Gln Ala Leu Ser Leu Leu Thr Pro
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 14

Val Leu Asn Pro Gln Thr Thr Val Met Pro Pro Leu
```

<210> SEQ ID NO 15
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 15

Ala Thr Thr Ser Leu Thr Pro Thr Met Ala Asn His
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 16

Gln Ala Thr Gly Pro Thr Thr Pro Thr Thr Ser Gly
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 17

Thr Pro Ser Leu Glu Gln Arg Thr Val Tyr Ala Lys
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 18

Leu Tyr Ser Ala Ser Thr Pro Pro Asp Pro Gly Gly
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 19

Phe Pro Met Ser Ser Tyr Lys Thr Tyr Ala Thr Pro
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

```
<400> SEQUENCE: 20

Ile Asn Thr Pro Ala Asn Arg Asn Pro Val Leu Gly
 1               5                  10

<210> SEQ ID NO 21
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 21

Trp Asp Thr Asn Arg Asn Ala Ala Ser Thr Pro Gly
 1               5                  10

<210> SEQ ID NO 22
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 22

Ser Tyr Gln Thr Leu Lys Gln His Leu Pro Tyr Gly
 1               5                  10

<210> SEQ ID NO 23
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 23

His His Val Asp Ser Leu Pro Thr Leu Asp Trp Lys
 1               5                  10

<210> SEQ ID NO 24
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 24

Lys Leu Pro His Gln Pro Pro Ser Ala Ala Val His
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 25

Ser Pro Trp Thr Ser Phe Leu Gln Trp Ala Arg Gly
 1               5                  10

<210> SEQ ID NO 26
<211> LENGTH: 12
<212> TYPE: PRT
```

```
<213> ORGANISM: Artificial Sequence
<220> FEATURE:
<223> OTHER INFORMATION: Human outgrowth endothelial cell-binding
      peptides isolated from phage library

<400> SEQUENCE: 26

Gln Phe Pro Pro Lys Leu Thr Asn Asn Ser Met Leu
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 27

Tyr Thr Asp Asn Ser Leu Gly Thr Ser Val Gly Lys
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 28

Thr Ser Leu Arg Glu Leu Pro Ala Glu Trp Ser Arg
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 29

Ser His Gly Lys Pro Pro Ser Arg Ser Pro Trp Thr
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 30

Tyr Asn Leu Gly Gln Leu Glu Ala Gln Ile Thr Ser
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 31

Ile Thr Leu Ser Ala Thr Lys Gly Ala Ala Pro Ser
1               5                   10
```

```
<210> SEQ ID NO 32
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 32

Ser Pro Pro Pro Ser Asn Ala Gly Ser His His Val
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 33

Thr His Pro Pro Asn Pro Ser Val Ser Ile Gly Gly
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 34

Met Pro Thr Ser Ser Thr Ala Pro Pro Pro Leu Ile
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 35

Ala Asn Tyr Phe Ser Ser Pro Ile Lys His Ala Thr
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 36

His Pro Pro His Asn Met His Leu Pro Ala Phe Ser
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 37
```

```
Met Pro Thr Leu Thr Arg Ala Pro His Thr Ala Cys
1               5                   10
```

<210> SEQ ID NO 38
<211> LENGTH: 12
<212> TYPE: PRT
<213> ORGANISM: Artificial Sequence
<220> FEATURE:
<223> OTHER INFORMATION: Human outgrowth endothelial cell-binding
      peptides isolated from phage library

<400> SEQUENCE: 38

```
Leu Pro Arg Lys Thr Pro Asp Tyr Leu Gln Thr Arg
1               5                   10
```

<210> SEQ ID NO 39
<211> LENGTH: 12
<212> TYPE: PRT
<213> ORGANISM: Artificial Sequence
<220> FEATURE:
<223> OTHER INFORMATION: Consensus sequence for Human outgrowth
      endothelial cell-binding peptides isolated from phage library
<220> FEATURE:
<221> NAME/KEY: VARIANT
<222> LOCATION: 6
<223> OTHER INFORMATION: Xaa = Pro or Leu

<400> SEQUENCE: 39

```
Ser Pro Thr Pro Ser Xaa Pro Pro Ser Ala Gly Gly
1               5                   10
```

<210> SEQ ID NO 40
<211> LENGTH: 1569
<212> TYPE: PRT
<213> ORGANISM: Homo sapiens

<400> SEQUENCE: 40

```
Met Val Gln Arg Trp Leu Leu Leu Ser Cys Cys Gly Ala Leu Leu Ser
1               5                   10                  15

Ala Gly Leu Ala Asn Thr Ser Tyr Thr Ser Pro Gly Leu Gln Arg Leu
            20                  25                  30

Lys Asp Ser Pro Gln Thr Ala Pro Asp Lys Gly Gln Cys Ser Thr Trp
        35                  40                  45

Gly Ala Gly His Phe Ser Thr Phe Asp His His Val Tyr Asp Phe Ser
    50                  55                  60

Gly Thr Cys Asn Tyr Ile Phe Ala Ala Thr Cys Lys Asp Ala Phe Pro
65                  70                  75                  80

Ser Phe Ser Val Gln Leu Arg Arg Gly Pro Asp Gly Ser Ile Ser Arg
                85                  90                  95

Ile Ile Val Glu Leu Gly Ala Ser Val Val Thr Val Ser Glu Ala Ile
            100                 105                 110

Ile Ser Val Lys Asp Ile Gly Val Ile Ser Leu Pro Tyr Thr Ser Asn
        115                 120                 125

Gly Leu Gln Ile Thr Pro Phe Gly Gln Ser Val Arg Leu Val Ala Lys
    130                 135                 140

Gln Leu Glu Leu Glu Leu Glu Val Val Trp Gly Pro Asp Ser His Leu
145                 150                 155                 160

Met Val Leu Val Glu Arg Lys Tyr Met Gly Gln Met Cys Gly Leu Cys
                165                 170                 175

Gly Asn Phe Asp Gly Lys Val Thr Asn Glu Phe Val Ser Glu Glu Gly
            180                 185                 190
```

-continued

```
Lys Phe Leu Glu Pro His Lys Phe Ala Ala Leu Gln Lys Leu Asp Asp
        195                 200                 205

Pro Gly Glu Ile Cys Thr Phe Gln Asp Ile Pro Ser Thr His Val Arg
    210                 215                 220

Gln Ala Gln His Ala Arg Gly Cys Thr Gln Leu Leu Thr Leu Val Ala
225                 230                 235                 240

Pro Glu Cys Ser Val Ser Lys Glu Pro Phe Val Leu Ser Cys Gln Ala
                245                 250                 255

Asp Val Ala Ala Pro Gln Pro Gly Pro Gln Asn Ser Ser Tyr Ala
                260                 265                 270

Thr Leu Ser Glu Tyr Ser Arg Gln Cys Ser Met Val Gly Gln Pro Val
        275                 280                 285

Ala Leu Arg Ser Pro Gly Leu Cys Ser Val Gly Gln Cys Pro Ala Asn
    290                 295                 300

Gln Val Tyr Gln Glu Cys Gly Ser Ala Cys Val Lys Thr Cys Ser Asn
305                 310                 315                 320

Ser Glu His Ser Cys Ser Ser Cys Thr Phe Gly Cys Phe Cys Pro
                325                 330                 335

Glu Gly Thr Asp Leu Asn Asp Leu Ser Asn Asn His Thr Cys Val Pro
        340                 345                 350

Val Thr Gln Cys Pro Cys Val Leu His Gly Ala Met Tyr Ala Pro Gly
    355                 360                 365

Glu Val Thr Ile Ala Ala Cys Gln Thr Cys Arg Cys Thr Leu Gly Arg
370                 375                 380

Trp Val Cys Thr Glu Arg Pro Cys Pro Gly His Cys Ser Leu Glu Gly
385                 390                 395                 400

Gly Ser Phe Val Thr Thr Phe Asp Ala Arg Pro Tyr Arg Phe His Gly
                405                 410                 415

Thr Cys Thr Tyr Ile Leu Leu Gln Ser Pro Gln Leu Pro Glu Asp Gly
        420                 425                 430

Ala Leu Met Ala Val Tyr Asp Lys Ser Gly Val Ser His Ser Glu Thr
    435                 440                 445

Ser Leu Val Ala Val Val Tyr Leu Ser Arg Gln Asp Lys Ile Val Ile
450                 455                 460

Ser Gln Asp Glu Val Val Thr Asn Asn Gly Glu Ala Lys Trp Leu Pro
465                 470                 475                 480

Tyr Lys Thr Arg Asn Ile Thr Val Phe Arg Gln Thr Ser Thr His Leu
                485                 490                 495

Gln Met Ala Thr Ser Phe Gly Leu Glu Leu Val Val Gln Leu Arg Pro
        500                 505                 510

Ile Phe Gln Ala Tyr Val Thr Val Gly Pro Gln Phe Arg Gly Gln Thr
    515                 520                 525

Arg Gly Leu Cys Gly Asn Phe Asn Gly Asp Thr Thr Asp Asp Phe Thr
530                 535                 540

Thr Ser Met Gly Ile Ala Glu Gly Thr Ala Ser Leu Phe Val Asp Ser
545                 550                 555                 560

Trp Arg Ala Gly Asn Cys Pro Asp Ala Leu Glu Arg Glu Thr Asp Pro
                565                 570                 575

Cys Ser Met Ser Gln Leu Asn Lys Val Cys Ala Glu Thr His Cys Ser
        580                 585                 590

Met Leu Leu Arg Thr Gly Thr Val Phe Glu Arg Cys His Ala Thr Val
    595                 600                 605

Asn Pro Ala Pro Ile Tyr Lys Arg Cys Met Tyr Gln Ala Cys Asn Tyr
610                 615                 620
```

-continued

```
Glu Glu Thr Phe Pro His Ile Cys Ala Ala Leu Gly Asp Tyr Val His
625                 630                 635                 640

Ala Cys Ser Leu Arg Gly Val Leu Leu Trp Gly Trp Arg Ser Ser Val
            645                 650                 655

Asp Asn Cys Thr Ile Pro Cys Thr Gly Asn Thr Thr Phe Ser Tyr Asn
            660                 665                 670

Ser Gln Ala Cys Glu Arg Thr Cys Leu Ser Leu Ser Asp Arg Ala Thr
        675                 680                 685

Glu Cys His His Ser Ala Val Pro Val Asp Gly Cys Asn Cys Pro Asp
    690                 695                 700

Gly Thr Tyr Leu Asn Gln Lys Gly Glu Cys Val Arg Lys Ala Gln Cys
705                 710                 715                 720

Pro Cys Ile Leu Glu Gly Tyr Lys Phe Ile Leu Ala Glu Gln Ser Thr
            725                 730                 735

Val Ile Asn Gly Ile Thr Cys His Cys Ile Asn Gly Arg Leu Ser Cys
            740                 745                 750

Pro Gln Arg Leu Gln Met Phe Leu Ala Ser Cys Gln Ala Pro Lys Thr
        755                 760                 765

Phe Lys Ser Cys Ser Gln Ser Ser Glu Asn Lys Phe Gly Ala Ala Cys
    770                 775                 780

Ala Pro Thr Cys Gln Met Leu Ala Thr Gly Val Ala Cys Val Pro Thr
785                 790                 795                 800

Lys Cys Glu Pro Gly Cys Val Cys Ala Glu Gly Leu Tyr Glu Asn Ala
            805                 810                 815

Tyr Gly Gln Cys Val Pro Pro Glu Glu Cys Pro Cys Glu Phe Ser Gly
            820                 825                 830

Val Ser Tyr Pro Gly Gly Ala Glu Leu His Thr Asp Cys Arg Thr Cys
        835                 840                 845

Ser Cys Ser Arg Gly Arg Trp Ala Cys Gln Gln Gly Thr His Cys Pro
    850                 855                 860

Ser Thr Cys Thr Leu Tyr Gly Glu Gly His Val Ile Thr Phe Asp Gly
865                 870                 875                 880

Gln Arg Phe Val Phe Asp Gly Asn Cys Glu Tyr Ile Leu Ala Thr Asp
            885                 890                 895

Val Cys Gly Val Asn Tyr Ser Gln Pro Thr Phe Lys Ile Leu Thr Glu
            900                 905                 910

Asn Val Ile Cys Gly Asn Ser Gly Val Thr Cys Ser Arg Ala Ile Lys
        915                 920                 925

Ile Phe Leu Gly Gly Leu Ser Val Val Leu Ala Asp Arg Asn Tyr Thr
    930                 935                 940

Val Thr Gly Glu Glu Pro His Val Gln Leu Gly Val Thr Pro Gly Ala
945                 950                 955                 960

Leu Ser Leu Val Val Asp Ile Ser Ile Pro Gly Arg Tyr Asn Leu Thr
            965                 970                 975

Leu Ile Trp Asn Arg His Met Thr Ile Leu Ile Arg Ile Ala Arg Ala
            980                 985                 990

Ser Gln Asp Pro Leu Cys Gly Leu Cys Gly Asn Phe Asn Gly Asn Met
        995                 1000                1005

Lys Asp Asp Phe Glu Thr Arg Ser Arg Tyr Val Ala Ser Ser Glu Leu
    1010                1015                1020

Glu Leu Val Asn Ser Trp Lys Glu Ser Pro Leu Cys Gly Asp Val Ser
1025                1030                1035                1040

Phe Val Thr Asp Pro Cys Ser Leu Asn Ala Phe Arg Arg Ser Trp Ala
```

-continued

```
                1045                1050                1055
Glu Arg Lys Cys Ser Val Ile Asn Ser Gln Thr Phe Ala Thr Cys His
            1060                1065                1070
Ser Lys Val Tyr His Leu Pro Tyr Tyr Glu Ala Cys Val Arg Asp Ala
            1075                1080                1085
Cys Gly Cys Asp Ser Gly Gly Asp Cys Glu Cys Leu Cys Asp Ala Val
            1090                1095                1100
Ala Ala Tyr Ala Gln Ala Cys Leu Asp Lys Gly Val Cys Val Asp Trp
1105                1110                1115                1120
Arg Thr Pro Ala Phe Cys Pro Ile Tyr Cys Gly Phe Tyr Asn Thr His
                1125                1130                1135
Thr Gln Asp Gly His Gly Glu Tyr Gln Tyr Thr Gln Glu Ala Asn Cys
            1140                1145                1150
Thr Trp His Tyr Gln Pro Cys Leu Cys Pro Ser Gln Pro Gln Ser Val
            1155                1160                1165
Pro Gly Ser Asn Ile Glu Gly Cys Tyr Asn Cys Ser Gln Asp Glu Tyr
            1170                1175                1180
Phe Asp His Glu Glu Gly Val Cys Val Pro Cys Met Pro Pro Thr Thr
1185                1190                1195                1200
Pro Gln Pro Pro Thr Thr Pro Gln Leu Pro Thr Thr Gly Ser Arg Pro
                1205                1210                1215
Thr Gln Val Trp Pro Met Thr Gly Thr Ser Thr Thr Ile Gly Leu Leu
            1220                1225                1230
Ser Ser Thr Gly Pro Ser Pro Ser Ser Asn His Thr Pro Ala Ser Pro
            1235                1240                1245
Thr Gln Thr Pro Leu Leu Pro Ala Thr Leu Thr Ser Ser Lys Pro Thr
            1250                1255                1260
Ala Ser Ser Gly Glu Pro Pro Arg Pro Thr Thr Ala Val Thr Pro Gln
1265                1270                1275                1280
Ala Thr Ser Gly Leu Pro Pro Thr Ala Thr Leu Arg Ser Thr Ala Thr
                1285                1290                1295
Lys Pro Thr Val Thr Gln Ala Thr Thr Arg Ala Thr Ala Ser Thr Ala
                1300                1305                1310
Ser Pro Ala Thr Thr Ser Thr Ala Gln Ser Thr Arg Thr Thr Met
            1315                1320                1325
Thr Leu Pro Thr Pro Ala Thr Ser Gly Thr Ser Pro Thr Leu Pro Lys
            1330                1335                1340
Ser Thr Asn Gln Glu Leu Pro Gly Thr Thr Ala Thr Gln Thr Thr Gly
1345                1350                1355                1360
Pro Arg Pro Thr Pro Ala Ser Thr Thr Gly Pro Thr Thr Pro Gln Pro
                1365                1370                1375
Gly Gln Pro Thr Arg Pro Thr Ala Thr Glu Thr Thr Gln Thr Arg Thr
                1380                1385                1390
Thr Thr Glu Tyr Thr Thr Pro Gln Thr Pro His Thr Thr His Ser Pro
                1395                1400                1405
Pro Thr Ala Gly Ser Pro Val Pro Ser Thr Gly Pro Val Thr Ala Thr
            1410                1415                1420
Ser Phe His Ala Thr Thr Thr Tyr Pro Thr Pro Ser His Pro Glu Thr
1425                1430                1435                1440
Thr Leu Pro Thr His Val Pro Pro Phe Ser Thr Ser Leu Val Thr Pro
                1445                1450                1455
Ser Thr His Thr Val Ile Thr Pro Thr His Ala Gln Met Ala Ser Ser
                1460                1465                1470
```

```
Ala Ser Asn His Ser Ala Pro Thr Gly Thr Ile Pro Pro Pro Thr Thr
        1475                1480                1485

Leu Lys Ala Thr Gly Ser Thr His Thr Ala Pro Pro Ile Thr Pro Thr
    1490                1495                1500

Thr Ser Gly Thr Ser Gln Ala His Ser Ser Phe Ser Thr Asn Lys Thr
1505                1510                1515                1520

Pro Thr Ser Leu His Ser His Thr Ser Ser Thr His His Pro Glu Val
            1525                1530                1535

Thr Pro Thr Ser Thr Thr Ser Ile Thr Pro Asn Pro Thr Ser Thr Arg
                1540                1545                1550

Thr Arg Thr Pro Met Ala His Thr Asn Ser Ala Thr Ser Ser Arg Pro
            1555                1560                1565

Pro

<210> SEQ ID NO 41
<211> LENGTH: 217
<212> TYPE: PRT
<213> ORGANISM: Homo sapiens

<400> SEQUENCE: 41

Met Ala Lys Ala Tyr Pro Gln Tyr Tyr Arg Lys Pro Ser Val Val Lys
1               5                   10                  15

Arg Met Pro Ala Met Leu Thr Gly Leu Cys Gln Gly Cys Gly Thr Arg
            20                  25                  30

Gln Val Val Phe Thr Ser Asp Pro His Lys Ser Tyr Leu Pro Val Gln
        35                  40                  45

Phe Gln Ser Pro Asp Lys Ala Glu Thr Gln Arg Gly Asp Pro Ser Val
    50                  55                  60

Ile Ser Val Asn Gly Thr Asp Phe Thr Phe Arg Ser Ala Gly Val Leu
65                  70                  75                  80

Leu Leu Val Val Asp Pro Cys Ser Val Pro Phe Arg Leu Thr Glu Lys
                85                  90                  95

Thr Val Phe Pro Leu Ala Asp Val Ser Arg Ile Glu Glu Tyr Leu Lys
            100                 105                 110

Thr Gly Ile Pro Pro Arg Ser Ile Val Leu Leu Ser Thr Arg Gly Glu
        115                 120                 125

Ile Lys Gln Leu Asn Ile Ser His Leu Leu Val Pro Leu Gly Leu Ala
    130                 135                 140

Lys Pro Ala His Leu Tyr Asp Lys Gly Ser Thr Ile Phe Leu Gly Phe
145                 150                 155                 160

Ser Gly Asn Phe Lys Pro Ser Trp Thr Lys Leu Phe Thr Ser Pro Ala
                165                 170                 175

Gly Gln Gly Leu Gly Val Leu Glu Gln Phe Ile Pro Leu Gln Leu Asp
            180                 185                 190

Glu Tyr Gly Cys Pro Arg Ala Thr Thr Val Arg Arg Arg Asp Leu Glu
        195                 200                 205

Leu Leu Lys Gln Ala Ser Lys Ala His
    210                 215

<210> SEQ ID NO 42
<211> LENGTH: 389
<212> TYPE: PRT
<213> ORGANISM: Homo sapiens

<400> SEQUENCE: 42

Met Glu Phe Pro Leu Ala Gln Ile Cys Pro Gln Gly Ser His Glu Ala
1               5                   10                  15
```

Pro Ile Pro Thr Phe Ser Thr Phe Gln Ile Thr Asp Met Thr Arg Arg
            20                  25                  30

Ser Cys Gln Asn Leu Gly Tyr Thr Ala Gly Ile Ser Gln Ala Pro Glu
        35                  40                  45

Ala Ala Ser Ser Thr Gly Asn Ala Glu Arg Ala Glu Val Pro Gly
    50                  55                  60

Glu Gly Ser Leu Phe Leu Gln Ala Glu Thr Arg Ala Trp Phe Gln Lys
65                  70                  75                  80

Thr Gln Ala His Trp Leu Leu Gln His Gly Ala Ala Pro Ala Trp Phe
                85                  90                  95

His Gly Phe Ile Thr Arg Arg Glu Ala Glu Arg Leu Leu Glu Pro Lys
                100                 105                 110

Pro Gln Gly Cys Tyr Leu Val Arg Phe Ser Glu Ser Ala Val Thr Phe
            115                 120                 125

Val Leu Thr Tyr Arg Ser Arg Thr Cys Cys Arg His Phe Leu Leu Ala
        130                 135                 140

Gln Leu Arg Asp Gly Arg His Val Val Leu Gly Glu Asp Ser Ala His
145                 150                 155                 160

Ala Arg Leu Gln Asp Leu Leu Leu His Tyr Thr Ala His Pro Leu Ser
                165                 170                 175

Pro Tyr Gly Glu Thr Leu Thr Glu Pro Leu Ala Arg Gln Thr Pro Glu
            180                 185                 190

Pro Ala Gly Leu Ser Leu Arg Thr Glu Glu Ser Asn Phe Gly Ser Lys
        195                 200                 205

Ser Gln Asp Pro Asn Pro Gln Tyr Ser Pro Ile Ile Lys Gln Gly Gln
210                 215                 220

Ala Pro Val Pro Met Gln Lys Glu Gly Ala Gly Glu Lys Glu Pro Ser
225                 230                 235                 240

Gln Leu Leu Arg Pro Lys Pro Ile Pro Ala Lys Pro Gln Leu Pro
                245                 250                 255

Pro Glu Val Tyr Thr Ile Pro Val Pro Arg His Arg Pro Ala Pro Arg
            260                 265                 270

Pro Lys Pro Ser Asn Pro Ile Tyr Asn Glu Pro Asp Glu Pro Ile Ala
        275                 280                 285

Phe Tyr Ala Met Gly Arg Gly Ser Pro Gly Ala Pro Ser Asn Ile
        290                 295                 300

Tyr Val Glu Val Glu Asp Glu Gly Leu Pro Ala Thr Leu Gly His Pro
305                 310                 315                 320

Val Leu Arg Lys Ser Trp Ser Arg Pro Val Pro Gly Gly Gln Asn Thr
                325                 330                 335

Gly Gly Ser Gln Leu His Ser Glu Asn Ser Val Ile Gly Gln Gly Pro
            340                 345                 350

Pro Leu Pro His Gln Pro Pro Ala Trp Arg His Thr Leu Pro His
        355                 360                 365

Asn Leu Ser Arg Gln Val Leu Gln Asp Arg Gly Gln Ala Trp Leu Pro
        370                 375                 380

Leu Gly Pro Pro Gln
385

<210> SEQ ID NO 43
<211> LENGTH: 346
<212> TYPE: PRT
<213> ORGANISM: Mus muscularis

<400> SEQUENCE: 43

Met Val Gly Gly Gly Lys Arg Arg Thr Ala Gly Ala Gly Pro Gln
1               5                   10                  15

Cys Glu Lys Thr Val Glu Val Lys Lys Ser Lys Phe Ser Glu Ala Asp
            20                  25                  30

Val Ser Ser Asp Leu Arg Lys Glu Val Glu Asn Leu Tyr Lys Leu Ser
        35                  40                  45

Leu Pro Glu Asp Phe Tyr His Phe Trp Lys Phe Cys Glu Glu Leu Asp
50                  55                  60

Pro Glu Lys Pro Ala Asp Ala Leu Ala Thr Ser Leu Gly Leu Arg Leu
65                  70                  75                  80

Val Gly Pro Tyr Asp Ile Leu Ala Gly Lys His Lys Met Lys Lys Lys
                85                  90                  95

Pro Thr Gly Leu Asn Cys Asn Leu His Trp Arg Phe Tyr Tyr Asp Pro
                100                 105                 110

Pro Glu Phe Gln Thr Ile Ile Ile Gly Asp Asn Lys Thr Gln Tyr His
            115                 120                 125

Met Gly Tyr Phe Arg Asp Ser Pro Asp Glu Leu Pro Val Tyr Val Gly
        130                 135                 140

Thr Asn Glu Ala Lys Lys Asn Cys Ile Ile Ile Gln Asn Gly Asp Asn
145                 150                 155                 160

Val Phe Ala Ala Ile Lys Leu Phe Leu Met Lys Lys Leu Lys Glu Val
                165                 170                 175

Thr Asp Arg Lys Lys Ile Ser Ile Leu Lys Asn Ile Asp Glu Lys Leu
            180                 185                 190

Thr Glu Ala Ala Arg Lys Leu Gly Tyr Ser Leu Glu Gln Arg Thr Val
        195                 200                 205

Lys Met Arg Gln Arg Asp Lys Lys Val Val Thr Lys Thr Phe His Gly
210                 215                 220

Ala Gly Leu Val Val Pro Val Asp Lys Asn Asp Val Gly Tyr Arg Glu
225                 230                 235                 240

Leu Pro Glu Thr Asp Ala Asp Leu Lys Arg Ile Cys Lys Ala Val Val
                245                 250                 255

Asp Ala Ala Ser Asp Glu Glu Arg Leu Lys Ala Phe Ala Pro Ile Gln
            260                 265                 270

Glu Met Met Thr Phe Val Gln Phe Ala Asn Asp Glu Cys Asp Tyr Gly
        275                 280                 285

Met Gly Leu Glu Leu Gly Met Asp Leu Phe Cys Tyr Gly Ser His Tyr
290                 295                 300

Phe His Lys Val Ala Gly Gln Leu Leu Pro Leu Ala Tyr Asn Leu Leu
305                 310                 315                 320

Lys Arg Asp Leu Phe Ala Lys Ile Ile Glu Asp His Leu Ala Ser Arg
                325                 330                 335

Ser Glu Glu Asn Ile Asp Gln Leu Ala Gly
            340                 345

<210> SEQ ID NO 44
<211> LENGTH: 199
<212> TYPE: PRT
<213> ORGANISM: Homo sapiens

<400> SEQUENCE: 44

Met Asn Cys Val Cys Arg Leu Val Leu Val Val Leu Ser Leu Trp Pro
1               5                   10                  15

Asp Thr Ala Val Ala Pro Gly Pro Pro Pro Gly Pro Pro Arg Val Ser
            20                  25                  30

Pro Asp Pro Arg Ala Glu Leu Asp Ser Thr Val Leu Leu Thr Arg Ser
         35                  40                  45

Leu Leu Ala Asp Thr Arg Gln Leu Ala Ala Gln Leu Arg Asp Lys Phe
 50                  55                  60

Pro Ala Asp Gly Asp His Asn Leu Asp Ser Leu Pro Thr Leu Ala Met
 65                  70                  75                  80

Ser Ala Gly Ala Leu Gly Ala Leu Gln Leu Pro Gly Val Leu Thr Arg
                 85                  90                  95

Leu Arg Ala Asp Leu Leu Ser Tyr Leu Arg His Val Gln Trp Leu Arg
             100                 105                 110

Arg Ala Gly Gly Ser Ser Leu Lys Thr Leu Glu Pro Glu Leu Gly Thr
         115                 120                 125

Leu Gln Ala Arg Leu Asp Arg Leu Leu Arg Arg Leu Gln Leu Leu Met
 130                 135                 140

Ser Arg Leu Ala Leu Pro Gln Pro Pro Asp Pro Pro Ala Pro Pro
145                 150                 155                 160

Leu Ala Pro Pro Ser Ser Ala Trp Gly Gly Ile Arg Ala Ala His Ala
                 165                 170                 175

Ile Leu Gly Gly Leu His Leu Thr Leu Asp Trp Ala Val Arg Gly Leu
             180                 185                 190

Leu Leu Leu Lys Thr Arg Leu
         195

<210> SEQ ID NO 45
<211> LENGTH: 21531
<212> TYPE: PRT
<213> ORGANISM: Homo sapiens

<400> SEQUENCE: 45

Met Leu Lys Pro Ser Gly Leu Pro Gly Ser Ser Pro Thr Arg Ser
 1               5                  10                  15

Leu Met Thr Gly Ser Arg Ser Thr Lys Ala Thr Pro Glu Met Asp Ser
             20                  25                  30

Gly Leu Thr Gly Ala Thr Leu Ser Pro Lys Ser Thr Gly Ala Ile
         35                  40                  45

Val Val Thr Glu His Thr Leu Pro Phe Thr Ser Pro Asp Lys Thr Leu
 50                  55                  60

Ala Ser Pro Thr Ser Ser Val Val Gly Arg Thr Thr Gln Ser Leu Gly
 65                  70                  75                  80

Val Met Ser Ser Ala Leu Pro Glu Ser Thr Ser Arg Gly Met Thr His
                 85                  90                  95

Ser Glu Gln Arg Thr Ser Pro Ser Leu Ser Pro Gln Val Asn Gly Thr
             100                 105                 110

Pro Ser Arg Asn Tyr Pro Ala Thr Ser Met Val Ser Gly Leu Ser Ser
         115                 120                 125

Pro Arg Thr Arg Thr Ser Thr Glu Gly Asn Phe Thr Lys Glu Ala
 130                 135                 140

Ser Thr Tyr Thr Leu Thr Val Glu Thr Ser Gly Pro Val Thr Glu
145                 150                 155                 160

Lys Tyr Thr Val Pro Thr Glu Thr Ser Thr Glu Gly Asp Ser Thr
                 165                 170                 175

Glu Thr Pro Trp Asp Thr Arg Tyr Ile Pro Val Lys Ile Thr Ser Pro
             180                 185                 190

Met Lys Thr Phe Ala Asp Ser Thr Ala Ser Lys Glu Asn Ala Pro Val
         195                 200                 205

```
Ser Met Thr Pro Ala Glu Thr Thr Val Thr Asp Ser His Thr Pro Gly
    210                 215                 220

Arg Thr Asn Pro Ser Phe Gly Thr Leu Tyr Ser Ser Phe Leu Asp Leu
225                 230                 235                 240

Ser Pro Lys Gly Thr Pro Asn Ser Arg Gly Glu Thr Ser Leu Glu Leu
                245                 250                 255

Ile Leu Ser Thr Thr Gly Tyr Pro Phe Ser Ser Pro Glu Pro Gly Ser
            260                 265                 270

Ala Gly His Ser Arg Ile Ser Thr Ser Ala Pro Leu Ser Ser Ser Ala
        275                 280                 285

Ser Val Leu Asp Asn Lys Ile Ser Glu Thr Ser Ile Phe Ser Gly Gln
    290                 295                 300

Ser Leu Thr Ser Pro Leu Ser Pro Gly Val Pro Glu Ala Arg Ala Ser
305                 310                 315                 320

Thr Met Pro Asn Ser Ala Ile Pro Phe Ser Met Thr Leu Ser Asn Ala
                325                 330                 335

Glu Thr Ser Ala Glu Arg Val Arg Ser Thr Ile Ser Ser Leu Gly Thr
            340                 345                 350

Pro Ser Ile Ser Thr Lys Gln Thr Ala Glu Thr Ile Leu Thr Phe His
        355                 360                 365

Ala Phe Ala Glu Thr Met Asp Ile Pro Ser Thr His Ile Ala Lys Thr
    370                 375                 380

Leu Ala Ser Glu Trp Leu Gly Ser Pro Gly Thr Leu Gly Gly Thr Ser
385                 390                 395                 400

Thr Ser Ala Leu Thr Thr Thr Ser Pro Ser Thr Thr Leu Val Ser Glu
                405                 410                 415

Glu Thr Asn Thr His His Ser Ser Ser Gly Lys Glu Thr Glu Gly Thr
            420                 425                 430

Leu Asn Thr Ser Met Thr Pro Leu Glu Thr Ser Ala Pro Gly Glu Glu
        435                 440                 445

Ser Glu Met Thr Ala Thr Leu Val Pro Thr Leu Gly Phe Thr Thr Leu
    450                 455                 460

Asp Ser Lys Ile Arg Ser Pro Ser Gln Val Ser Ser Ser His Pro Thr
465                 470                 475                 480

Arg Glu Leu Arg Thr Thr Gly Ser Thr Ser Gly Arg Gln Ser Ser Ser
                485                 490                 495

Thr Ala Ala His Gly Ser Ser Asp Ile Leu Arg Ala Thr Thr Ser Ser
            500                 505                 510

Thr Ser Lys Ala Ser Ser Trp Thr Ser Glu Ser Thr Ala Gln Gln Phe
        515                 520                 525

Ser Glu Pro Gln His Thr Gln Trp Val Glu Thr Ser Pro Ser Met Lys
    530                 535                 540

Thr Glu Arg Pro Pro Ala Ser Thr Ser Val Ala Ala Pro Ile Thr Thr
545                 550                 555                 560

Ser Val Pro Ser Val Val Ser Gly Phe Thr Thr Leu Lys Thr Ser Ser
                565                 570                 575

Thr Lys Gly Ile Trp Leu Glu Glu Thr Ser Ala Asp Thr Leu Ile Gly
            580                 585                 590

Glu Ser Thr Ala Gly Pro Thr Thr His Gln Phe Ala Val Pro Thr Gly
        595                 600                 605

Ile Ser Met Thr Gly Gly Ser Ser Thr Arg Gly Ser Gln Gly Thr Thr
    610                 615                 620

His Leu Leu Thr Arg Ala Thr Ala Ser Ser Glu Thr Ser Ala Asp Leu
```

-continued

```
                625                 630                 635                 640
Thr Leu Ala Thr Asn Gly Val Pro Val Ser Ser Pro Ala Val Ser
                    645                 650                 655
Lys Thr Ala Ala Gly Ser Ser Pro Pro Gly Gly Thr Lys Pro Ser Tyr
                    660                 665                 670
Thr Met Val Ser Ser Val Ile Pro Glu Thr Ser Leu Gln Ser Ser
                675                 680                 685
Ala Phe Arg Glu Gly Thr Ser Leu Gly Leu Thr Pro Leu Asn Thr Arg
690                 695                 700
His Pro Phe Ser Ser Pro Glu Pro Asp Ser Ala Gly His Thr Lys Ile
705                 710                 715                 720
Ser Thr Ser Ile Pro Leu Leu Ser Ser Ala Ser Val Leu Glu Asp Lys
                    725                 730                 735
Val Ser Ala Thr Ser Thr Phe Ser His His Lys Ala Thr Ser Ser Ile
                    740                 745                 750
Thr Thr Gly Thr Pro Glu Ile Ser Thr Lys Thr Lys Pro Ser Ser Ala
                755                 760                 765
Val Leu Ser Ser Met Thr Leu Ser Asn Ala Ala Thr Ser Pro Glu Arg
770                 775                 780
Val Arg Asn Ala Thr Ser Pro Leu Thr His Pro Ser Pro Ser Gly Glu
785                 790                 795                 800
Glu Thr Ala Gly Ser Val Leu Thr Leu Ser Ser Ala Glu Thr Thr
                    805                 810                 815
Asp Ser Pro Asn Ile His Pro Thr Gly Thr Leu Thr Ser Glu Ser Ser
                    820                 825                 830
Glu Ser Pro Ser Thr Leu Ser Leu Pro Ser Val Ser Gly Val Lys Thr
                835                 840                 845
Thr Phe Ser Ser Ser Thr Pro Ser Thr His Leu Phe Thr Ser Gly Glu
                850                 855                 860
Glu Thr Glu Glu Thr Ser Asn Pro Ser Val Ser Gln Pro Glu Thr Ser
865                 870                 875                 880
Val Ser Arg Val Arg Thr Thr Leu Ala Ser Thr Ser Val Pro Thr Pro
                    885                 890                 895
Val Phe Pro Thr Met Asp Thr Trp Pro Thr Arg Ser Ala Gln Phe Ser
                    900                 905                 910
Ser Ser His Leu Val Ser Glu Leu Arg Ala Thr Ser Ser Thr Ser Val
                915                 920                 925
Thr Asn Ser Thr Gly Ser Ala Leu Pro Lys Ile Ser His Leu Thr Gly
                    930                 935                 940
Thr Ala Thr Met Ser Gln Thr Asn Arg Asp Thr Phe Asn Asp Ser Ala
945                 950                 955                 960
Ala Pro Gln Ser Thr Thr Trp Pro Glu Thr Ser Pro Arg Phe Lys Thr
                    965                 970                 975
Gly Leu Pro Ser Ala Thr Thr Val Ser Ser Ala Thr Ser Leu
                    980                 985                 990
Ser Ala Thr Val Met Val Ser Lys Phe Thr Ser Pro Ala Thr Ser Ser
                995                 1000                1005
Met Glu Ala Thr Ser Ile Arg Glu Pro Ser Thr Ile Leu Thr Thr
                1010                1015                1020
Glu Thr Thr Asn Gly Pro Gly Ser Met Ala Val Ala Ser Thr Asn Ile
1025                1030                1035                1040
Pro Ile Gly Lys Gly Tyr Ile Thr Glu Gly Arg Leu Asp Thr Ser His
                    1045                1050                1055
```

-continued

Leu Pro Ile Gly Thr Thr Ala Ser Ser Glu Thr Ser Met Asp Phe Thr
            1060                1065                1070

Met Ala Lys Glu Ser Val Ser Met Ser Val Ser Pro Ser Gln Ser Met
        1075                1080                1085

Asp Ala Ala Gly Ser Ser Thr Pro Gly Arg Thr Ser Gln Phe Val Asp
    1090                1095                1100

Thr Phe Ser Asp Asp Val Tyr His Leu Thr Ser Arg Glu Ile Thr Ile
1105                1110                1115                1120

Pro Arg Asp Gly Thr Ser Ser Ala Leu Thr Pro Gln Met Thr Ala Thr
            1125                1130                1135

His Pro Pro Ser Pro Asp Pro Gly Ser Ala Arg Ser Thr Trp Leu Gly
        1140                1145                1150

Ile Leu Ser Ser Ser Pro Ser Ser Pro Thr Pro Lys Val Thr Met Ser
    1155                1160                1165

Ser Thr Phe Ser Thr Gln Arg Val Thr Thr Ser Met Ile Met Asp Thr
    1170                1175                1180

Val Glu Thr Ser Arg Trp Asn Met Pro Asn Leu Pro Ser Thr Thr Ser
1185                1190                1195                1200

Leu Thr Pro Ser Asn Ile Pro Thr Ser Gly Ala Ile Gly Lys Ser Thr
            1205                1210                1215

Leu Val Pro Leu Asp Thr Pro Ser Pro Ala Thr Ser Leu Glu Ala Ser
        1220                1225                1230

Glu Gly Gly Leu Pro Thr Leu Ser Thr Tyr Pro Glu Ser Thr Asn Thr
    1235                1240                1245

Pro Ser Ile His Leu Gly Ala His Ala Ser Ser Glu Ser Pro Ser Thr
    1250                1255                1260

Ile Lys Leu Thr Met Ala Ser Val Val Lys Pro Gly Ser Tyr Thr Pro
1265                1270                1275                1280

Leu Thr Phe Pro Ser Ile Glu Thr His Ile His Val Ser Thr Ala Arg
            1285                1290                1295

Met Ala Tyr Ser Ser Gly Ser Ser Pro Glu Met Thr Ala Pro Gly Glu
        1300                1305                1310

Thr Asn Thr Gly Ser Thr Trp Asp Pro Thr Thr Tyr Ile Thr Thr Thr
    1315                1320                1325

Asp Pro Lys Asp Thr Ser Ser Ala Gln Val Ser Thr Pro His Ser Val
    1330                1335                1340

Arg Thr Leu Arg Thr Thr Glu Asn His Pro Lys Thr Glu Ser Ala Thr
1345                1350                1355                1360

Pro Ala Ala Tyr Ser Gly Ser Pro Lys Ile Ser Ser Ser Pro Asn Leu
            1365                1370                1375

Thr Ser Pro Ala Thr Lys Ala Trp Thr Ile Thr Asp Thr Thr Glu His
        1380                1385                1390

Ser Thr Gln Leu His Tyr Thr Lys Leu Ala Glu Lys Ser Ser Gly Phe
    1395                1400                1405

Glu Thr Gln Ser Ala Pro Gly Pro Val Ser Val Val Ile Pro Thr Ser
    1410                1415                1420

Pro Thr Ile Gly Ser Ser Thr Leu Glu Leu Thr Ser Asp Val Pro Gly
1425                1430                1435                1440

Glu Pro Leu Val Leu Ala Pro Ser Glu Gln Thr Thr Ile Thr Leu Pro
            1445                1450                1455

Met Ala Thr Trp Leu Ser Thr Ser Leu Thr Glu Glu Met Ala Ser Thr
        1460                1465                1470

Asp Leu Asp Ile Ser Ser Pro Ser Ser Pro Met Ser Thr Phe Ala Ile
    1475                1480                1485

```
Phe Pro Pro Met Ser Thr Pro Ser His Glu Leu Ser Lys Ser Glu Ala
    1490                1495                1500

Asp Thr Ser Ala Ile Arg Asn Thr Asp Ser Thr Thr Leu Asp Gln His
1505                1510                1515                1520

Leu Gly Ile Arg Ser Leu Gly Arg Thr Gly Asp Leu Thr Val Pro
            1525                1530                1535

Ile Thr Pro Leu Thr Thr Thr Trp Thr Ser Val Ile Glu His Ser Thr
        1540                1545                1550

Gln Ala Gln Asp Thr Leu Ser Ala Thr Met Ser Pro Thr His Val Thr
    1555                1560                1565

Gln Ser Leu Lys Asp Gln Thr Ser Ile Pro Ala Ser Ala Ser Pro Ser
    1570                1575                1580

His Leu Thr Glu Val Tyr Pro Glu Leu Gly Thr Gln Gly Arg Ser Ser
1585                1590                1595                1600

Ser Glu Ala Thr Thr Phe Trp Lys Pro Ser Thr Asp Thr Leu Ser Arg
            1605                1610                1615

Glu Ile Glu Thr Gly Pro Thr Asn Ile Gln Ser Thr Pro Pro Met Asp
        1620                1625                1630

Asn Thr Thr Thr Gly Ser Ser Ser Gly Val Thr Leu Gly Ile Ala
            1635                1640                1645

His Leu Pro Ile Gly Thr Ser Ser Pro Ala Glu Thr Ser Thr Asn Met
    1650                1655                1660

Ala Leu Glu Arg Arg Ser Ser Thr Ala Thr Val Ser Met Ala Gly Thr
1665                1670                1675                1680

Met Gly Leu Leu Val Thr Ser Ala Pro Gly Arg Ser Ile Ser Gln Ser
            1685                1690                1695

Leu Gly Arg Val Ser Ser Val Leu Ser Glu Ser Thr Thr Glu Gly Val
        1700                1705                1710

Thr Asp Ser Ser Lys Gly Ser Ser Pro Arg Leu Asn Thr Gln Gly Asn
    1715                1720                1725

Thr Ala Leu Ser Ser Ser Leu Glu Pro Ser Tyr Ala Glu Gly Ser Gln
    1730                1735                1740

Met Ser Thr Ser Ile Pro Leu Thr Ser Ser Pro Thr Thr Pro Asp Val
1745                1750                1755                1760

Glu Phe Ile Gly Gly Ser Thr Phe Trp Thr Lys Glu Val Thr Thr Val
            1765                1770                1775

Met Thr Ser Asp Ile Ser Lys Ser Ser Ala Arg Thr Glu Ser Ser Ser
        1780                1785                1790

Ala Thr Leu Met Ser Thr Ala Leu Gly Ser Thr Glu Asn Thr Gly Lys
    1795                1800                1805

Glu Lys Leu Arg Thr Ala Ser Met Asp Leu Pro Ser Pro Thr Pro Ser
    1810                1815                1820

Met Glu Val Thr Pro Trp Ile Ser Leu Thr Leu Ser Asn Ala Pro Asn
1825                1830                1835                1840

Thr Thr Asp Ser Leu Asp Leu Ser His Gly Val His Thr Ser Ser Ala
            1845                1850                1855

Gly Thr Leu Ala Thr Asp Arg Ser Leu Asn Thr Gly Val Thr Arg Ala
        1860                1865                1870

Ser Arg Leu Glu Asn Gly Ser Asp Thr Ser Ser Lys Ser Leu Ser Met
    1875                1880                1885

Gly Asn Ser Thr His Thr Ser Met Thr Asp Thr Glu Lys Ser Glu Val
    1890                1895                1900

Ser Ser Ser Ile His Pro Arg Pro Glu Thr Ser Ala Pro Gly Ala Glu
```

-continued

```
              1905                1910                1915                1920
Thr  Thr  Leu  Thr  Ser  Thr  Pro  Gly  Asn  Arg  Ala  Ile  Ser  Leu  Thr  Leu
                    1925                1930                1935

Pro  Phe  Ser  Ser  Ile  Pro  Val  Glu  Glu  Val  Ile  Ser  Thr  Gly  Ile  Thr
                    1940                1945                1950

Ser  Gly  Pro  Asp  Ile  Asn  Ser  Ala  Pro  Met  Thr  His  Ser  Pro  Ile  Thr
                    1955                1960                1965

Pro  Pro  Thr  Ile  Val  Trp  Thr  Ser  Thr  Gly  Thr  Ile  Glu  Gln  Ser  Thr
                    1970                1975                1980

Gln  Pro  Leu  His  Ala  Val  Ser  Ser  Glu  Lys  Val  Ser  Val  Gln  Thr  Gln
1985                1990                1995                2000

Ser  Thr  Pro  Tyr  Val  Asn  Ser  Val  Ala  Val  Ser  Ala  Ser  Pro  Thr  His
                    2005                2010                2015

Glu  Asn  Ser  Val  Ser  Ser  Gly  Ser  Ser  Thr  Ser  Ser  Pro  Tyr  Ser  Ser
                    2020                2025                2030

Ala  Ser  Leu  Glu  Ser  Leu  Asp  Ser  Thr  Ile  Ser  Arg  Arg  Asn  Ala  Ile
                    2035                2040                2045

Thr  Ser  Trp  Leu  Trp  Asp  Leu  Thr  Thr  Ser  Leu  Pro  Thr  Thr  Thr  Trp
                    2050                2055                2060

Pro  Ser  Thr  Ser  Leu  Ser  Glu  Ala  Leu  Ser  Ser  Gly  His  Ser  Gly  Val
2065                2070                2075                2080

Ser  Asn  Pro  Ser  Ser  Thr  Thr  Thr  Glu  Phe  Pro  Leu  Phe  Ser  Ala  Ala
                    2085                2090                2095

Ser  Thr  Ser  Ala  Ala  Lys  Gln  Arg  Asn  Pro  Glu  Thr  Glu  Thr  His  Gly
                    2100                2105                2110

Pro  Gln  Asn  Thr  Ala  Ala  Ser  Thr  Leu  Asn  Thr  Asp  Ala  Ser  Ser  Val
                    2115                2120                2125

Thr  Gly  Leu  Ser  Glu  Thr  Pro  Val  Gly  Ala  Ser  Ile  Ser  Ser  Glu  Val
                    2130                2135                2140

Pro  Leu  Pro  Met  Ala  Ile  Thr  Ser  Arg  Ser  Asp  Val  Ser  Gly  Leu  Thr
2145                2150                2155                2160

Ser  Glu  Ser  Thr  Ala  Asn  Pro  Ser  Leu  Gly  Thr  Ala  Ser  Ser  Ala  Gly
                    2165                2170                2175

Thr  Lys  Leu  Thr  Arg  Thr  Ile  Ser  Leu  Pro  Thr  Ser  Glu  Ser  Leu  Val
                    2180                2185                2190

Ser  Phe  Arg  Met  Asn  Lys  Asp  Pro  Trp  Thr  Val  Ser  Ile  Pro  Leu  Gly
                    2195                2200                2205

Ser  His  Pro  Thr  Thr  Asn  Thr  Glu  Thr  Ser  Ile  Pro  Val  Asn  Ser  Ala
                    2210                2215                2220

Gly  Pro  Pro  Gly  Leu  Ser  Thr  Val  Ala  Ser  Asp  Val  Ile  Asp  Thr  Pro
2225                2230                2235                2240

Ser  Asp  Gly  Ala  Glu  Ser  Ile  Pro  Thr  Val  Ser  Phe  Ser  Pro  Ser  Pro
                    2245                2250                2255

Asp  Thr  Glu  Val  Thr  Thr  Ile  Ser  His  Phe  Pro  Glu  Lys  Thr  Thr  His
                    2260                2265                2270

Ser  Phe  Arg  Thr  Ile  Ser  Ser  Leu  Thr  His  Glu  Leu  Thr  Ser  Arg  Val
                    2275                2280                2285

Thr  Pro  Ile  Pro  Gly  Asp  Trp  Met  Ser  Ser  Ala  Met  Ser  Thr  Lys  Pro
                    2290                2295                2300

Thr  Gly  Ala  Ser  Pro  Ser  Ile  Thr  Leu  Gly  Glu  Arg  Arg  Thr  Ile  Thr
2305                2310                2315                2320

Ser  Ala  Ala  Pro  Thr  Thr  Ser  Pro  Ile  Val  Leu  Thr  Ala  Ser  Phe  Thr
                    2325                2330                2335
```

-continued

Glu Thr Ser Thr Val Ser Leu Asp Asn Glu Thr Thr Val Lys Thr Ser
            2340                2345                2350

Asp Ile Leu Asp Ala Arg Lys Thr Asn Glu Leu Pro Ser Asp Ser Ser
            2355                2360                2365

Ser Ser Ser Asp Leu Ile Asn Thr Ser Ile Ala Ser Ser Thr Met Asp
            2370                2375                2380

Val Thr Lys Thr Ala Ser Ile Ser Pro Thr Ser Ile Ser Gly Met Thr
2385                2390                2395                2400

Ala Ser Ser Ser Pro Ser Leu Phe Ser Ser Asp Arg Pro Gln Val Pro
            2405                2410                2415

Thr Ser Thr Thr Glu Thr Asn Thr Ala Thr Ser Pro Ser Val Ser Ser
            2420                2425                2430

Asn Thr Tyr Ser Leu Asp Gly Gly Ser Asn Val Gly Thr Pro Ser
            2435                2440                2445

Thr Leu Pro Pro Phe Thr Ile Thr His Pro Val Glu Thr Ser Ser Ala
            2450                2455                2460

Leu Leu Ala Trp Ser Arg Pro Val Arg Thr Phe Ser Thr Met Val Ser
2465                2470                2475                2480

Thr Asp Thr Ala Ser Gly Glu Asn Pro Thr Ser Ser Asn Ser Val Val
            2485                2490                2495

Thr Ser Val Pro Ala Pro Gly Thr Trp Ala Ser Val Gly Ser Thr Thr
            2500                2505                2510

Asp Leu Pro Ala Met Gly Phe Leu Lys Thr Ser Pro Ala Gly Glu Ala
            2515                2520                2525

His Ser Leu Leu Ala Ser Thr Ile Glu Pro Ala Thr Ala Phe Thr Pro
            2530                2535                2540

His Leu Ser Ala Ala Val Val Thr Gly Ser Ser Ala Thr Ser Glu Ala
2545                2550                2555                2560

Ser Leu Leu Thr Thr Ser Glu Ser Lys Ala Ile His Ser Ser Pro Gln
            2565                2570                2575

Thr Pro Thr Thr Pro Thr Ser Gly Ala Asn Trp Glu Thr Ser Ala Thr
            2580                2585                2590

Pro Glu Ser Leu Leu Val Val Thr Glu Thr Ser Asp Thr Thr Leu Thr
            2595                2600                2605

Ser Lys Ile Leu Val Thr Asp Thr Ile Leu Phe Ser Thr Val Ser Thr
            2610                2615                2620

Pro Pro Ser Lys Phe Pro Ser Thr Gly Thr Leu Ser Gly Ala Ser Phe
2625                2630                2635                2640

Pro Thr Leu Leu Pro Asp Thr Pro Ala Ile Pro Leu Thr Ala Thr Glu
            2645                2650                2655

Pro Thr Ser Ser Leu Ala Thr Ser Phe Asp Ser Thr Pro Leu Val Thr
            2660                2665                2670

Ile Ala Ser Asp Ser Leu Gly Thr Val Pro Glu Thr Thr Leu Thr Met
            2675                2680                2685

Ser Glu Thr Ser Asn Gly Asp Ala Leu Val Leu Lys Thr Val Ser Asn
            2690                2695                2700

Pro Asp Arg Ser Ile Pro Gly Ile Thr Ile Gln Gly Val Thr Glu Ser
2705                2710                2715                2720

Pro Leu His Pro Ser Ser Thr Ser Pro Ser Lys Ile Val Ala Pro Arg
            2725                2730                2735

Asn Thr Thr Tyr Glu Gly Ser Ile Thr Val Ala Leu Ser Thr Leu Pro
            2740                2745                2750

Ala Gly Thr Thr Gly Ser Leu Val Phe Ser Gln Ser Ser Glu Asn Ser
            2755                2760                2765

```
Glu Thr Thr Ala Leu Val Asp Ser Ser Ala Gly Leu Glu Arg Ala Ser
            2770                2775                2780

Val Met Pro Leu Thr Thr Gly Ser Gln Gly Met Ala Ser Ser Gly Gly
2785                2790                2795                2800

Ile Arg Ser Gly Ser Thr His Ser Thr Gly Thr Lys Thr Phe Ser Ser
            2805                2810                2815

Leu Pro Leu Thr Met Asn Pro Gly Glu Val Thr Ala Met Ser Glu Ile
            2820                2825                2830

Thr Thr Asn Arg Leu Thr Ala Thr Gln Ser Thr Ala Pro Lys Gly Ile
            2835                2840                2845

Pro Val Lys Pro Thr Ser Ala Glu Ser Gly Leu Leu Thr Pro Val Ser
            2850                2855                2860

Ala Ser Ser Ser Pro Ser Lys Ala Phe Ala Ser Leu Thr Thr Ala Pro
2865                2870                2875                2880

Pro Ser Thr Trp Gly Ile Pro Gln Ser Thr Leu Thr Phe Glu Phe Ser
            2885                2890                2895

Glu Val Pro Ser Leu Asp Thr Lys Ser Ala Ser Leu Pro Thr Pro Gly
            2900                2905                2910

Gln Ser Leu Asn Thr Ile Pro Asp Ser Asp Ala Ser Thr Ala Ser Ser
            2915                2920                2925

Ser Leu Ser Lys Ser Pro Glu Lys Asn Pro Arg Ala Arg Met Met Thr
            2930                2935                2940

Ser Thr Lys Ala Ile Ser Ala Ser Ser Phe Gln Ser Thr Gly Phe Thr
2945                2950                2955                2960

Glu Thr Pro Glu Gly Ser Ala Ser Pro Ser Met Ala Gly His Glu Pro
            2965                2970                2975

Arg Val Pro Thr Ser Gly Thr Gly Asp Pro Arg Tyr Ala Ser Glu Ser
            2980                2985                2990

Met Ser Tyr Pro Asp Pro Ser Lys Ala Ser Ser Ala Met Thr Ser Thr
            2995                3000                3005

Ser Leu Ala Ser Lys Leu Thr Thr Leu Phe Ser Thr Gly Gln Ala Ala
            3010                3015                3020

Arg Ser Gly Ser Ser Ser Ser Pro Ile Ser Leu Ser Thr Glu Lys Glu
3025                3030                3035                3040

Thr Ser Phe Leu Ser Pro Thr Ala Ser Thr Ser Arg Lys Thr Ser Leu
            3045                3050                3055

Phe Leu Gly Pro Ser Met Ala Arg Gln Pro Asn Ile Leu Val His Leu
            3060                3065                3070

Gln Thr Ser Ala Leu Thr Leu Ser Pro Thr Ser Thr Leu Asn Met Ser
            3075                3080                3085

Gln Glu Glu Pro Pro Glu Leu Thr Ser Ser Gln Thr Ile Ala Glu Glu
            3090                3095                3100

Glu Gly Thr Thr Ala Glu Thr Gln Thr Leu Thr Phe Thr Pro Ser Glu
3105                3110                3115                3120

Thr Pro Thr Ser Leu Leu Pro Val Ser Ser Pro Thr Glu Pro Thr Ala
            3125                3130                3135

Arg Arg Lys Ser Ser Pro Glu Thr Trp Ala Ser Ser Ile Ser Val Pro
            3140                3145                3150

Ala Lys Thr Ser Leu Val Glu Thr Thr Asp Gly Thr Leu Val Thr Thr
            3155                3160                3165

Ile Lys Met Ser Ser Gln Ala Ala Gln Gly Asn Ser Thr Trp Pro Ala
            3170                3175                3180

Pro Ala Glu Glu Thr Gly Thr Ser Pro Ala Gly Thr Ser Pro Gly Ser
```

```
                3185                3190                3195                3200
Pro Glu Val Ser Thr Thr Leu Lys Ile Met Ser Ser Lys Glu Pro Ser
                3205                3210                3215
Ile Ser Pro Glu Ile Arg Ser Thr Val Arg Asn Ser Pro Trp Lys Thr
                3220                3225                3230
Pro Glu Thr Thr Val Pro Met Glu Thr Thr Val Glu Pro Val Thr Leu
                3235                3240                3245
Gln Ser Thr Ala Leu Gly Ser Gly Ser Thr Ser Ile Ser His Leu Pro
                3250                3255                3260
Thr Gly Thr Thr Ser Pro Thr Lys Ser Pro Thr Glu Asn Met Leu Ala
3265                3270                3275                3280
Thr Glu Arg Val Ser Leu Ser Pro Ser Pro Glu Ala Trp Thr Asn
                3285                3290                3295
Leu Tyr Ser Gly Thr Pro Gly Gly Thr Arg Gln Ser Leu Ala Thr Met
                3300                3305                3310
Ser Ser Val Ser Leu Glu Ser Pro Thr Ala Arg Ser Ile Thr Gly Thr
                3315                3320                3325
Gly Gln Gln Ser Ser Pro Glu Leu Val Ser Lys Thr Thr Gly Met Glu
                3330                3335                3340
Phe Ser Met Trp His Gly Ser Thr Gly Gly Thr Thr Gly Asp Thr His
3345                3350                3355                3360
Val Ser Leu Ser Thr Ser Ser Asn Ile Leu Glu Asp Pro Val Thr Ser
                3365                3370                3375
Pro Asn Ser Val Ser Ser Leu Thr Asp Lys Ser Lys His Lys Thr Glu
                3380                3385                3390
Thr Trp Val Ser Thr Thr Ala Ile Pro Ser Thr Val Leu Asn Asn Lys
                3395                3400                3405
Ile Met Ala Ala Glu Gln Gln Thr Ser Arg Ser Val Asp Glu Ala Tyr
                3410                3415                3420
Ser Ser Thr Ser Ser Trp Ser Asp Gln Thr Ser Gly Ser Asp Ile Thr
3425                3430                3435                3440
Leu Gly Ala Ser Pro Asp Val Thr Asn Thr Leu Tyr Ile Thr Ser Thr
                3445                3450                3455
Ala Gln Thr Thr Ser Leu Val Ser Leu Pro Ser Gly Asp Gln Gly Ile
                3460                3465                3470
Thr Ser Leu Thr Asn Pro Ser Gly Gly Lys Thr Ser Ser Ala Ser Ser
                3475                3480                3485
Val Thr Ser Pro Ser Ile Gly Leu Glu Thr Leu Arg Ala Asn Val Ser
                3490                3495                3500
Ala Val Lys Ser Asp Ile Ala Pro Thr Ala Gly His Leu Ser Gln Thr
3505                3510                3515                3520
Ser Ser Pro Ala Glu Val Ser Ile Leu Asp Val Thr Ala Pro Thr
                3525                3530                3535
Pro Gly Ile Ser Thr Thr Ile Thr Thr Met Gly Thr Asn Ser Ile Ser
                3540                3545                3550
Thr Thr Thr Pro Asn Pro Glu Val Gly Met Ser Thr Met Asp Ser Thr
                3555                3560                3565
Pro Ala Thr Glu Arg Arg Thr Thr Ser Thr Glu His Pro Ser Thr Trp
                3570                3575                3580
Ser Ser Thr Ala Ala Ser Asp Ser Trp Thr Val Thr Asp Met Thr Ser
3585                3590                3595                3600
Asn Leu Lys Val Ala Arg Ser Pro Gly Thr Ile Ser Thr Met His Thr
                3605                3610                3615
```

-continued

```
Thr Ser Phe Leu Ala Ser Ser Thr Glu Leu Asp Ser Met Ser Thr Pro
            3620                3625                3630

His Gly Arg Ile Thr Val Ile Gly Thr Ser Leu Val Thr Pro Ser Ser
        3635                3640                3645

Asp Ala Ser Ala Val Lys Thr Glu Thr Ser Thr Ser Glu Arg Thr Leu
    3650                3655                3660

Ser Pro Ser Asp Thr Thr Ala Ser Thr Pro Ile Ser Thr Phe Ser Arg
3665                3670                3675                3680

Val Gln Arg Met Ser Ile Ser Val Pro Asp Ile Leu Ser Thr Ser Trp
                3685                3690                3695

Thr Pro Ser Ser Thr Glu Ala Glu Asp Val Pro Val Ser Met Val Ser
            3700                3705                3710

Thr Asp His Ala Ser Thr Lys Thr Asp Pro Asn Thr Pro Leu Ser Thr
        3715                3720                3725

Phe Leu Phe Asp Ser Leu Ser Thr Leu Asp Trp Asp Thr Gly Arg Ser
    3730                3735                3740

Leu Ser Ser Ala Thr Ala Thr Ser Ala Pro Gln Gly Ala Thr Thr
3745                3750                3755                3760

Pro Gln Glu Leu Thr Leu Glu Thr Met Ile Ser Pro Ala Thr Ser Gln
                3765                3770                3775

Leu Pro Phe Ser Ile Gly His Ile Thr Ser Ala Val Thr Pro Ala Ala
            3780                3785                3790

Met Ala Arg Ser Ser Gly Val Thr Phe Ser Arg Pro Asp Pro Thr Ser
        3795                3800                3805

Lys Lys Ala Glu Gln Thr Ser Thr Gln Leu Pro Thr Thr Thr Ser Ala
    3810                3815                3820

His Pro Gly Gln Val Pro Arg Ser Ala Ala Thr Thr Leu Asp Val Ile
3825                3830                3835                3840

Pro His Thr Ala Lys Thr Pro Asp Ala Thr Phe Gln Arg Gln Gly Gln
                3845                3850                3855

Thr Ala Leu Thr Thr Glu Ala Arg Ala Thr Ser Asp Ser Trp Asn Glu
            3860                3865                3870

Lys Glu Lys Ser Thr Pro Ser Ala Pro Trp Ile Thr Glu Met Met Asn
        3875                3880                3885

Ser Val Ser Glu Asp Thr Ile Lys Glu Val Thr Ser Ser Ser Ser Val
    3890                3895                3900

Leu Lys Asp Pro Glu Tyr Ala Gly His Lys Leu Gly Ile Trp Asp Asp
3905                3910                3915                3920

Phe Ile Pro Lys Phe Gly Lys Ala Ala His Met Arg Glu Leu Pro Leu
                3925                3930                3935

Leu Ser Pro Pro Gln Asp Lys Gly Ala Ile His Pro Ser Thr Asn Thr
            3940                3945                3950

Val Glu Thr Thr Gly Trp Val Thr Ser Ser Glu His Ala Ser His Ser
        3955                3960                3965

Thr Ile Pro Ala His Ser Ala Ser Ser Lys Leu Thr Ser Pro Val Val
    3970                3975                3980

Thr Thr Ser Thr Arg Glu Gln Ala Ile Val Ser Met Ser Thr Thr Thr
3985                3990                3995                4000

Trp Pro Glu Ser Thr Arg Ala Arg Thr Glu Pro Asn Ser Phe Leu Thr
                4005                4010                4015

Ile Glu Leu Arg Asp Val Ser Pro Tyr Met Asp Thr Ser Ser Thr Thr
            4020                4025                4030

Gln Thr Ser Ile Ile Ser Ser Pro Gly Ser Thr Ala Ile Thr Lys Gly
        4035                4040                4045
```

Pro Arg Thr Glu Ile Thr Ser Ser Lys Arg Ile Ser Ser Ser Phe Leu
             4050                4055                4060

Ala Gln Ser Met Arg Ser Ser Asp Ser Pro Ser Glu Ala Ile Thr Arg
4065                4070                4075                4080

Leu Ser Asn Phe Pro Ala Met Thr Glu Ser Gly Gly Met Ile Leu Ala
                4085                4090                4095

Met Gln Thr Ser Pro Pro Gly Ala Thr Ser Leu Ser Ala Pro Thr Leu
            4100                4105                4110

Asp Thr Ser Ala Thr Ala Ser Trp Thr Gly Thr Pro Leu Ala Thr Thr
            4115                4120                4125

Gln Arg Phe Thr Tyr Ser Glu Lys Thr Thr Leu Phe Ser Lys Gly Pro
            4130                4135                4140

Glu Asp Thr Ser Gln Pro Ser Pro Ser Val Glu Glu Thr Ser Ser
4145                4150                4155                4160

Ser Ser Ser Leu Val Pro Ile His Ala Thr Thr Ser Pro Ser Asn Ile
                4165                4170                4175

Leu Leu Thr Ser Gln Gly His Ser Pro Ser Ser Thr Pro Pro Val Thr
                4180                4185                4190

Ser Val Phe Leu Ser Glu Thr Ser Gly Leu Gly Lys Thr Thr Asp Met
    4195                4200                4205

Ser Arg Ile Ser Leu Glu Pro Gly Thr Ser Leu Pro Pro Asn Leu Ser
    4210                4215                4220

Ser Thr Ala Gly Glu Ala Leu Ser Thr Tyr Glu Ala Ser Arg Asp Thr
4225                4230                4235                4240

Lys Ala Ile His His Ser Ala Asp Thr Ala Val Thr Asn Met Glu Ala
                4245                4250                4255

Thr Ser Ser Glu Tyr Ser Pro Ile Pro Gly His Thr Lys Pro Ser Lys
            4260                4265                4270

Ala Thr Ser Pro Leu Val Thr Ser His Ile Met Gly Asp Ile Thr Ser
            4275                4280                4285

Ser Thr Ser Val Phe Gly Ser Ser Glu Thr Thr Glu Ile Glu Thr Val
    4290                4295                4300

Ser Ser Val Asn Gln Gly Leu Gln Glu Arg Ser Thr Ser Gln Val Ala
4305                4310                4315                4320

Ser Ser Ala Thr Glu Thr Ser Thr Val Ile Thr His Val Ser Ser Gly
            4325                4330                4335

Asp Ala Thr Thr His Val Thr Lys Thr Gln Ala Thr Phe Ser Ser Gly
            4340                4345                4350

Thr Ser Ile Ser Ser Pro His Gln Phe Ile Thr Ser Thr Asn Thr Phe
            4355                4360                4365

Thr Asp Val Ser Thr Asn Pro Ser Thr Ser Leu Ile Met Thr Glu Ser
            4370                4375                4380

Ser Gly Val Thr Ile Thr Thr Gln Thr Gly Pro Thr Gly Ala Ala Thr
4385                4390                4395                4400

Gln Gly Pro Tyr Leu Leu Asp Thr Ser Thr Met Pro Tyr Leu Thr Glu
                4405                4410                4415

Thr Pro Leu Ala Val Thr Pro Asp Phe Met Gln Ser Glu Lys Thr Thr
            4420                4425                4430

Leu Ile Ser Lys Gly Pro Lys Asp Val Thr Trp Thr Ser Pro Pro Ser
            4435                4440                4445

Val Ala Glu Thr Ser Tyr Pro Ser Ser Leu Thr Pro Phe Leu Val Thr
            4450                4455                4460

Thr Ile Pro Pro Ala Thr Ser Thr Leu Gln Gly Gln His Thr Ser Ser

-continued

```
            4465                4470                4475                4480
Pro Val Ser Ala Thr Ser Val Leu Thr Ser Gly Leu Val Lys Thr Thr
                4485                4490                4495
Asp Met Leu Asn Thr Ser Met Glu Pro Val Thr Asn Ser Pro Gln Asn
                4500                4505                4510
Leu Asn Asn Pro Ser Asn Glu Ile Leu Ala Thr Leu Ala Ala Thr Thr
                4515                4520                4525
Asp Ile Glu Thr Ile His Pro Ser Ile Asn Lys Ala Val Thr Asn Met
                4530                4535                4540
Gly Thr Ala Ser Ser Ala His Val Leu His Ser Thr Leu Pro Val Ser
4545                4550                4555                4560
Ser Glu Pro Ser Thr Ala Thr Ser Pro Met Val Pro Ala Ser Ser Met
                4565                4570                4575
Gly Asp Ala Leu Ala Ser Ile Ser Ile Pro Gly Ser Glu Thr Thr Asp
                4580                4585                4590
Ile Glu Gly Glu Pro Thr Ser Ser Leu Thr Ala Gly Arg Lys Glu Asn
                4595                4600                4605
Ser Thr Leu Gln Glu Met Asn Ser Thr Thr Glu Ser Asn Ile Ile Leu
                4610                4615                4620
Ser Asn Val Ser Val Gly Ala Ile Thr Glu Ala Thr Lys Met Glu Val
4625                4630                4635                4640
Pro Ser Phe Asp Ala Thr Phe Ile Pro Thr Pro Ala Gln Ser Thr Lys
                4645                4650                4655
Phe Pro Asp Ile Phe Ser Val Ala Ser Ser Arg Leu Ser Asn Ser Pro
                4660                4665                4670
Pro Met Thr Ile Ser Thr His Met Thr Thr Thr Gln Thr Gly Ser Ser
                4675                4680                4685
Gly Ala Thr Ser Lys Ile Pro Leu Ala Leu Asp Thr Ser Thr Leu Glu
                4690                4695                4700
Thr Ser Ala Gly Thr Pro Ser Val Val Thr Glu Gly Phe Ala His Ser
4705                4710                4715                4720
Lys Ile Thr Thr Ala Met Asn Asn Asp Val Lys Asp Val Ser Gln Thr
                4725                4730                4735
Asn Pro Pro Phe Gln Asp Glu Ala Ser Ser Pro Ser Ser Gln Ala Pro
                4740                4745                4750
Val Leu Val Thr Thr Leu Pro Ser Ser Val Ala Phe Thr Pro Gln Trp
                4755                4760                4765
His Ser Thr Ser Ser Pro Val Ser Met Ser Ser Val Leu Thr Ser Ser
                4770                4775                4780
Leu Val Lys Thr Ala Gly Lys Val Asp Thr Ser Leu Glu Thr Val Thr
4785                4790                4795                4800
Ser Ser Pro Gln Ser Met Ser Asn Thr Leu Asp Asp Ile Ser Val Thr
                4805                4810                4815
Ser Ala Ala Thr Thr Asp Ile Glu Thr Thr His Pro Ser Ile Asn Thr
                4820                4825                4830
Val Val Thr Asn Val Gly Thr Thr Gly Ser Ala Phe Glu Ser His Ser
                4835                4840                4845
Thr Val Ser Ala Tyr Pro Glu Pro Ser Lys Val Thr Ser Pro Asn Val
                4850                4855                4860
Thr Thr Ser Thr Met Glu Asp Thr Thr Ile Ser Arg Ser Ile Pro Lys
4865                4870                4875                4880
Ser Ser Lys Thr Thr Arg Thr Glu Thr Thr Ser Ser Leu Thr
                4885                4890                4895
```

```
Pro Lys Leu Arg Glu Thr Ser Ile Ser Gln Glu Ile Thr Ser Ser Thr
            4900                4905                4910

Glu Thr Ser Thr Val Pro Tyr Lys Glu Leu Thr Gly Ala Thr Thr Glu
        4915                4920                4925

Val Ser Arg Thr Asp Val Thr Ser Ser Ser Thr Ser Phe Pro Gly
    4930                4935                4940

Pro Asp Gln Ser Thr Val Ser Leu Asp Ile Ser Thr Glu Thr Asn Thr
4945                4950                4955                4960

Arg Leu Ser Thr Ser Pro Ile Met Thr Glu Ser Ala Glu Ile Thr Ile
                4965                4970                4975

Thr Thr Gln Thr Gly Pro His Gly Ala Thr Ser Gln Thr Phe Thr
            4980                4985                4990

Met Asp Pro Ser Asn Thr Thr Pro Gln Ala Gly Ile His Ser Ala Met
        4995                5000                5005

Thr His Gly Phe Ser Gln Leu Asp Val Thr Thr Leu Met Ser Arg Ile
    5010                5015                5020

Pro Gln Asp Val Ser Trp Thr Ser Pro Ser Val Asp Lys Thr Ser
5025                5030                5035                5040

Ser Pro Ser Ser Phe Leu Ser Pro Ala Met Thr Thr Pro Ser Leu
            5045                5050                5055

Ile Ser Ser Thr Leu Pro Glu Asp Lys Leu Ser Ser Pro Met Thr Ser
        5060                5065                5070

Leu Leu Thr Ser Gly Leu Val Lys Ile Thr Asp Ile Leu Arg Thr Arg
    5075                5080                5085

Leu Glu Pro Val Thr Ser Ser Leu Pro Asn Phe Ser Thr Ser Asp
            5090                5095                5100

Lys Ile Leu Ala Thr Ser Lys Asp Ser Lys Asp Thr Lys Glu Ile Phe
5105                5110                5115                5120

Pro Ser Ile Asn Thr Glu Glu Thr Asn Val Lys Ala Asn Asn Ser Gly
            5125                5130                5135

His Glu Ser His Ser Pro Ala Leu Ala Asp Ser Glu Thr Pro Lys Ala
        5140                5145                5150

Thr Thr Gln Met Val Ile Thr Thr Thr Val Gly Asp Pro Ala Pro Ser
    5155                5160                5165

Thr Ser Met Pro Val His Gly Ser Ser Glu Thr Thr Asn Ile Lys Arg
    5170                5175                5180

Glu Pro Thr Tyr Phe Leu Thr Pro Arg Leu Arg Glu Thr Ser Thr Ser
5185                5190                5195                5200

Gln Glu Ser Ser Phe Pro Thr Asp Thr Ser Phe Leu Leu Ser Lys Val
            5205                5210                5215

Pro Thr Gly Thr Ile Thr Glu Val Ser Ser Thr Gly Val Asn Ser Ser
        5220                5225                5230

Ser Lys Ile Ser Thr Pro Asp His Asp Lys Ser Thr Val Pro Pro Asp
    5235                5240                5245

Thr Phe Thr Gly Glu Ile Pro Arg Val Phe Thr Ser Ser Ile Lys Thr
    5250                5255                5260

Lys Ser Ala Glu Met Thr Ile Thr Thr Gln Ala Ser Pro Pro Glu Ser
5265                5270                5275                5280

Ala Ser His Ser Thr Leu Pro Leu Asp Thr Ser Thr Thr Leu Ser Gln
            5285                5290                5295

Gly Gly Thr His Ser Thr Val Thr Gln Gly Phe Pro Tyr Ser Glu Val
        5300                5305                5310

Thr Thr Leu Met Gly Met Gly Pro Gly Asn Val Ser Trp Met Thr Thr
    5315                5320                5325
```

Pro Pro Val Glu Glu Thr Ser Ser Val Ser Ser Leu Met Ser Pro
    5330                5335                5340

Ala Met Thr Ser Pro Ser Pro Val Ser Ser Thr Ser Pro Gln Ser Ile
5345                5350                5355                5360

Pro Ser Ser Pro Leu Pro Val Thr Ala Leu Pro Thr Ser Val Leu Val
            5365                5370                5375

Thr Thr Thr Asp Val Leu Gly Thr Thr Ser Pro Glu Ser Val Thr Ser
        5380                5385                5390

Ser Pro Pro Asn Leu Ser Ser Ile Thr His Glu Arg Pro Ala Thr Tyr
    5395                5400                5405

Lys Asp Thr Ala His Thr Glu Ala Ala Met His His Ser Thr Asn Thr
    5410                5415                5420

Ala Val Thr Asn Val Gly Thr Ser Gly Ser Gly His Lys Ser Gln Ser
5425                5430                5435                5440

Ser Val Leu Ala Asp Ser Glu Thr Ser Lys Ala Thr Pro Leu Met Ser
            5445                5450                5455

Thr Thr Ser Thr Leu Gly Asp Thr Ser Val Ser Thr Ser Thr Pro Asn
        5460                5465                5470

Ile Ser Gln Thr Asn Gln Ile Gln Thr Glu Pro Thr Ala Ser Leu Ser
    5475                5480                5485

Pro Arg Leu Arg Glu Ser Ser Thr Ser Glu Lys Thr Ser Ser Thr Thr
    5490                5495                5500

Glu Thr Asn Thr Ala Phe Ser Tyr Val Pro Thr Gly Ala Ile Thr Gln
5505                5510                5515                5520

Ala Ser Arg Thr Glu Ile Ser Ser Arg Thr Ser Ile Ser Asp Leu
            5525                5530                5535

Asp Arg Pro Thr Ile Ala Pro Asp Ile Ser Thr Gly Met Ile Thr Arg
        5540                5545                5550

Leu Phe Thr Ser Pro Ile Met Thr Lys Ser Ala Glu Met Thr Val Thr
    5555                5560                5565

Thr Gln Thr Thr Thr Pro Gly Ala Thr Ser Gln Gly Ile Leu Pro Trp
    5570                5575                5580

Asp Thr Ser Thr Thr Leu Phe Gln Gly Gly Thr His Ser Thr Val Ser
5585                5590                5595                5600

Gln Gly Phe Pro His Ser Glu Ile Thr Thr Leu Arg Ser Arg Thr Pro
            5605                5610                5615

Gly Asp Val Ser Trp Met Thr Thr Pro Pro Val Glu Glu Thr Ser Ser
        5620                5625                5630

Gly Phe Ser Leu Met Ser Pro Ser Met Thr Ser Pro Ser Pro Val Ser
    5635                5640                5645

Ser Thr Ser Pro Glu Ser Ile Pro Ser Ser Pro Leu Pro Val Thr Ala
    5650                5655                5660

Leu Leu Thr Ser Val Leu Val Thr Thr Thr Asn Val Leu Gly Thr Thr
5665                5670                5675                5680

Ser Pro Glu Thr Val Thr Ser Ser Pro Pro Asn Leu Ser Ser Pro Thr
            5685                5690                5695

Gln Glu Arg Leu Thr Thr Tyr Lys Asp Thr Ala His Thr Glu Ala Met
        5700                5705                5710

His Ala Ser Met His Thr Asn Thr Ala Val Ala Asn Val Gly Thr Ser
    5715                5720                5725

Ile Ser Gly His Glu Ser Gln Ser Ser Val Pro Ala Asp Ser His Thr
    5730                5735                5740

Ser Lys Ala Thr Ser Pro Met Gly Ile Thr Phe Ala Met Gly Asp Thr

```
            5745              5750              5755              5760
Ser Val Ser Thr Ser Thr Pro Ala Phe Phe Glu Thr Arg Ile Gln Thr
                5765              5770              5775
Glu Ser Thr Ser Ser Leu Ile Pro Gly Leu Arg Asp Thr Arg Thr Ser
                5780              5785              5790
Glu Glu Ile Asn Thr Val Thr Glu Thr Ser Thr Val Leu Ser Glu Val
                5795              5800              5805
Pro Thr Thr Thr Thr Thr Glu Val Ser Arg Thr Glu Val Ile Thr Ser
                5810              5815              5820
Ser Arg Thr Thr Ile Ser Gly Pro Asp His Ser Lys Met Ser Pro Tyr
5825              5830              5835              5840
Ile Ser Thr Glu Thr Ile Thr Arg Leu Ser Thr Phe Pro Phe Val Thr
                5845              5850              5855
Gly Ser Thr Glu Met Ala Ile Thr Asn Gln Thr Gly Pro Ile Gly Thr
                5860              5865              5870
Ile Ser Gln Ala Thr Leu Thr Leu Asp Thr Ser Ser Thr Ala Ser Trp
                5875              5880              5885
Glu Gly Thr His Ser Pro Val Thr Gln Arg Phe Pro His Ser Glu Glu
                5890              5895              5900
Thr Thr Thr Met Ser Arg Ser Thr Lys Gly Val Ser Trp Gln Ser Pro
5905              5910              5915              5920
Pro Ser Val Glu Glu Thr Ser Ser Pro Ser Ser Pro Val Pro Leu Pro
                5925              5930              5935
Ala Ile Thr Ser His Ser Ser Leu Tyr Ser Ala Val Ser Gly Ser Ser
                5940              5945              5950
Pro Thr Ser Ala Leu Pro Val Thr Ser Leu Leu Thr Ser Gly Arg Arg
                5955              5960              5965
Lys Thr Ile Asp Met Leu Asp Thr His Ser Glu Leu Val Thr Ser Ser
                5970              5975              5980
Leu Pro Ser Ala Ser Ser Phe Ser Gly Glu Ile Leu Thr Ser Glu Ala
5985              5990              5995              6000
Ser Thr Asn Thr Glu Thr Ile His Phe Ser Glu Asn Thr Ala Glu Thr
                6005              6010              6015
Asn Met Gly Thr Thr Asn Ser Met His Lys Leu His Ser Ser Val Ser
                6020              6025              6030
Ile His Ser Gln Pro Ser Gly His Thr Pro Pro Lys Val Thr Gly Ser
                6035              6040              6045
Met Met Glu Asp Ala Ile Val Ser Thr Ser Thr Pro Gly Ser Pro Glu
                6050              6055              6060
Thr Lys Asn Val Asp Arg Asp Ser Thr Ser Pro Leu Thr Pro Glu Leu
6065              6070              6075              6080
Lys Glu Asp Ser Thr Ala Leu Val Met Asn Ser Thr Thr Glu Ser Asn
                6085              6090              6095
Thr Val Phe Ser Ser Val Ser Leu Asp Ala Ala Thr Glu Val Ser Arg
                6100              6105              6110
Ala Glu Val Thr Tyr Tyr Asp Pro Thr Phe Met Pro Ala Ser Ala Gln
                6115              6120              6125
Ser Thr Lys Ser Pro Asp Ile Ser Pro Glu Ala Ser Ser Ser His Ser
                6130              6135              6140
Asn Ser Pro Pro Leu Thr Ile Ser Thr His Lys Thr Ile Ala Thr Gln
6145              6150              6155              6160
Thr Gly Pro Ser Gly Val Thr Ser Leu Gly Gln Leu Thr Leu Asp Thr
                6165              6170              6175
```

```
Ser Thr Ile Ala Thr Ser Ala Gly Thr Pro Ser Ala Arg Thr Gln Asp
            6180                6185                6190

Phe Val Asp Ser Glu Thr Thr Ser Val Met Asn Asn Asp Leu Asn Asp
        6195                6200                6205

Val Leu Lys Thr Ser Pro Phe Ser Ala Glu Glu Ala Asn Ser Leu Ser
            6210                6215                6220

Ser Gln Ala Pro Leu Leu Val Thr Thr Ser Pro Ser Pro Val Thr Ser
6225                6230                6235                6240

Thr Leu Gln Glu His Ser Thr Ser Ser Leu Val Ser Val Thr Ser Val
                6245                6250                6255

Pro Thr Pro Thr Leu Ala Lys Ile Thr Asp Met Asp Thr Asn Leu Glu
            6260                6265                6270

Pro Val Thr Arg Ser Pro Gln Asn Leu Arg Asn Thr Leu Ala Thr Ser
        6275                6280                6285

Glu Ala Thr Thr Asp Thr His Thr Met His Pro Ser Ile Asn Thr Ala
            6290                6295                6300

Met Ala Asn Val Gly Thr Thr Ser Ser Pro Asn Glu Phe Tyr Phe Thr
6305                6310                6315                6320

Val Ser Pro Asp Ser Asp Pro Tyr Lys Ala Thr Ser Ala Val Val Ile
                6325                6330                6335

Thr Ser Thr Ser Gly Asp Ser Ile Val Ser Thr Ser Met Pro Arg Ser
            6340                6345                6350

Ser Ala Met Lys Lys Ile Glu Ser Glu Thr Thr Phe Ser Leu Ile Phe
        6355                6360                6365

Arg Leu Arg Glu Thr Ser Thr Ser Gln Lys Ile Gly Ser Ser Ser Asp
            6370                6375                6380

Thr Ser Thr Val Phe Asp Lys Ala Phe Thr Ala Ala Thr Thr Glu Val
6385                6390                6395                6400

Ser Arg Thr Glu Leu Thr Ser Ser Arg Thr Ser Ile Gln Gly Thr
            6405                6410                6415

Glu Lys Pro Thr Met Ser Pro Asp Thr Ser Thr Arg Ser Val Thr Met
            6420                6425                6430

Leu Ser Thr Phe Ala Gly Leu Thr Lys Ser Glu Glu Arg Thr Ile Ala
            6435                6440                6445

Thr Gln Thr Gly Pro His Arg Ala Thr Ser Gln Gly Thr Leu Thr Trp
            6450                6455                6460

Asp Thr Ser Ile Thr Thr Ser Gln Ala Gly Thr His Ser Ala Met Thr
6465                6470                6475                6480

His Gly Phe Ser Gln Leu Asp Leu Ser Thr Leu Thr Ser Arg Val Pro
            6485                6490                6495

Glu Tyr Ile Ser Gly Thr Ser Pro Pro Ser Val Glu Lys Thr Ser Ser
            6500                6505                6510

Ser Ser Ser Leu Leu Ser Leu Pro Ala Ile Thr Ser Pro Ser Pro Val
            6515                6520                6525

Pro Thr Thr Leu Pro Glu Ser Arg Pro Ser Ser Pro Val His Leu Thr
            6530                6535                6540

Ser Leu Pro Thr Ser Gly Leu Val Lys Thr Thr Asp Met Leu Ala Ser
6545                6550                6555                6560

Val Ala Ser Leu Pro Pro Asn Leu Gly Ser Thr Ser His Lys Ile Pro
            6565                6570                6575

Thr Thr Ser Glu Asp Ile Lys Asp Thr Glu Lys Met Tyr Pro Ser Thr
            6580                6585                6590

Asn Ile Ala Val Thr Asn Val Gly Thr Thr Thr Ser Glu Lys Glu Ser
            6595                6600                6605
```

```
Tyr Ser Ser Val Pro Ala Tyr Ser Glu Pro Lys Val Thr Ser Pro
    6610            6615            6620

Met Val Thr Ser Phe Asn Ile Arg Asp Thr Ile Val Ser Thr Ser Met
6625            6630            6635            6640

Pro Gly Ser Ser Glu Ile Thr Arg Ile Glu Met Glu Ser Thr Phe Ser
                6645            6650            6655

Val Ala His Gly Leu Lys Gly Thr Ser Thr Ser Gln Asp Pro Ile Val
            6660            6665            6670

Ser Thr Glu Lys Ser Ala Val Leu His Lys Leu Thr Thr Gly Ala Thr
        6675            6680            6685

Glu Thr Ser Arg Thr Glu Val Ala Ser Ser Arg Arg Thr Ser Ile Pro
    6690            6695            6700

Gly Pro Asp His Ser Thr Glu Ser Pro Asp Ile Ser Thr Glu Val Ile
6705            6710            6715            6720

Pro Ser Leu Pro Ile Ser Leu Gly Ile Thr Glu Ser Ser Asn Met Thr
                6725            6730            6735

Ile Ile Thr Arg Thr Gly Pro Pro Leu Gly Ser Thr Ser Gln Gly Thr
            6740            6745            6750

Phe Thr Leu Asp Thr Pro Thr Thr Ser Ser Arg Ala Gly Thr His Ser
        6755            6760            6765

Met Ala Thr Gln Glu Phe Pro His Ser Glu Met Thr Ser Val Met Asn
    6770            6775            6780

Lys Asp Pro Glu Ile Leu Ser Trp Thr Ile Pro Pro Ser Ile Glu Lys
6785            6790            6795            6800

Thr Ser Phe Ser Ser Ser Leu Met Pro Ser Pro Ala Met Thr Ser Pro
                6805            6810            6815

Pro Val Ser Ser Thr Leu Pro Lys Thr Ile His Thr Thr Pro Ser Pro
            6820            6825            6830

Met Thr Ser Leu Leu Thr Pro Ser Leu Val Met Thr Thr Asp Thr Leu
        6835            6840            6845

Gly Thr Ser Pro Glu Pro Thr Thr Ser Ser Pro Pro Asn Leu Ser Ser
    6850            6855            6860

Thr Ser His Val Ile Leu Thr Thr Asp Glu Asp Thr Thr Ala Ile Glu
6865            6870            6875            6880

Ala Met His Pro Ser Thr Ser Thr Ala Ala Thr Asn Val Glu Thr Thr
                6885            6890            6895

Cys Ser Gly His Gly Ser Gln Ser Ser Val Leu Thr Asp Ser Glu Lys
            6900            6905            6910

Thr Lys Ala Thr Ala Pro Met Asp Thr Thr Ser Thr Met Gly His Thr
        6915            6920            6925

Thr Val Ser Thr Ser Met Ser Val Ser Ser Glu Thr Thr Lys Ile Lys
    6930            6935            6940

Arg Glu Ser Thr Tyr Ser Leu Thr Pro Gly Leu Arg Glu Thr Ser Ile
6945            6950            6955            6960

Ser Gln Asn Ala Ser Phe Ser Thr Asp Thr Ser Ile Val Leu Ser Glu
                6965            6970            6975

Val Pro Thr Gly Thr Thr Ala Glu Val Ser Arg Thr Glu Val Thr Ser
            6980            6985            6990

Ser Gly Arg Thr Ser Ile Pro Gly Pro Ser Gln Ser Thr Val Leu Pro
        6995            7000            7005

Glu Ile Ser Thr Arg Thr Met Thr Arg Leu Phe Ala Ser Pro Thr Met
    7010            7015            7020

Thr Glu Ser Ala Glu Met Thr Ile Pro Thr Gln Thr Gly Pro Ser Gly
```

```
              7025                7030                7035                7040
Ser Thr Ser Gln Asp Thr Leu Thr Leu Asp Thr Ser Thr Thr Lys Ser
                    7045                7050                7055

Gln Ala Lys Thr His Ser Thr Leu Thr Gln Arg Phe Pro His Ser Glu
                    7060                7065                7070

Met Thr Thr Leu Met Ser Arg Gly Pro Gly Asp Met Ser Trp Gln Ser
                    7075                7080                7085

Ser Pro Ser Leu Glu Asn Pro Ser Leu Pro Ser Leu Leu Ser Leu
                    7090                7095                7100

Pro Ala Thr Thr Ser Pro Pro Ile Ser Ser Thr Leu Pro Val Thr
7105                7110                7115                7120

Ile Ser Ser Ser Pro Leu Pro Val Thr Ser Leu Leu Thr Ser Ser Pro
                    7125                7130                7135

Val Thr Thr Thr Asp Met Leu His Thr Ser Pro Glu Leu Val Thr Ser
                    7140                7145                7150

Ser Pro Pro Lys Leu Ser His Thr Ser Asp Glu Arg Leu Thr Thr Gly
                    7155                7160                7165

Lys Asp Thr Thr Asn Thr Glu Ala Val His Pro Ser Thr Asn Thr Ala
                    7170                7175                7180

Ala Ser Asn Val Glu Ile Pro Ser Phe Gly His Glu Ser Pro Ser Ser
7185                7190                7195                7200

Ala Leu Ala Asp Ser Glu Thr Ser Lys Ala Thr Ser Pro Met Phe Ile
                    7205                7210                7215

Thr Ser Thr Gln Glu Asp Thr Val Ala Ile Ser Thr Pro His Phe
                    7220                7225                7230

Leu Glu Thr Ser Arg Ile Gln Lys Glu Ser Ile Ser Ser Leu Ser Pro
                    7235                7240                7245

Lys Leu Arg Glu Thr Gly Ser Ser Val Glu Thr Ser Ser Ala Ile Glu
                    7250                7255                7260

Thr Ser Ala Val Leu Ser Glu Val Ser Ile Gly Ala Thr Thr Glu Ile
7265                7270                7275                7280

Ser Arg Thr Glu Val Thr Ser Ser Ser Arg Thr Ser Ile Ser Gly Ser
                    7285                7290                7295

Ala Glu Ser Thr Met Leu Pro Glu Ile Ser Thr Thr Arg Lys Ile Ile
                    7300                7305                7310

Lys Phe Pro Thr Ser Pro Ile Leu Ala Glu Ser Ser Glu Met Thr Ile
                    7315                7320                7325

Lys Thr Gln Thr Ser Pro Pro Gly Ser Thr Ser Glu Ser Thr Phe Thr
                    7330                7335                7340

Leu Asp Thr Ser Thr Thr Pro Ser Leu Val Ile Thr His Ser Thr Met
7345                7350                7355                7360

Thr Gln Arg Leu Pro His Ser Glu Ile Thr Thr Leu Val Ser Arg Gly
                    7365                7370                7375

Ala Gly Asp Val Pro Arg Pro Ser Ser Leu Pro Val Glu Glu Thr Ser
                    7380                7385                7390

Pro Pro Ser Ser Gln Leu Ser Leu Ser Ala Met Ile Ser Pro Ser Pro
                    7395                7400                7405

Val Ser Ser Thr Leu Pro Ala Ser Ser His Ser Ser Ser Ala Ser Val
                    7410                7415                7420

Thr Ser Pro Leu Thr Pro Gly Gln Val Lys Thr Thr Glu Val Leu Asp
7425                7430                7435                7440

Ala Ser Ala Glu Pro Glu Thr Ser Ser Pro Pro Ser Leu Ser Ser Thr
                    7445                7450                7455
```

-continued

```
Ser Val Glu Ile Leu Ala Thr Ser Glu Val Thr Thr Asp Thr Glu Lys
            7460                7465                7470

Ile His Pro Phe Pro Asn Thr Ala Val Thr Lys Val Gly Thr Ser Ser
            7475                7480                7485

Ser Gly His Glu Ser Pro Ser Ser Val Leu Pro Asp Ser Glu Thr Thr
            7490                7495                7500

Lys Ala Thr Ser Ala Met Gly Thr Ile Ser Ile Met Gly Asp Thr Ser
7505                7510                7515                7520

Val Ser Thr Leu Thr Pro Ala Leu Ser Asn Thr Arg Lys Ile Gln Ser
            7525                7530                7535

Glu Pro Ala Ser Ser Leu Thr Thr Arg Leu Arg Glu Thr Ser Thr Ser
            7540                7545                7550

Glu Glu Thr Ser Leu Ala Thr Glu Ala Asn Thr Val Leu Ser Lys Val
            7555                7560                7565

Ser Thr Gly Ala Thr Thr Glu Val Ser Arg Thr Glu Ala Ile Ser Phe
            7570                7575                7580

Ser Arg Thr Ser Met Ser Gly Pro Glu Gln Ser Thr Met Ser Gln Asp
7585                7590                7595                7600

Ile Ser Ile Gly Thr Ile Pro Arg Ile Ser Ala Ser Ser Val Leu Thr
            7605                7610                7615

Glu Ser Ala Lys Met Thr Ile Thr Thr Gln Thr Gly Pro Ser Glu Ser
            7620                7625                7630

Thr Leu Glu Ser Thr Leu Asn Leu Asn Thr Ala Thr Thr Pro Ser Trp
            7635                7640                7645

Val Glu Thr His Ser Ile Val Ile Gln Gly Phe Pro His Pro Glu Met
            7650                7655                7660

Thr Thr Ser Met Gly Arg Gly Pro Gly Gly Val Ser Trp Pro Ser Pro
7665                7670                7675                7680

Pro Phe Val Lys Glu Thr Ser Pro Ser Ser Pro Leu Ser Leu Pro
            7685                7690                7695

Ala Val Thr Ser Pro His Pro Val Ser Thr Thr Phe Leu Ala His Ile
            7700                7705                7710

Pro Pro Ser Pro Leu Pro Val Thr Ser Leu Leu Thr Ser Gly Pro Ala
            7715                7720                7725

Thr Thr Thr Asp Ile Leu Gly Thr Ser Thr Glu Pro Gly Thr Ser Ser
            7730                7735                7740

Ser Ser Ser Leu Ser Thr Thr Ser His Glu Arg Leu Thr Thr Tyr Lys
7745                7750                7755                7760

Asp Thr Ala His Thr Glu Ala Val His Pro Ser Thr Asn Thr Gly Gly
            7765                7770                7775

Thr Asn Val Ala Thr Thr Ser Ser Gly Tyr Lys Ser Gln Ser Ser Val
            7780                7785                7790

Leu Ala Asp Ser Ser Pro Met Cys Thr Thr Ser Thr Met Gly Asp Thr
            7795                7800                7805

Ser Val Leu Thr Ser Thr Pro Ala Phe Leu Glu Thr Arg Arg Ile Gln
            7810                7815                7820

Thr Glu Leu Ala Ser Ser Leu Thr Pro Gly Leu Arg Glu Ser Ser Gly
7825                7830                7835                7840

Ser Glu Gly Thr Ser Ser Gly Thr Lys Met Ser Thr Val Leu Ser Lys
            7845                7850                7855

Val Pro Thr Gly Ala Thr Thr Glu Ile Ser Lys Glu Asp Val Thr Ser
            7860                7865                7870

Ile Pro Gly Pro Ala Gln Ser Thr Ile Ser Pro Asp Ile Ser Thr Arg
            7875                7880                7885
```

```
Thr Val Ser Trp Phe Ser Thr Ser Pro Val Met Thr Glu Ser Ala Glu
    7890            7895                7900

Ile Thr Met Asn Thr His Thr Ser Pro Leu Gly Ala Thr Thr Gln Gly
7905            7910                7915                    7920

Thr Ser Thr Leu Ala Thr Ser Ser Thr Thr Ser Leu Thr Met Thr His
            7925                7930                7935

Ser Thr Ile Ser Gln Gly Phe Ser His Ser Gln Met Ser Thr Leu Met
            7940                7945                7950

Arg Arg Gly Pro Glu Asp Val Ser Trp Met Ser Pro Pro Leu Leu Glu
            7955                7960                7965

Lys Thr Arg Pro Ser Phe Ser Leu Met Ser Ser Pro Ala Thr Thr Ser
            7970                7975                7980

Pro Ser Pro Val Ser Ser Thr Leu Pro Glu Ser Ile Ser Ser Ser Pro
7985                7990                7995                8000

Leu Pro Val Thr Ser Leu Leu Thr Ser Gly Leu Ala Lys Thr Thr Asp
            8005                8010                8015

Met Leu His Lys Ser Ser Glu Pro Val Thr Asn Ser Pro Ala Asn Leu
            8020                8025                8030

Ser Ser Thr Ser Val Glu Ile Leu Ala Thr Ser Glu Val Thr Thr Asp
            8035                8040                8045

Thr Glu Lys Thr His Pro Ser Ser Asn Arg Thr Val Thr Asp Val Gly
            8050                8055                8060

Thr Ser Ser Ser Gly His Glu Ser Thr Ser Phe Val Leu Ala Asp Ser
8065                8070                8075                8080

Gln Thr Ser Lys Val Thr Ser Pro Met Val Ile Thr Ser Thr Met Glu
            8085                8090                8095

Asp Thr Ser Val Ser Thr Ser Thr Pro Gly Phe Phe Glu Thr Ser Arg
            8100                8105                8110

Ile Gln Thr Glu Pro Thr Ser Ser Leu Thr Leu Gly Leu Arg Lys Thr
            8115                8120                8125

Ser Ser Ser Glu Gly Thr Ser Leu Ala Thr Glu Met Ser Thr Val Leu
            8130                8135                8140

Ser Gly Val Pro Thr Gly Ala Thr Ala Glu Val Ser Arg Thr Glu Val
8145                8150                8155                8160

Thr Ser Ser Ser Arg Thr Ser Ile Ser Gly Phe Ala Gln Leu Thr Val
            8165                8170                8175

Ser Pro Glu Thr Ser Thr Glu Thr Ile Thr Arg Leu Pro Thr Ser Ser
            8180                8185                8190

Ile Met Thr Glu Ser Ala Glu Met Met Ile Lys Thr Gln Thr Asp Pro
            8195                8200                8205

Pro Gly Ser Thr Pro Glu Ser Thr His Thr Val Asp Ile Ser Thr Thr
            8210                8215                8220

Pro Asn Trp Val Glu Thr His Ser Thr Val Thr Gln Arg Phe Ser His
8225                8230                8235                8240

Ser Glu Met Thr Thr Leu Val Ser Arg Ser Pro Gly Asp Met Leu Trp
            8245                8250                8255

Pro Ser Gln Ser Ser Val Glu Glu Thr Ser Ala Ser Ser Leu Leu
            8260                8265                8270

Ser Leu Pro Ala Thr Thr Ser Pro Ser Pro Val Ser Ser Thr Leu Val
            8275                8280                8285

Glu Asp Phe Pro Ser Ala Ser Leu Pro Val Thr Ser Leu Leu Thr Pro
            8290                8295                8300

Gly Leu Val Ile Thr Thr Asp Arg Met Gly Ile Ser Arg Glu Pro Gly
```

```
                8305                8310                8315                8320
Thr Ser Ser Thr Ser Asn Leu Ser Ser Thr Ser His Glu Arg Leu Thr
                8325                8330                8335

Thr Leu Glu Asp Thr Val Asp Thr Glu Asp Met Gln Pro Ser Thr His
                8340                8345                8350

Thr Ala Val Thr Asn Val Arg Thr Ser Ile Ser Gly His Glu Ser Gln
                8355                8360                8365

Ser Ser Val Leu Ser Asp Ser Glu Thr Pro Lys Ala Thr Ser Pro Met
                8370                8375                8380

Gly Thr Thr Tyr Thr Met Gly Glu Thr Ser Val Ser Ile Ser Thr Ser
8385                8390                8395                8400

Asp Phe Phe Glu Thr Ser Arg Ile Gln Ile Glu Pro Thr Ser Ser Leu
                8405                8410                8415

Thr Ser Gly Leu Arg Glu Thr Ser Ser Ser Glu Arg Ile Ser Ser Ala
                8420                8425                8430

Thr Glu Gly Ser Thr Val Leu Ser Glu Val Pro Ser Gly Ala Thr Thr
                8435                8440                8445

Glu Val Ser Arg Thr Glu Val Ile Ser Ser Arg Gly Thr Ser Met Ser
                8450                8455                8460

Gly Pro Asp Gln Phe Thr Ile Ser Pro Asp Ile Ser Thr Glu Ala Ile
8465                8470                8475                8480

Thr Arg Leu Ser Thr Ser Pro Ile Met Thr Glu Ser Ala Glu Ser Ala
                8485                8490                8495

Ile Thr Ile Glu Thr Gly Ser Pro Gly Ala Thr Ser Glu Gly Thr Leu
                8500                8505                8510

Thr Leu Asp Thr Ser Thr Thr Thr Phe Trp Ser Gly Thr His Ser Thr
                8515                8520                8525

Ala Ser Pro Gly Phe Ser His Ser Glu Met Thr Thr Leu Met Ser Arg
                8530                8535                8540

Thr Pro Gly Asp Val Pro Trp Pro Ser Leu Pro Ser Val Glu Glu Ala
8545                8550                8555                8560

Ser Ser Val Ser Ser Leu Ser Ser Pro Ala Met Thr Ser Thr Ser
                8565                8570                8575

Phe Phe Ser Ala Leu Pro Glu Ser Ile Ser Ser Ser Pro His Pro Val
                8580                8585                8590

Thr Ala Leu Leu Thr Leu Gly Pro Val Lys Thr Thr Asp Met Leu Arg
                8595                8600                8605

Thr Ser Ser Glu Pro Glu Thr Ser Ser Pro Pro Asn Leu Ser Ser Thr
                8610                8615                8620

Ser Ala Glu Ile Leu Ala Thr Ser Glu Val Thr Lys Asp Arg Glu Lys
8625                8630                8635                8640

Ile His Pro Ser Ser Asn Thr Pro Val Val Asn Val Gly Thr Val Ile
                8645                8650                8655

Tyr Lys His Leu Ser Pro Ser Ser Val Leu Ala Asp Leu Val Thr Thr
                8660                8665                8670

Lys Pro Thr Ser Pro Met Ala Thr Thr Ser Thr Leu Gly Asn Thr Ser
                8675                8680                8685

Val Ser Thr Ser Thr Pro Ala Phe Pro Glu Thr Met Met Thr Gln Pro
                8690                8695                8700

Thr Ser Ser Leu Thr Ser Gly Leu Arg Glu Ile Ser Thr Ser Gln Glu
8705                8710                8715                8720

Thr Ser Ser Ala Thr Glu Arg Ser Ala Ser Leu Ser Gly Met Pro Thr
                8725                8730                8735
```

-continued

```
Gly Ala Thr Thr Lys Val Ser Arg Thr Glu Ala Leu Ser Leu Gly Arg
            8740                8745                8750

Thr Ser Thr Pro Gly Pro Ala Gln Ser Thr Ile Ser Pro Glu Ile Ser
        8755                8760                8765

Thr Glu Thr Ile Thr Arg Ile Ser Thr Pro Leu Thr Thr Thr Gly Ser
        8770                8775                8780

Ala Glu Met Thr Ile Thr Pro Lys Thr Gly His Ser Gly Ala Ser Ser
8785            8790                8795                8800

Gln Gly Thr Phe Thr Leu Asp Thr Ser Ser Arg Ala Ser Trp Pro Gly
            8805                8810                8815

Thr His Ser Ala Ala Thr His Arg Ser Pro His Ser Gly Met Thr Thr
            8820                8825                8830

Pro Met Ser Arg Gly Pro Glu Asp Val Ser Trp Pro Ser Arg Pro Ser
            8835                8840                8845

Val Glu Lys Thr Ser Pro Pro Ser Ser Leu Val Ser Leu Ser Ala Val
            8850                8855                8860

Thr Ser Pro Ser Pro Leu Tyr Ser Thr Pro Ser Glu Ser His Ser
8865            8870                8875                8880

Ser Pro Leu Arg Val Thr Ser Leu Phe Thr Pro Val Met Met Lys Thr
            8885                8890                8895

Thr Asp Met Leu Asp Thr Ser Leu Glu Pro Val Thr Thr Ser Pro Pro
            8900                8905                8910

Ser Met Asn Ile Thr Ser Asp Glu Ser Leu Ala Thr Ser Lys Ala Thr
            8915                8920                8925

Met Glu Thr Glu Ala Ile Gln Leu Ser Glu Asn Thr Ala Val Thr Gln
            8930                8935                8940

Met Gly Thr Ile Ser Ala Arg Gln Glu Phe Tyr Ser Ser Tyr Pro Gly
8945            8950                8955                8960

Leu Pro Glu Pro Ser Lys Val Thr Ser Pro Val Val Thr Ser Ser Thr
            8965                8970                8975

Ile Lys Asp Ile Val Ser Thr Thr Ile Pro Ala Ser Ser Glu Ile Thr
            8980                8985                8990

Arg Ile Glu Met Glu Ser Thr Ser Thr Leu Thr Pro Thr Pro Arg Glu
            8995                9000                9005

Thr Ser Thr Ser Gln Glu Ile His Ser Ala Thr Lys Pro Ser Thr Val
            9010                9015                9020

Pro Tyr Lys Ala Leu Thr Ser Ala Thr Ile Glu Asp Ser Met Thr Gln
9025            9030                9035                9040

Val Met Ser Ser Ser Arg Gly Pro Ser Pro Asp Gln Ser Thr Met Ser
            9045                9050                9055

Gln Asp Ile Ser Ser Glu Val Ile Thr Arg Leu Ser Thr Ser Pro Ile
            9060                9065                9070

Lys Ala Glu Ser Thr Glu Met Thr Ile Thr Gln Thr Gly Ser Pro
            9075                9080                9085

Gly Ala Thr Ser Arg Gly Thr Leu Thr Leu Asp Thr Ser Thr Thr Phe
            9090                9095                9100

Met Ser Gly Thr His Ser Thr Ala Ser Gln Gly Phe Ser His Ser Gln
9105            9110                9115                9120

Met Thr Ala Leu Met Ser Arg Thr Pro Gly Asp Val Pro Trp Leu Ser
            9125                9130                9135

His Pro Ser Val Glu Glu Ala Ser Ser Ala Ser Phe Ser Leu Ser Ser
            9140                9145                9150

Pro Val Met Thr Ser Ser Ser Pro Val Ser Ser Thr Leu Pro Asp Ser
            9155                9160                9165
```

```
Ile His Ser Ser Ser Leu Pro Val Thr Ser Leu Leu Thr Ser Gly Leu
    9170                9175                9180

Val Lys Thr Thr Glu Leu Leu Gly Thr Ser Ser Glu Pro Glu Thr Ser
9185                9190                9195                9200

Ser Pro Pro Asn Leu Ser Ser Thr Ser Ala Glu Ile Leu Ala Thr Thr
                9205                9210                9215

Glu Val Thr Thr Asp Thr Glu Lys Leu Glu Met Thr Asn Val Val Thr
                9220                9225                9230

Ser Gly Tyr Thr His Glu Ser Pro Ser Val Leu Ala Asp Ser Val
            9235                9240                9245

Thr Thr Lys Ala Thr Ser Ser Met Gly Ile Thr Tyr Pro Thr Gly Asp
        9250                9255                9260

Thr Asn Val Leu Thr Ser Thr Pro Ala Phe Ser Asp Thr Ser Arg Ile
9265                9270                9275                9280

Gln Thr Lys Ser Lys Leu Ser Leu Thr Pro Gly Leu Met Glu Thr Ser
                9285                9290                9295

Ile Ser Glu Glu Thr Ser Ser Ala Thr Glu Lys Ser Thr Val Leu Ser
                9300                9305                9310

Ser Val Pro Thr Gly Ala Thr Thr Glu Val Ser Arg Thr Glu Ala Ile
            9315                9320                9325

Ser Ser Ser Arg Thr Ser Ile Pro Gly Pro Ala Gln Ser Thr Met Ser
            9330                9335                9340

Ser Asp Thr Ser Met Glu Thr Ile Thr Arg Ile Ser Thr Pro Leu Thr
9345                9350                9355                9360

Arg Lys Glu Ser Thr Asp Met Ala Ile Thr Pro Lys Thr Gly Pro Ser
                9365                9370                9375

Gly Ala Thr Ser Gln Gly Thr Phe Thr Leu Asp Ser Ser Ser Thr Ala
            9380                9385                9390

Ser Trp Pro Gly Thr His Ser Ala Thr Thr Gln Arg Phe Pro Gln Ser
            9395                9400                9405

Val Val Thr Thr Pro Met Ser Arg Gly Pro Glu Asp Val Ser Trp Pro
    9410                9415                9420

Ser Pro Leu Ser Val Glu Lys Asn Ser Pro Pro Ser Ser Leu Val Ser
9425                9430                9435                9440

Ser Ser Ser Val Thr Ser Pro Ser Pro Leu Tyr Ser Thr Pro Ser Gly
                9445                9450                9455

Ser Ser His Ser Ser Pro Val Pro Val Thr Ser Leu Phe Thr Ser Ile
            9460                9465                9470

Met Met Lys Ala Thr Asp Met Leu Asp Ala Ser Leu Glu Pro Glu Thr
            9475                9480                9485

Thr Ser Ala Pro Asn Met Asn Ile Thr Ser Asp Glu Ser Leu Ala Thr
            9490                9495                9500

Ser Lys Ala Thr Glu Thr Glu Ala Ile His Val Phe Glu Asn Thr
9505                9510                9515                9520

Ala Ala Ser His Val Glu Thr Thr Ser Ala Thr Glu Glu Leu Tyr Ser
                9525                9530                9535

Ser Ser Pro Gly Phe Ser Glu Pro Thr Lys Val Ile Ser Pro Val Val
            9540                9545                9550

Thr Ser Ser Ser Ile Arg Asp Asn Met Val Ser Thr Thr Met Pro Gly
            9555                9560                9565

Ser Ser Gly Ile Thr Arg Ile Glu Ile Glu Ser Met Ser Ser Leu Thr
            9570                9575                9580

Pro Gly Leu Arg Glu Thr Arg Thr Ser Gln Asp Ile Thr Ser Ser Thr
```

```
                    9585                9590                9595                9600

Glu Thr Ser Thr Val Leu Tyr Lys Met Ser Ser Gly Ala Thr Pro Glu
                9605                9610                9615

Val Ser Arg Thr Glu Val Met Pro Ser Ser Arg Thr Ser Ile Pro Gly
                9620                9625                9630

Pro Ala Gln Ser Thr Met Ser Leu Asp Ile Ser Asp Glu Val Val Thr
                9635                9640                9645

Arg Leu Ser Thr Ser Pro Ile Met Thr Glu Ser Ala Glu Ile Thr Ile
                9650                9655                9660

Thr Thr Gln Thr Gly Tyr Ser Leu Ala Thr Ser Gln Val Thr Leu Pro
9665                9670                9675                9680

Leu Gly Thr Ser Met Thr Phe Leu Ser Gly Thr His Ser Thr Met Ser
                9685                9690                9695

Gln Gly Leu Ser His Ser Glu Met Thr Asn Leu Met Ser Arg Gly Pro
                9700                9705                9710

Glu Ser Leu Ser Trp Thr Ser Pro Arg Phe Val Glu Thr Thr Arg Ser
                9715                9720                9725

Ser Ser Ser Leu Thr Ser Leu Pro Leu Thr Thr Ser Leu Ser Pro Val
                9730                9735                9740

Ser Ser Thr Leu Leu Asp Ser Ser Pro Ser Ser Pro Leu Pro Val Thr
9745                9750                9755                9760

Ser Leu Ile Leu Pro Gly Leu Val Lys Thr Thr Glu Val Leu Asp Thr
                9765                9770                9775

Ser Ser Glu Pro Lys Thr Ser Ser Pro Asn Leu Ser Ser Thr Ser
                9780                9785                9790

Val Glu Ile Pro Ala Thr Ser Glu Ile Met Thr Asp Thr Glu Lys Ile
                9795                9800                9805

His Pro Ser Ser Asn Thr Ala Val Ala Lys Val Arg Thr Ser Ser Ser
                9810                9815                9820

Val His Glu Ser His Ser Ser Val Leu Ala Asp Ser Glu Thr Thr Ile
9825                9830                9835                9840

Thr Ile Pro Ser Met Gly Ile Thr Ser Ala Val Asp Asp Thr Thr Val
                9845                9850                9855

Phe Thr Ser Asn Pro Ala Phe Ser Glu Thr Arg Arg Ile Pro Thr Glu
                9860                9865                9870

Pro Thr Phe Ser Leu Thr Pro Gly Phe Arg Glu Thr Ser Thr Ser Glu
                9875                9880                9885

Glu Thr Thr Ser Ile Thr Glu Thr Ser Ala Val Leu Tyr Gly Val Pro
                9890                9895                9900

Thr Ser Ala Thr Thr Glu Val Ser Met Thr Glu Ile Met Ser Ser Asn
9905                9910                9915                9920

Arg Thr His Ile Pro Asp Ser Asp Gln Ser Thr Met Ser Pro Asp Ile
                9925                9930                9935

Ile Thr Glu Val Ile Thr Arg Leu Ser Ser Ser Ser Met Ser Glu
                9940                9945                9950

Ser Thr Gln Met Thr Ile Thr Thr Gln Lys Ser Ser Pro Gly Ala Thr
                9955                9960                9965

Ala Gln Ser Thr Leu Thr Leu Ala Thr Thr Ala Pro Leu Ala Arg
                9970                9975                9980

Thr His Ser Thr Val Pro Pro Arg Phe Leu His Ser Glu Met Thr
9985                9990                9995

Thr  Leu Met Ser Arg Ser  Pro Glu Asn Pro Ser  Trp Lys Ser Ser
10000               10005               10010
```

-continued

```
Pro  Phe  Val  Glu  Lys  Thr  Ser  Ser  Ser  Ser  Leu  Leu  Ser  Leu
10015               10020                    10025

Pro  Val  Thr  Thr  Ser  Pro  Ser  Val  Ser  Ser  Thr  Leu  Pro  Gln  Ser
10030               10035                    10040

Ile  Pro  Ser  Ser  Ser  Phe  Ser  Val  Thr  Ser  Leu  Leu  Thr  Pro  Gly
10045               10050                    10055

Met  Val  Lys  Thr  Thr  Asp  Thr  Ser  Thr  Glu  Pro  Gly  Thr  Ser  Leu
10060               10065                    10070

Ser  Pro  Asn  Leu  Ser  Gly  Thr  Ser  Val  Glu  Ile  Leu  Ala  Ala  Ser
10075               10080                    10085

Glu  Val  Thr  Thr  Asp  Thr  Glu  Lys  Ile  His  Pro  Ser  Ser  Ser  Met
10090               10095                    10100

Ala  Val  Thr  Asn  Val  Gly  Thr  Thr  Ser  Ser  Gly  His  Glu  Leu  Tyr
10105               10110                    10115

Ser  Ser  Val  Ser  Ile  His  Ser  Glu  Pro  Ser  Lys  Ala  Thr  Tyr  Pro
10120               10125                    10130

Val  Gly  Thr  Pro  Ser  Ser  Met  Ala  Glu  Thr  Ser  Ile  Ser  Thr  Ser
10135               10140                    10145

Met  Pro  Ala  Asn  Phe  Glu  Thr  Thr  Gly  Phe  Glu  Ala  Glu  Pro  Phe
10150               10155                    10160

Ser  His  Leu  Thr  Ser  Gly  Phe  Arg  Lys  Thr  Asn  Met  Ser  Leu  Asp
10165               10170                    10175

Thr  Ser  Ser  Val  Thr  Pro  Thr  Asn  Thr  Pro  Ser  Ser  Pro  Gly  Ser
10180               10185                    10190

Thr  His  Leu  Leu  Gln  Ser  Ser  Lys  Thr  Asp  Phe  Thr  Ser  Ser  Ala
10195               10200                    10205

Lys  Thr  Ser  Ser  Pro  Asp  Trp  Pro  Pro  Ala  Ser  Gln  Tyr  Thr  Glu
10210               10215                    10220

Ile  Pro  Val  Asp  Ile  Ile  Thr  Pro  Phe  Asn  Ala  Ser  Pro  Ser  Ile
10225               10230                    10235

Thr  Glu  Ser  Thr  Gly  Ile  Thr  Ser  Phe  Pro  Glu  Ser  Arg  Phe  Thr
10240               10245                    10250

Met  Ser  Val  Thr  Glu  Ser  Thr  His  His  Leu  Ser  Thr  Asp  Leu  Leu
10255               10260                    10265

Pro  Ser  Ala  Glu  Thr  Ile  Ser  Thr  Gly  Thr  Val  Met  Pro  Ser  Leu
10270               10275                    10280

Ser  Glu  Ala  Met  Thr  Ser  Phe  Ala  Thr  Thr  Gly  Val  Pro  Arg  Ala
10285               10290                    10295

Ile  Ser  Gly  Ser  Gly  Ser  Pro  Phe  Ser  Arg  Thr  Glu  Ser  Gly  Pro
10300               10305                    10310

Gly  Asp  Ala  Thr  Leu  Ser  Thr  Ile  Ala  Glu  Ser  Leu  Pro  Ser  Ser
10315               10320                    10325

Thr  Pro  Val  Pro  Phe  Ser  Ser  Thr  Phe  Thr  Thr  Thr  Asp  Ser
10330               10335                    10340

Ser  Thr  Ile  Pro  Ala  Leu  His  Glu  Ile  Thr  Ser  Ser  Ser  Ala  Thr
10345               10350                    10355

Pro  Tyr  Arg  Val  Asp  Thr  Ser  Leu  Gly  Thr  Glu  Ser  Ser  Thr  Thr
10360               10365                    10370

Glu  Gly  Arg  Leu  Val  Met  Val  Ser  Thr  Leu  Asp  Thr  Ser  Ser  Gln
10375               10380                    10385

Pro  Gly  Arg  Thr  Ser  Ser  Thr  Pro  Ile  Leu  Asp  Thr  Arg  Met  Thr
10390               10395                    10400

Glu  Ser  Val  Glu  Leu  Gly  Thr  Val  Thr  Ser  Ala  Tyr  Gln  Val  Pro
10405               10410                    10415
```

```
Ser  Leu  Ser  Thr  Arg  Leu  Thr  Arg  Thr  Asp  Gly  Ile  Met  Glu  His
10420          10425               10430

Ile  Thr  Lys  Ile  Pro  Asn  Glu  Ala  Ala  His  Arg  Gly  Thr  Ile  Arg
10435          10440               10445

Pro  Val  Lys  Gly  Pro  Gln  Thr  Ser  Thr  Ser  Pro  Ala  Ser  Pro  Lys
10450          10455               10460

Gly  Leu  His  Thr  Gly  Gly  Thr  Lys  Arg  Met  Glu  Thr  Thr  Thr  Thr
10465          10470               10475

Ala  Leu  Lys  Thr  Thr  Thr  Thr  Ala  Leu  Lys  Thr  Thr  Ser  Arg  Ala
10480          10485               10490

Thr  Leu  Thr  Thr  Ser  Val  Tyr  Thr  Pro  Thr  Leu  Gly  Thr  Leu  Thr
10495          10500               10505

Pro  Leu  Asn  Ala  Ser  Arg  Gln  Met  Ala  Ser  Thr  Ile  Leu  Thr  Glu
10510          10515               10520

Met  Met  Ile  Thr  Thr  Pro  Tyr  Val  Phe  Pro  Asp  Val  Pro  Glu  Thr
10525          10530               10535

Thr  Ser  Ser  Leu  Ala  Thr  Ser  Leu  Gly  Ala  Glu  Thr  Ser  Thr  Ala
10540          10545               10550

Leu  Pro  Arg  Thr  Thr  Pro  Ser  Val  Leu  Asn  Arg  Glu  Ser  Glu  Thr
10555          10560               10565

Thr  Ala  Ser  Leu  Val  Ser  Arg  Ser  Gly  Ala  Glu  Arg  Ser  Pro  Val
10570          10575               10580

Ile  Gln  Thr  Leu  Asp  Val  Ser  Ser  Ser  Glu  Pro  Asp  Thr  Thr  Ala
10585          10590               10595

Ser  Trp  Val  Ile  His  Pro  Ala  Glu  Thr  Ile  Pro  Thr  Val  Ser  Lys
10600          10605               10610

Thr  Thr  Pro  Asn  Phe  Phe  His  Ser  Glu  Leu  Asp  Thr  Val  Ser  Ser
10615          10620               10625

Thr  Ala  Thr  Ser  His  Gly  Ala  Asp  Val  Ser  Ser  Ala  Ile  Pro  Thr
10630          10635               10640

Asn  Ile  Ser  Pro  Ser  Glu  Leu  Asp  Ala  Leu  Thr  Pro  Leu  Val  Thr
10645          10650               10655

Ile  Ser  Gly  Thr  Asp  Thr  Ser  Thr  Thr  Phe  Pro  Thr  Leu  Thr  Lys
10660          10665               10670

Ser  Pro  His  Glu  Thr  Glu  Thr  Arg  Thr  Thr  Trp  Leu  Thr  His  Pro
10675          10680               10685

Ala  Glu  Thr  Ser  Ser  Thr  Ile  Pro  Arg  Thr  Ile  Pro  Asn  Phe  Ser
10690          10695               10700

His  His  Glu  Ser  Asp  Ala  Thr  Pro  Ser  Ile  Ala  Thr  Ser  Pro  Gly
10705          10710               10715

Ala  Glu  Thr  Ser  Ser  Ala  Ile  Pro  Ile  Met  Thr  Val  Ser  Pro  Gly
10720          10725               10730

Ala  Glu  Asp  Leu  Val  Thr  Ser  Gln  Val  Thr  Ser  Ser  Gly  Thr  Asp
10735          10740               10745

Arg  Asn  Met  Thr  Ile  Pro  Thr  Leu  Thr  Leu  Ser  Pro  Gly  Glu  Pro
10750          10755               10760

Lys  Thr  Ile  Ala  Ser  Leu  Val  Thr  His  Pro  Glu  Ala  Gln  Thr  Ser
10765          10770               10775

Ser  Ala  Ile  Pro  Thr  Ser  Thr  Ile  Ser  Pro  Ala  Val  Ser  Arg  Leu
10780          10785               10790

Val  Thr  Ser  Met  Val  Thr  Ser  Leu  Ala  Ala  Lys  Thr  Ser  Thr  Thr
10795          10800               10805

Asn  Arg  Ala  Leu  Thr  Asn  Ser  Pro  Gly  Glu  Pro  Ala  Thr  Thr  Val
```

```
                10810           10815           10820
Ser  Leu  Val  Thr  His  Pro  Ala  Gln  Thr  Ser  Thr  Val  Pro  Trp
10825                10830               10835

Thr  Thr  Ser  Ile  Phe  Phe  His  Ser  Lys  Ser  Asp  Thr  Thr  Pro  Ser
10840                10845               10850

Met  Thr  Thr  Ser  His  Gly  Ala  Glu  Ser  Ser  Ala  Val  Pro  Thr
10855                10860               10865

Pro  Thr  Val  Ser  Thr  Glu  Val  Pro  Gly  Val  Thr  Pro  Leu  Val
10870                10875               10880

Thr  Ser  Ser  Arg  Ala  Val  Ile  Ser  Thr  Thr  Ile  Pro  Ile  Leu  Thr
10885                10890               10895

Leu  Ser  Pro  Gly  Glu  Pro  Glu  Thr  Thr  Pro  Ser  Met  Ala  Thr  Ser
10900                10905               10910

His  Gly  Glu  Glu  Ala  Ser  Ser  Ala  Ile  Pro  Thr  Pro  Thr  Val  Ser
10915                10920               10925

Pro  Gly  Val  Pro  Gly  Val  Val  Thr  Ser  Leu  Val  Thr  Ser  Ser  Arg
10930                10935               10940

Ala  Val  Thr  Ser  Thr  Thr  Ile  Pro  Ile  Leu  Thr  Phe  Ser  Leu  Gly
10945                10950               10955

Glu  Pro  Glu  Thr  Thr  Pro  Ser  Met  Ala  Thr  Ser  His  Gly  Thr  Glu
10960                10965               10970

Ala  Gly  Ser  Ala  Val  Pro  Thr  Val  Leu  Pro  Glu  Val  Pro  Gly  Met
10975                10980               10985

Val  Thr  Ser  Leu  Val  Ala  Ser  Ser  Arg  Ala  Val  Thr  Ser  Thr  Thr
10990                10995               11000

Leu  Pro  Thr  Leu  Thr  Leu  Ser  Pro  Gly  Glu  Pro  Glu  Thr  Thr  Pro
11005                11010               11015

Ser  Met  Ala  Thr  Ser  His  Gly  Ala  Glu  Ala  Ser  Ser  Thr  Val  Pro
11020                11025               11030

Thr  Val  Ser  Pro  Glu  Val  Pro  Gly  Val  Val  Thr  Ser  Leu  Val  Thr
11035                11040               11045

Ser  Ser  Ser  Gly  Val  Asn  Ser  Thr  Ser  Ile  Pro  Thr  Leu  Ile  Leu
11050                11055               11060

Ser  Pro  Gly  Glu  Leu  Glu  Thr  Thr  Pro  Ser  Met  Ala  Thr  Ser  His
11065                11070               11075

Gly  Ala  Glu  Ala  Ser  Ser  Ala  Val  Pro  Thr  Pro  Thr  Val  Ser  Pro
11080                11085               11090

Gly  Val  Ser  Gly  Val  Val  Thr  Pro  Leu  Val  Thr  Ser  Ser  Arg  Ala
11095                11100               11105

Val  Thr  Ser  Thr  Thr  Ile  Pro  Ile  Leu  Thr  Leu  Ser  Ser  Ser  Glu
11110                11115               11120

Pro  Glu  Thr  Thr  Pro  Ser  Met  Ala  Thr  Ser  His  Gly  Val  Glu  Ala
11125                11130               11135

Ser  Ser  Ala  Val  Leu  Thr  Val  Ser  Pro  Glu  Val  Pro  Gly  Met  Val
11140                11145               11150

Thr  Ser  Leu  Val  Thr  Ser  Ser  Arg  Ala  Val  Thr  Ser  Thr  Thr  Ile
11155                11160               11165

Pro  Thr  Leu  Thr  Ile  Ser  Ser  Asp  Glu  Pro  Glu  Thr  Thr  Thr  Ser
11170                11175               11180

Leu  Val  Thr  His  Ser  Glu  Ala  Lys  Met  Ile  Ser  Ala  Ile  Pro  Thr
11185                11190               11195

Leu  Ala  Val  Ser  Pro  Thr  Val  Gln  Gly  Leu  Val  Thr  Ser  Leu  Val
11200                11205               11210
```

```
Thr  Ser  Ser  Gly  Ser  Glu  Thr  Ser  Ala  Phe  Ser  Asn  Leu  Thr  Val
11215               11220               11225

Ala  Ser  Ser  Gln  Pro  Glu  Thr  Ile  Asp  Ser  Trp  Val  Ala  His  Pro
11230               11235               11240

Gly  Thr  Glu  Ala  Ser  Ser  Val  Val  Pro  Thr  Leu  Thr  Val  Ser  Thr
11245               11250               11255

Gly  Glu  Pro  Phe  Thr  Asn  Ile  Ser  Leu  Val  Thr  His  Pro  Ala  Glu
11260               11265               11270

Ser  Ser  Ser  Thr  Leu  Pro  Arg  Thr  Thr  Ser  Arg  Phe  Ser  His  Ser
11275               11280               11285

Glu  Leu  Asp  Thr  Met  Pro  Ser  Thr  Val  Thr  Ser  Pro  Glu  Ala  Glu
11290               11295               11300

Ser  Ser  Ser  Ala  Ile  Ser  Thr  Thr  Ile  Ser  Pro  Gly  Ile  Pro  Gly
11305               11310               11315

Val  Leu  Thr  Ser  Leu  Val  Thr  Ser  Ser  Gly  Arg  Asp  Ile  Ser  Ala
11320               11325               11330

Thr  Phe  Pro  Thr  Val  Pro  Glu  Ser  Pro  His  Glu  Ser  Glu  Ala  Thr
11335               11340               11345

Ala  Ser  Trp  Val  Thr  His  Pro  Ala  Val  Thr  Ser  Thr  Thr  Val  Pro
11350               11355               11360

Arg  Thr  Thr  Pro  Asn  Tyr  Ser  His  Ser  Glu  Pro  Asp  Thr  Thr  Pro
11365               11370               11375

Ser  Ile  Ala  Thr  Ser  Pro  Gly  Ala  Glu  Ala  Thr  Ser  Asp  Phe  Pro
11380               11385               11390

Thr  Ile  Thr  Val  Ser  Pro  Asp  Val  Pro  Asp  Met  Val  Thr  Ser  Gln
11395               11400               11405

Val  Thr  Ser  Ser  Gly  Thr  Asp  Thr  Ser  Ile  Thr  Ile  Pro  Thr  Leu
11410               11415               11420

Thr  Leu  Ser  Ser  Gly  Glu  Pro  Glu  Thr  Thr  Thr  Ser  Phe  Ile  Thr
11425               11430               11435

Tyr  Ser  Glu  Thr  His  Thr  Ser  Ser  Ala  Ile  Pro  Thr  Leu  Pro  Val
11440               11445               11450

Ser  Pro  Gly  Ala  Ser  Lys  Met  Leu  Thr  Ser  Leu  Val  Ile  Ser  Ser
11455               11460               11465

Gly  Thr  Asp  Ser  Thr  Thr  Thr  Phe  Pro  Thr  Leu  Thr  Glu  Thr  Pro
11470               11475               11480

Tyr  Glu  Pro  Glu  Thr  Thr  Ala  Ile  Gln  Leu  Ile  His  Pro  Ala  Glu
11485               11490               11495

Thr  Asn  Thr  Met  Val  Pro  Lys  Thr  Thr  Pro  Lys  Phe  Ser  His  Ser
11500               11505               11510

Lys  Ser  Asp  Thr  Thr  Leu  Pro  Val  Ala  Ile  Thr  Ser  Pro  Gly  Pro
11515               11520               11525

Glu  Ala  Ser  Ser  Ala  Val  Ser  Thr  Thr  Thr  Ile  Ser  Pro  Asp  Met
11530               11535               11540

Ser  Asp  Leu  Val  Thr  Ser  Leu  Val  Pro  Ser  Ser  Gly  Thr  Asp  Thr
11545               11550               11555

Ser  Thr  Thr  Phe  Pro  Thr  Leu  Ser  Glu  Thr  Pro  Tyr  Glu  Pro  Glu
11560               11565               11570

Thr  Thr  Val  Thr  Trp  Leu  Thr  His  Pro  Ala  Glu  Thr  Ser  Thr  Thr
11575               11580               11585

Val  Ser  Gly  Thr  Ile  Pro  Asn  Phe  Ser  His  Arg  Gly  Ser  Asp  Thr
11590               11595               11600

Ala  Pro  Ser  Met  Val  Thr  Ser  Pro  Gly  Val  Asp  Thr  Arg  Ser  Gly
11605               11610               11615
```

```
Val Pro Thr Thr Thr Ile  Pro Pro Ser Ile  Pro Gly Val Val Thr
11620              11625              11630

Ser Gln Val Thr Ser  Ser Ala Thr Asp Thr  Ser Thr Ala Ile Pro
11635              11640              11645

Thr Leu Thr Pro Ser  Pro Gly Glu Pro Glu  Thr Thr Ala Ser Ser
11650              11655              11660

Ala Thr His Pro Gly  Thr Gln Thr Gly Phe  Thr Val Pro Ile Arg
11665              11670              11675

Thr Val Pro Ser Ser  Glu Pro Asp Thr Met  Ala Ser Trp Val Thr
11680              11685              11690

His Pro Pro Gln Thr  Ser Thr Pro Val Ser  Arg Thr Thr Ser Ser
11695              11700              11705

Phe Ser His Ser Ser  Pro Asp Ala Thr Pro  Val Met Ala Thr Ser
11710              11715              11720

Pro Arg Thr Glu Ala  Ser Ser Ala Val Leu  Thr Thr Ile Ser Pro
11725              11730              11735

Gly Ala Pro Glu Met  Val Thr Ser Gln Ile  Thr Ser Ser Gly Ala
11740              11745              11750

Ala Thr Ser Thr Thr  Val Pro Thr Leu Thr  His Ser Pro Gly Met
11755              11760              11765

Pro Glu Thr Thr Ala  Leu Leu Ser Thr His  Pro Arg Thr Gly Thr
11770              11775              11780

Ser Lys Thr Phe Pro  Ala Ser Thr Val Phe  Pro Gln Val Ser Glu
11785              11790              11795

Thr Thr Ala Ser Leu  Thr Ile Arg Pro Gly  Ala Glu Thr Ser Thr
11800              11805              11810

Ala Leu Pro Thr Gln  Thr Thr Ser Ser Leu  Phe Thr Leu Leu Val
11815              11820              11825

Thr Gly Thr Ser Arg  Val Asp Leu Ser Pro  Thr Ala Ser Pro Gly
11830              11835              11840

Val Ser Ala Lys Thr  Ala Pro Leu Ser Thr  His Pro Gly Thr Glu
11845              11850              11855

Thr Ser Thr Met Ile  Pro Thr Ser Thr Leu  Ser Leu Gly Leu Leu
11860              11865              11870

Glu Thr Thr Gly Leu  Leu Ala Thr Ser Ser  Ala Glu Thr Ser
11875              11880              11885

Thr Ser Thr Leu Thr  Leu Thr Val Ser Pro  Ala Val Ser Gly Leu
11890              11895              11900

Ser Ser Ala Ser Ile  Thr Thr Asp Lys Pro  Gln Thr Val Thr Ser
11905              11910              11915

Trp Asn Thr Glu Thr  Ser Pro Ser Val Thr  Val Gly Pro Pro
11920              11925              11930

Glu Phe Ser Arg Thr  Val Thr Gly Thr Thr  Met Thr Leu Ile Pro
11935              11940              11945

Ser Glu Met Pro Thr  Pro Pro Lys Thr Ser  His Gly Glu Gly Val
11950              11955              11960

Ser Pro Thr Thr Ile  Leu Arg Thr Thr Met  Val Glu Ala Thr Asn
11965              11970              11975

Leu Ala Thr Thr Gly  Ser Ser Pro Thr Val  Ala Lys Thr Thr Thr
11980              11985              11990

Thr Phe Asn Thr Leu  Ala Gly Ser Leu Phe  Thr Pro Leu Thr Thr
11995              12000              12005

Pro Gly Met Ser Thr  Leu Ala Ser Glu Ser  Val Thr Ser Arg Thr
```

-continued

```
                  12010               12015               12020
Ser  Tyr  Asn  His  Arg  Ser  Trp  Ile  Ser  Thr  Thr  Ser  Ser  Tyr  Asn
                  12025               12030               12035
Arg  Arg  Tyr  Trp  Thr  Pro  Ala  Thr  Ser  Thr  Pro  Val  Thr  Ser  Thr
                  12040               12045               12050
Phe  Ser  Pro  Gly  Ile  Ser  Thr  Ser  Ser  Ile  Pro  Ser  Ser  Thr  Ala
                  12055               12060               12065
Ala  Thr  Val  Pro  Phe  Met  Val  Pro  Phe  Thr  Leu  Asn  Phe  Thr  Ile
                  12070               12075               12080
Thr  Asn  Leu  Gln  Tyr  Glu  Glu  Asp  Met  Arg  His  Pro  Gly  Ser  Arg
                  12085               12090               12095
Lys  Phe  Asn  Ala  Thr  Glu  Arg  Glu  Leu  Gln  Gly  Leu  Leu  Lys  Pro
                  12100               12105               12110
Leu  Phe  Arg  Asn  Ser  Ser  Leu  Glu  Tyr  Leu  Tyr  Ser  Gly  Cys  Arg
                  12115               12120               12125
Leu  Ala  Ser  Leu  Arg  Pro  Glu  Lys  Asp  Ser  Ser  Ala  Met  Ala  Val
                  12130               12135               12140
Asp  Ala  Ile  Cys  Thr  His  Arg  Pro  Asp  Pro  Glu  Asp  Leu  Gly  Leu
                  12145               12150               12155
Asp  Arg  Glu  Arg  Leu  Tyr  Trp  Glu  Leu  Ser  Asn  Leu  Thr  Asn  Gly
                  12160               12165               12170
Ile  Gln  Glu  Leu  Gly  Pro  Tyr  Thr  Leu  Asp  Arg  Asn  Ser  Leu  Tyr
                  12175               12180               12185
Val  Asn  Gly  Phe  Thr  His  Arg  Ser  Ser  Met  Pro  Thr  Thr  Ser  Thr
                  12190               12195               12200
Pro  Gly  Thr  Ser  Thr  Val  Asp  Val  Gly  Thr  Ser  Gly  Thr  Pro  Ser
                  12205               12210               12215
Ser  Ser  Pro  Ser  Pro  Thr  Ala  Ala  Gly  Pro  Leu  Leu  Met  Pro  Phe
                  12220               12225               12230
Thr  Leu  Asn  Phe  Thr  Ile  Thr  Asn  Leu  Gln  Tyr  Glu  Glu  Asp  Met
                  12235               12240               12245
Arg  Arg  Thr  Gly  Ser  Arg  Lys  Phe  Asn  Thr  Met  Glu  Ser  Val  Leu
                  12250               12255               12260
Gln  Gly  Leu  Leu  Lys  Pro  Leu  Phe  Lys  Asn  Thr  Ser  Val  Gly  Pro
                  12265               12270               12275
Leu  Tyr  Ser  Gly  Cys  Arg  Leu  Thr  Leu  Leu  Arg  Pro  Glu  Lys  Asp
                  12280               12285               12290
Gly  Ala  Ala  Thr  Gly  Val  Asp  Ala  Ile  Cys  Thr  His  Arg  Leu  Asp
                  12295               12300               12305
Pro  Lys  Ser  Pro  Gly  Leu  Asn  Arg  Glu  Gln  Leu  Tyr  Trp  Glu  Leu
                  12310               12315               12320
Ser  Lys  Leu  Thr  Asn  Asp  Ile  Glu  Glu  Leu  Gly  Pro  Tyr  Thr  Leu
                  12325               12330               12335
Asp  Arg  Asn  Ser  Leu  Tyr  Val  Asn  Gly  Phe  Thr  His  Gln  Ser  Ser
                  12340               12345               12350
Val  Ser  Thr  Thr  Ser  Thr  Pro  Gly  Thr  Ser  Thr  Val  Asp  Leu  Arg
                  12355               12360               12365
Thr  Ser  Gly  Thr  Pro  Ser  Ser  Leu  Ser  Ser  Pro  Thr  Ile  Met  Ala
                  12370               12375               12380
Ala  Gly  Pro  Leu  Leu  Val  Pro  Phe  Thr  Leu  Asn  Phe  Thr  Ile  Thr
                  12385               12390               12395
Asn  Leu  Gln  Tyr  Gly  Glu  Asp  Met  Gly  His  Pro  Gly  Ser  Arg  Lys
                  12400               12405               12410
```

-continued

```
Phe Asn Thr Thr Glu Arg Val Leu Gln Gly Leu Leu Gly Pro Ile
12415               12420                   12425

Phe Lys Asn Thr Ser Val Gly Pro Leu Tyr Ser Gly Cys Arg Leu
12430               12435                   12440

Thr Ser Leu Arg Ser Glu Lys Asp Gly Ala Ala Thr Gly Val Asp
12445               12450                   12455

Ala Ile Cys Ile His His Leu Asp Pro Lys Ser Pro Gly Leu Asn
12460               12465                   12470

Arg Glu Arg Leu Tyr Trp Glu Leu Ser Gln Leu Thr Asn Gly Ile
12475               12480                   12485

Lys Glu Leu Gly Pro Tyr Thr Leu Asp Arg Asn Ser Leu Tyr Val
12490               12495                   12500

Asn Gly Phe Thr His Arg Thr Ser Val Pro Thr Thr Ser Thr Pro
12505               12510                   12515

Gly Thr Ser Thr Val Asp Leu Gly Thr Ser Gly Thr Pro Phe Ser
12520               12525                   12530

Leu Pro Ser Pro Ala Thr Ala Gly Pro Leu Leu Val Leu Phe Thr
12535               12540                   12545

Leu Asn Phe Thr Ile Thr Asn Leu Lys Tyr Glu Glu Asp Met His
12550               12555                   12560

Arg Pro Gly Ser Arg Lys Phe Asn Thr Thr Glu Arg Val Leu Gln
12565               12570                   12575

Thr Leu Leu Gly Pro Met Phe Lys Asn Thr Ser Val Gly Leu Leu
12580               12585                   12590

Tyr Ser Gly Cys Arg Leu Thr Leu Leu Arg Ser Glu Lys Asp Gly
12595               12600                   12605

Ala Ala Thr Gly Val Asp Ala Ile Cys Thr His Arg Leu Asp Pro
12610               12615                   12620

Lys Ser Pro Gly Leu Asp Arg Glu Gln Leu Tyr Trp Glu Leu Ser
12625               12630                   12635

Gln Leu Thr Asn Gly Ile Lys Glu Leu Gly Pro Tyr Thr Leu Asp
12640               12645                   12650

Arg Asn Ser Leu Tyr Val Asn Gly Phe Thr His Trp Ile Pro Val
12655               12660                   12665

Pro Thr Ser Ser Thr Pro Gly Thr Ser Thr Val Asp Leu Gly Ser
12670               12675                   12680

Gly Thr Pro Ser Ser Leu Pro Ser Pro Thr Ala Ala Gly Pro Leu
12685               12690                   12695

Leu Val Pro Phe Thr Leu Asn Phe Thr Ile Thr Asn Leu Gln Tyr
12700               12705                   12710

Glu Glu Asp Met His Pro Gly Ser Arg Lys Phe Asn Thr Thr
12715               12720                   12725

Glu Arg Val Leu Gln Gly Leu Leu Gly Pro Met Phe Lys Asn Thr
12730               12735                   12740

Ser Val Gly Leu Leu Tyr Ser Gly Cys Arg Leu Thr Leu Leu Arg
12745               12750                   12755

Ser Glu Lys Asp Gly Ala Ala Thr Gly Val Asp Ala Ile Cys Thr
12760               12765                   12770

His Arg Leu Asp Pro Lys Ser Pro Gly Val Asp Arg Glu Gln Leu
12775               12780                   12785

Tyr Trp Glu Leu Ser Gln Leu Thr Asn Gly Ile Lys Glu Leu Gly
12790               12795                   12800

Pro Tyr Thr Leu Asp Arg Asn Ser Leu Tyr Val Asn Gly Phe Thr
12805               12810                   12815
```

```
His Gln Thr Ser Ala Pro Asn Thr Ser Thr Pro Gly Thr Ser Thr
12820               12825               12830

Val Asp Leu Gly Thr Ser Gly Thr Pro Ser Ser Leu Pro Ser Pro
12835               12840               12845

Thr Ser Ala Gly Pro Leu Leu Val Pro Phe Thr Leu Asn Phe Thr
12850               12855               12860

Ile Thr Asn Leu Gln Tyr Glu Glu Asp Met Arg His Pro Gly Ser
12865               12870               12875

Arg Lys Phe Asn Thr Thr Glu Arg Val Leu Gln Gly Leu Leu Lys
12880               12885               12890

Pro Leu Phe Lys Ser Thr Ser Val Gly Pro Leu Tyr Ser Gly Cys
12895               12900               12905

Arg Leu Thr Leu Leu Arg Ser Glu Lys Asp Gly Ala Ala Thr Gly
12910               12915               12920

Val Asp Ala Ile Cys Thr His Arg Leu Asp Pro Lys Ser Pro Gly
12925               12930               12935

Val Asp Arg Glu Gln Leu Tyr Trp Glu Leu Ser Gln Leu Thr Asn
12940               12945               12950

Gly Ile Lys Glu Leu Gly Pro Tyr Thr Leu Asp Arg Asn Ser Leu
12955               12960               12965

Tyr Val Asn Gly Phe Thr His Gln Thr Ser Ala Pro Asn Thr Ser
12970               12975               12980

Thr Pro Gly Thr Ser Thr Val Asp Leu Gly Thr Ser Gly Thr Pro
12985               12990               12995

Ser Ser Leu Pro Ser Pro Thr Ser Ala Gly Pro Leu Leu Val Pro
13000               13005               13010

Phe Thr Leu Asn Phe Thr Ile Thr Asn Leu Gln Tyr Glu Glu Asp
13015               13020               13025

Met His His Pro Gly Ser Arg Lys Phe Asn Thr Thr Glu Arg Val
13030               13035               13040

Leu Gln Gly Leu Leu Gly Pro Met Phe Lys Asn Thr Ser Val Gly
13045               13050               13055

Leu Leu Tyr Ser Gly Cys Arg Leu Thr Leu Leu Arg Pro Glu Lys
13060               13065               13070

Asn Gly Ala Ala Thr Gly Met Asp Ala Ile Cys Ser His Arg Leu
13075               13080               13085

Asp Pro Lys Ser Pro Gly Leu Asn Arg Glu Gln Leu Tyr Trp Glu
13090               13095               13100

Leu Ser Gln Leu Thr His Gly Ile Lys Glu Leu Gly Pro Tyr Thr
13105               13110               13115

Leu Asp Arg Asn Ser Leu Tyr Val Asn Gly Phe Thr His Arg Ser
13120               13125               13130

Ser Val Ala Pro Thr Ser Thr Pro Gly Thr Ser Thr Val Asp Leu
13135               13140               13145

Gly Thr Ser Gly Thr Pro Ser Ser Leu Pro Ser Pro Thr Thr Ala
13150               13155               13160

Val Pro Leu Leu Val Pro Phe Thr Leu Asn Phe Thr Ile Thr Asn
13165               13170               13175

Leu Gln Tyr Gly Glu Asp Met Arg His Pro Gly Ser Arg Lys Phe
13180               13185               13190

Asn Thr Thr Glu Arg Val Leu Gln Gly Leu Gly Pro Leu Phe
13195               13200               13205

Lys Asn Ser Ser Val Gly Pro Leu Tyr Ser Gly Cys Arg Leu Ile
```

-continued

|       |       |       |       |       |       |       |       |       |       |       |       |
|-------|-------|-------|-------|-------|-------|-------|-------|-------|-------|-------|-------|
|       |       | 13210 |       |       | 13215 |       |       | 13220 |       |       |       |
| Ser   | Leu   | Arg   | Ser   | Glu   | Lys   | Asp   | Gly   | Ala   | Ala   | Thr   | Gly   | Val | Asp | Ala |

Ser Leu Arg Ser Glu Lys Asp Gly Ala Ala Thr Gly Val Asp Ala
 13225                13230                13235

Ile Cys Thr His His Leu Asn Pro Gln Ser Pro Gly Leu Asp Arg
 13240                13245                13250

Glu Gln Leu Tyr Trp Gln Leu Ser Gln Met Thr Asn Gly Ile Lys
 13255                13260                13265

Glu Leu Gly Pro Tyr Thr Leu Asp Arg Asn Ser Leu Tyr Val Asn
 13270                13275                13280

Gly Phe Thr His Arg Ser Ser Gly Leu Thr Thr Ser Thr Pro Trp
 13285                13290                13295

Thr Ser Thr Val Asp Leu Gly Thr Ser Gly Thr Pro Ser Pro Val
 13300                13305                13310

Pro Ser Pro Thr Thr Ala Gly Pro Leu Leu Val Pro Phe Thr Leu
 13315                13320                13325

Asn Phe Thr Ile Thr Asn Leu Gln Tyr Glu Glu Asp Met His Arg
 13330                13335                13340

Pro Gly Ser Arg Lys Phe Asn Thr Thr Glu Arg Val Leu Gln Gly
 13345                13350                13355

Leu Leu Ser Pro Ile Phe Lys Asn Ser Ser Val Gly Pro Leu Tyr
 13360                13365                13370

Ser Gly Cys Arg Leu Thr Ser Leu Arg Pro Glu Lys Asp Gly Ala
 13375                13380                13385

Ala Thr Gly Met Asp Ala Val Cys Leu Tyr His Pro Asn Pro Lys
 13390                13395                13400

Arg Pro Gly Leu Asp Arg Glu Gln Leu Tyr Trp Glu Leu Ser Gln
 13405                13410                13415

Leu Thr His Asn Ile Thr Glu Leu Gly Pro Tyr Ser Leu Asp Arg
 13420                13425                13430

Asp Ser Leu Tyr Val Asn Gly Phe Thr His Gln Asn Ser Val Pro
 13435                13440                13445

Thr Thr Ser Thr Pro Gly Thr Ser Thr Val Tyr Trp Ala Thr Thr
 13450                13455                13460

Gly Thr Pro Ser Ser Phe Pro Gly His Thr Glu Pro Gly Pro Leu
 13465                13470                13475

Leu Ile Pro Phe Thr Phe Asn Phe Thr Ile Thr Asn Leu His Tyr
 13480                13485                13490

Glu Glu Asn Met Gln His Pro Gly Ser Arg Lys Phe Asn Thr Thr
 13495                13500                13505

Glu Arg Val Leu Gln Gly Leu Leu Lys Pro Leu Phe Lys Asn Thr
 13510                13515                13520

Ser Val Gly Pro Leu Tyr Ser Gly Cys Arg Leu Thr Ser Leu Arg
 13525                13530                13535

Pro Glu Lys Asp Gly Ala Ala Thr Gly Met Asp Ala Val Cys Leu
 13540                13545                13550

Tyr His Pro Asn Pro Lys Arg Pro Gly Leu Asp Arg Glu Gln Leu
 13555                13560                13565

Tyr Trp Glu Leu Ser Gln Leu Thr His Asn Ile Thr Glu Leu Gly
 13570                13575                13580

Pro Tyr Ser Leu Asp Arg Asp Ser Leu Tyr Val Asn Gly Phe Thr
 13585                13590                13595

His Gln Asn Ser Val Pro Thr Thr Ser Thr Pro Gly Thr Ser Thr
 13600                13605                13610

-continued

```
Val Tyr Trp Ala Thr Thr Gly Thr Pro Ser Ser Phe Pro Gly His
13615               13620               13625

Thr Glu Pro Gly Pro Leu Leu Ile Pro Phe Thr Phe Asn Phe Thr
13630               13635               13640

Ile Thr Asn Leu His Tyr Glu Glu Asn Met Gln His Pro Gly Ser
13645               13650               13655

Arg Lys Phe Asn Thr Thr Glu Arg Val Leu Gln Gly Leu Leu Lys
13660               13665               13670

Pro Leu Phe Lys Asn Thr Ser Val Gly Pro Leu Tyr Ser Gly Cys
13675               13680               13685

Arg Leu Thr Leu Leu Arg Pro Glu Lys His Glu Ala Ala Thr Gly
13690               13695               13700

Val Asp Thr Ile Cys Thr His Arg Val Asp Pro Ile Gly Pro Gly
13705               13710               13715

Leu Asp Arg Glu Arg Leu Tyr Trp Glu Leu Ser Gln Leu Thr Asn
13720               13725               13730

Ser Ile Thr Glu Leu Gly Pro Tyr Thr Leu Asp Arg Asp Ser Leu
13735               13740               13745

Tyr Val Asn Gly Phe Asn Pro Arg Ser Ser Val Pro Thr Thr Ser
13750               13755               13760

Thr Pro Gly Thr Ser Thr Val His Leu Ala Thr Ser Gly Thr Pro
13765               13770               13775

Ser Ser Leu Pro Gly His Thr Ala Pro Val Pro Leu Leu Ile Pro
13780               13785               13790

Phe Thr Leu Asn Phe Thr Ile Thr Asn Leu His Tyr Glu Glu Asn
13795               13800               13805

Met Gln His Pro Gly Ser Arg Lys Phe Asn Thr Thr Glu Arg Val
13810               13815               13820

Leu Gln Gly Leu Leu Lys Pro Leu Phe Lys Asn Thr Ser Val Gly
13825               13830               13835

Pro Leu Tyr Ser Gly Cys Arg Leu Thr Leu Leu Arg Pro Glu Lys
13840               13845               13850

His Glu Ala Ala Thr Gly Val Asp Thr Ile Cys Thr His Arg Val
13855               13860               13865

Asp Pro Ile Gly Pro Gly Leu Glu Leu Tyr Trp Glu Leu Ser Leu
13870               13875               13880

Thr Ile Glu Leu Gly Pro Tyr Thr Leu Asp Arg Ser Leu Tyr Val
13885               13890               13895

Asn Gly Phe Thr His Ser Pro Thr Thr Ser Thr Pro Gly Thr Ser
13900               13905               13910

Thr Val Gly Thr Ser Gly Thr Pro Ser Ser Pro Thr Ser Ala Gly
13915               13920               13925

Pro Leu Leu Val Pro Phe Thr Leu Asn Phe Thr Ile Thr Asn Leu
13930               13935               13940

Gln Tyr Glu Glu Asp Met His His Pro Gly Ser Arg Lys Phe Asn
13945               13950               13955

Thr Thr Glu Arg Val Leu Gln Gly Leu Leu Gly Pro Met Phe Lys
13960               13965               13970

Asn Thr Ser Val Gly Leu Leu Tyr Ser Gly Cys Arg Leu Thr Leu
13975               13980               13985

Leu Arg Pro Glu Lys Asn Gly Ala Ala Thr Gly Met Asp Ala Ile
13990               13995               14000

Cys Ser His Arg Leu Asp Pro Lys Ser Pro Gly Leu Asp Arg Glu
14005               14010               14015
```

```
Gln Leu Tyr Trp Glu Leu Ser Gln Leu Thr His Gly Ile Lys Glu
14020               14025               14030

Leu Gly Pro Tyr Thr Leu Asp Arg Asn Ser Leu Tyr Val Asn Gly
14035               14040               14045

Phe Thr His Arg Ser Ser Val Ala Pro Thr Ser Thr Pro Gly Thr
14050               14055               14060

Ser Thr Val Asp Leu Gly Thr Ser Gly Thr Pro Ser Ser Leu Pro
14065               14070               14075

Ser Pro Thr Thr Ala Val Pro Leu Leu Val Pro Phe Thr Leu Asn
14080               14085               14090

Phe Thr Ile Thr Asn Leu Gln Tyr Gly Glu Asp Met Arg His Pro
14095               14100               14105

Gly Ser Arg Lys Phe Asn Thr Thr Glu Arg Val Leu Gln Gly Leu
14110               14115               14120

Leu Gly Pro Leu Phe Lys Asn Ser Ser Val Gly Pro Leu Tyr Ser
14125               14130               14135

Gly Cys Arg Leu Ile Ser Leu Arg Ser Glu Lys Asp Gly Ala Ala
14140               14145               14150

Thr Gly Val Asp Ala Ile Cys Thr His His Leu Asn Pro Gln Ser
14155               14160               14165

Pro Gly Leu Asp Arg Glu Gln Leu Tyr Trp Gln Leu Ser Gln Met
14170               14175               14180

Thr Asn Gly Ile Lys Glu Leu Gly Pro Tyr Thr Leu Asp Arg Asn
14185               14190               14195

Ser Leu Tyr Val Asn Gly Phe Thr His Arg Ser Ser Gly Leu Thr
14200               14205               14210

Thr Ser Thr Pro Trp Thr Ser Thr Val Asp Leu Gly Thr Ser Gly
14215               14220               14225

Thr Pro Ser Pro Val Pro Ser Pro Thr Thr Ala Gly Pro Leu Leu
14230               14235               14240

Val Pro Phe Thr Leu Asn Phe Thr Ile Thr Asn Leu Gln Tyr Glu
14245               14250               14255

Glu Asp Met His Arg Pro Gly Ser Arg Lys Phe Asn Ala Thr Glu
14260               14265               14270

Arg Val Leu Gln Gly Leu Leu Ser Pro Ile Phe Lys Asn Ser Ser
14275               14280               14285

Val Gly Pro Leu Tyr Ser Gly Cys Arg Leu Thr Ser Leu Arg Pro
14290               14295               14300

Glu Lys Asp Gly Ala Ala Thr Gly Met Asp Ala Val Cys Leu Tyr
14305               14310               14315

His Pro Asn Pro Lys Arg Pro Gly Leu Asp Arg Glu Gln Leu Tyr
14320               14325               14330

Trp Glu Leu Ser Gln Leu Thr His Asn Ile Thr Glu Leu Gly Pro
14335               14340               14345

Tyr Ser Leu Asp Arg Asp Ser Leu Tyr Val Asn Gly Phe Thr His
14350               14355               14360

Gln Ser Ser Met Thr Thr Thr Arg Thr Pro Asp Thr Ser Thr Met
14365               14370               14375

His Leu Ala Thr Ser Arg Thr Pro Ala Ser Leu Ser Gly Pro Thr
14380               14385               14390

Thr Ala Ser Pro Leu Leu Val Leu Phe Thr Ile Asn Cys Thr Ile
14395               14400               14405

Thr Asn Leu Gln Tyr Glu Glu Asp Met Arg Arg Thr Gly Ser Arg
```

-continued

```
            14410               14415               14420
Lys Phe Asn Thr Met Glu Ser Val Leu Gln Gly Leu Leu Lys Pro
14425               14430               14435
Leu Phe Lys Asn Thr Ser Val Gly Pro Leu Tyr Ser Gly Cys Arg
14440               14445               14450
Leu Thr Leu Leu Arg Pro Lys Lys Asp Gly Ala Ala Thr Gly Val
14455               14460               14465
Asp Ala Ile Cys Thr His Arg Leu Asp Pro Lys Ser Pro Gly Leu
14470               14475               14480
Asn Arg Glu Gln Leu Tyr Trp Glu Leu Ser Lys Leu Thr Asn Asp
14485               14490               14495
Ile Glu Glu Leu Gly Pro Tyr Thr Leu Asp Arg Asn Ser Leu Tyr
14500               14505               14510
Val Asn Gly Phe Thr His Gln Ser Ser Val Ser Thr Thr Ser Thr
14515               14520               14525
Pro Gly Thr Ser Thr Val Asp Leu Arg Thr Ser Gly Thr Pro Ser
14530               14535               14540
Ser Leu Ser Ser Pro Thr Ile Met Pro Leu Leu Pro Phe Thr Asn
14545               14550               14555
Thr Ile Thr Asn Leu Met Pro Gly Ser Arg Lys Phe Asn Thr Thr
14560               14565               14570
Glu Arg Val Leu Gln Gly Leu Leu Arg Pro Leu Phe Lys Asn Thr
14575               14580               14585
Ser Val Ser Ser Leu Tyr Ser Gly Cys Arg Leu Thr Leu Leu Arg
14590               14595               14600
Pro Glu Lys Asp Gly Ala Ala Thr Arg Val Asp Ala Ala Cys Thr
14605               14610               14615
Tyr Arg Pro Asp Pro Lys Ser Pro Gly Leu Asp Arg Glu Gln Leu
14620               14625               14630
Tyr Trp Glu Leu Ser Gln Leu Thr His Ser Ile Thr Glu Leu Gly
14635               14640               14645
Pro Tyr Thr Leu Asp Arg Val Ser Leu Tyr Val Asn Gly Phe Asn
14650               14655               14660
Pro Arg Ser Ser Val Pro Thr Thr Ser Thr Pro Gly Thr Ser Thr
14665               14670               14675
Val His Leu Ala Thr Ser Gly Thr Pro Ser Ser Leu Pro Gly His
14680               14685               14690
Thr Pro Leu Leu Pro Phe Thr Asn Thr Ile Thr Asn Leu Met Pro
14695               14700               14705
Gly Ser Arg Lys Phe Asn Thr Thr Glu Arg Val Leu Gln Gly Leu
14710               14715               14720
Leu Lys Pro Leu Phe Arg Asn Ser Ser Leu Glu Tyr Leu Tyr Ser
14725               14730               14735
Gly Cys Arg Leu Ala Ser Leu Arg Pro Glu Lys Asp Ser Ser Ala
14740               14745               14750
Met Ala Val Asp Ala Ile Cys Thr His Arg Pro Asp Pro Glu Asp
14755               14760               14765
Leu Gly Leu Asp Arg Glu Arg Leu Tyr Trp Glu Leu Ser Asn Leu
14770               14775               14780
Thr Asn Gly Ile Gln Glu Leu Gly Pro Tyr Thr Leu Asp Arg Asn
14785               14790               14795
Ser Leu Tyr Val Asn Gly Phe Thr His Arg Ser Ser Gly Leu Thr
14800               14805               14810
```

```
Thr  Ser  Thr  Pro  Trp  Thr  Ser  Thr  Val  Asp  Leu  Gly  Thr  Ser  Gly
14815               14820               14825

Thr  Pro  Ser  Pro  Val  Pro  Ser  Pro  Thr  Ala  Gly  Pro  Leu  Leu
14830               14835               14840

Val  Pro  Phe  Thr  Leu  Asn  Phe  Thr  Ile  Thr  Asn  Leu  Gln  Tyr  Glu
14845               14850               14855

Glu  Asp  Met  His  Arg  Pro  Gly  Ser  Arg  Arg  Phe  Asn  Thr  Thr  Glu
14860               14865               14870

Arg  Val  Leu  Gln  Gly  Leu  Leu  Thr  Pro  Leu  Phe  Lys  Asn  Thr  Ser
14875               14880               14885

Val  Gly  Pro  Leu  Tyr  Ser  Gly  Cys  Arg  Leu  Thr  Leu  Leu  Arg  Pro
14890               14895               14900

Glu  Lys  Gln  Glu  Ala  Ala  Thr  Gly  Val  Asp  Thr  Ile  Cys  Thr  His
14905               14910               14915

Arg  Val  Asp  Pro  Ile  Gly  Pro  Gly  Leu  Asp  Arg  Glu  Arg  Leu  Tyr
14920               14925               14930

Trp  Glu  Leu  Ser  Gln  Leu  Thr  Asn  Ser  Ile  Thr  Glu  Leu  Gly  Pro
14935               14940               14945

Tyr  Thr  Leu  Asp  Arg  Asp  Ser  Leu  Tyr  Val  Asn  Gly  Phe  Asn  Pro
14950               14955               14960

Trp  Ser  Ser  Val  Pro  Thr  Thr  Ser  Thr  Pro  Gly  Thr  Ser  Thr  Val
14965               14970               14975

His  Leu  Ala  Thr  Ser  Gly  Thr  Pro  Ser  Ser  Leu  Pro  Gly  His  Thr
14980               14985               14990

Ala  Pro  Val  Pro  Leu  Leu  Ile  Pro  Phe  Thr  Leu  Asn  Phe  Thr  Ile
14995               15000               15005

Thr  Asp  Leu  His  Tyr  Glu  Glu  Asn  Met  Gln  His  Pro  Gly  Ser  Arg
15010               15015               15020

Lys  Phe  Asn  Thr  Thr  Glu  Arg  Val  Leu  Gln  Gly  Leu  Leu  Lys  Pro
15025               15030               15035

Leu  Phe  Lys  Ser  Thr  Ser  Val  Gly  Pro  Leu  Tyr  Ser  Gly  Cys  Arg
15040               15045               15050

Leu  Thr  Leu  Leu  Arg  Pro  Glu  Lys  His  Gly  Ala  Ala  Thr  Gly  Val
15055               15060               15065

Asp  Ala  Ile  Cys  Thr  Leu  Arg  Leu  Asp  Pro  Thr  Gly  Pro  Gly  Leu
15070               15075               15080

Asp  Arg  Glu  Arg  Leu  Tyr  Trp  Glu  Leu  Ser  Gln  Leu  Thr  Asn  Ser
15085               15090               15095

Val  Thr  Glu  Leu  Gly  Pro  Tyr  Thr  Leu  Asp  Arg  Asp  Ser  Leu  Tyr
15100               15105               15110

Val  Asn  Gly  Phe  Thr  His  Arg  Ser  Ser  Val  Pro  Thr  Thr  Ser  Ile
15115               15120               15125

Pro  Gly  Thr  Ser  Ala  Val  His  Leu  Glu  Thr  Ser  Gly  Thr  Pro  Ala
15130               15135               15140

Ser  Leu  Pro  Gly  His  Thr  Ala  Pro  Gly  Pro  Leu  Leu  Val  Pro  Phe
15145               15150               15155

Thr  Leu  Asn  Phe  Thr  Ile  Thr  Asn  Leu  Gln  Tyr  Glu  Glu  Asp  Met
15160               15165               15170

Arg  His  Pro  Gly  Ser  Arg  Lys  Phe  Ser  Thr  Thr  Glu  Arg  Val  Leu
15175               15180               15185

Gln  Gly  Leu  Leu  Lys  Pro  Leu  Phe  Lys  Asn  Thr  Ser  Val  Ser  Ser
15190               15195               15200

Leu  Tyr  Ser  Gly  Cys  Arg  Leu  Thr  Leu  Leu  Arg  Pro  Glu  Lys  Asp
15205               15210               15215
```

| | | | | | | | | | | |
|---|---|---|---|---|---|---|---|---|---|---|
|Gly|Ala|Ala|Thr|Arg|Val|Asp|Ala|Val|Cys|Thr|His|Arg|Pro|Asp|
|15220| | | |15225| | | |15230| | | | | | |

Gly Ala Ala Thr Arg Val Asp Ala Val Cys Thr His Arg Pro Asp
15220              15225              15230

Pro Lys Ser Pro Gly Leu Asp Arg Glu Arg Leu Tyr Trp Lys Leu
15235              15240              15245

Ser Gln Leu Thr His Gly Ile Thr Glu Leu Gly Pro Tyr Thr Leu
15250              15255              15260

Asp Arg His Ser Leu Tyr Val Asn Gly Phe Thr His Gln Ser Ser
15265              15270              15275

Met Thr Thr Thr Arg Thr Pro Asp Thr Ser Thr Met His Leu Ala
15280              15285              15290

Thr Ser Arg Thr Pro Ala Ser Leu Ser Gly Pro Thr Thr Ala Ser
15295              15300              15305

Pro Leu Leu Val Leu Phe Thr Ile Asn Phe Thr Ile Thr Asn Leu
15310              15315              15320

Arg Tyr Glu Glu Asn Met His His Pro Gly Ser Arg Lys Phe Asn
15325              15330              15335

Thr Thr Glu Arg Val Leu Gln Gly Leu Leu Arg Pro Val Phe Lys
15340              15345              15350

Asn Thr Ser Val Gly Pro Leu Tyr Ser Gly Cys Arg Leu Thr Thr
15355              15360              15365

Leu Arg Pro Lys Lys Asp Gly Ala Ala Thr Lys Val Asp Ala Ile
15370              15375              15380

Cys Thr Tyr Arg Pro Asp Pro Lys Ser Pro Gly Leu Asp Arg Glu
15385              15390              15395

Gln Leu Tyr Trp Glu Leu Ser Gln Leu Thr His Ser Ile Thr Glu
15400              15405              15410

Leu Gly Pro Tyr Thr Gln Asp Arg Asp Ser Leu Tyr Val Asn Gly
15415              15420              15425

Phe Thr His Arg Ser Ser Val Pro Thr Thr Ser Ile Pro Gly Thr
15430              15435              15440

Ser Ala Val His Leu Glu Thr Ser Gly Thr Pro Ala Ser Leu Pro
15445              15450              15455

Gly His Thr Ala Pro Gly Pro Leu Leu Val Pro Phe Thr Leu Asn
15460              15465              15470

Phe Thr Ile Thr Asn Leu Gln Tyr Glu Glu Asp Met Arg His Pro
15475              15480              15485

Gly Ser Arg Lys Phe Asn Thr Thr Glu Arg Val Leu Gln Gly Leu
15490              15495              15500

Leu Lys Pro Leu Phe Lys Ser Thr Ser Val Gly Pro Leu Tyr Ser
15505              15510              15515

Gly Cys Arg Leu Thr Leu Leu Arg Pro Glu Lys Arg Gly Ala Ala
15520              15525              15530

Thr Gly Val Asp Thr Ile Cys Thr His Arg Leu Asp Pro Leu Asn
15535              15540              15545

Pro Gly Leu Asp Arg Glu Gln Leu Tyr Trp Glu Leu Ser Lys Leu
15550              15555              15560

Thr Arg Gly Ile Ile Glu Leu Gly Pro Tyr Leu Leu Asp Arg Gly
15565              15570              15575

Ser Leu Tyr Val Asn Gly Phe Thr His Arg Thr Ser Val Pro Thr
15580              15585              15590

Thr Ser Thr Pro Gly Thr Ser Thr Val Asp Leu Gly Thr Ser Gly
15595              15600              15605

Thr Pro Phe Ser Leu Pro Ser Pro Ala Pro Leu Leu Pro Phe Thr

-continued

```
            15610               15615               15620

Asn  Thr  Ile  Thr  Asn  Leu  Met  Pro  Gly  Ser  Arg  Lys  Phe  Asn  Thr
            15625               15630               15635

Thr  Glu  Arg  Val  Leu  Gln  Thr  Leu  Leu  Gly  Pro  Met  Phe  Lys  Asn
            15640               15645               15650

Thr  Ser  Val  Gly  Leu  Leu  Tyr  Ser  Gly  Cys  Arg  Leu  Thr  Leu  Leu
            15655               15660               15665

Arg  Ser  Glu  Lys  Asp  Gly  Ala  Ala  Thr  Gly  Val  Asp  Ala  Ile  Cys
            15670               15675               15680

Thr  His  Arg  Leu  Asp  Pro  Lys  Ser  Pro  Gly  Val  Asp  Arg  Glu  Gln
            15685               15690               15695

Leu  Tyr  Trp  Glu  Leu  Ser  Gln  Leu  Thr  Asn  Gly  Ile  Lys  Glu  Leu
            15700               15705               15710

Gly  Pro  Tyr  Thr  Leu  Asp  Arg  Asn  Ser  Leu  Tyr  Val  Asn  Gly  Phe
            15715               15720               15725

Thr  His  Trp  Ile  Pro  Val  Pro  Thr  Ser  Ser  Thr  Pro  Gly  Thr  Ser
            15730               15735               15740

Thr  Val  Asp  Leu  Gly  Ser  Gly  Thr  Pro  Ser  Ser  Leu  Pro  Ser  Pro
            15745               15750               15755

Thr  Thr  Ala  Gly  Pro  Leu  Leu  Val  Pro  Phe  Thr  Leu  Asn  Phe  Thr
            15760               15765               15770

Ile  Thr  Asn  Leu  Lys  Tyr  Glu  Glu  Asp  Met  His  Cys  Pro  Gly  Ser
            15775               15780               15785

Arg  Lys  Phe  Asn  Thr  Thr  Glu  Arg  Val  Leu  Gln  Ser  Leu  Leu  Gly
            15790               15795               15800

Pro  Met  Phe  Lys  Asn  Thr  Ser  Val  Gly  Pro  Leu  Tyr  Ser  Gly  Cys
            15805               15810               15815

Arg  Leu  Thr  Leu  Leu  Arg  Ser  Glu  Lys  Asp  Gly  Ala  Ala  Thr  Gly
            15820               15825               15830

Val  Asp  Ala  Ile  Cys  Thr  His  Arg  Leu  Asp  Pro  Lys  Ser  Pro  Gly
            15835               15840               15845

Val  Asp  Arg  Glu  Gln  Leu  Tyr  Trp  Glu  Leu  Ser  Gln  Leu  Thr  Asn
            15850               15855               15860

Gly  Ile  Lys  Glu  Leu  Gly  Pro  Tyr  Thr  Leu  Asp  Arg  Asn  Ser  Leu
            15865               15870               15875

Tyr  Val  Asn  Gly  Phe  Thr  His  Gln  Thr  Ser  Ala  Pro  Asn  Thr  Ser
            15880               15885               15890

Thr  Pro  Gly  Thr  Ser  Thr  Val  Asp  Leu  Gly  Thr  Ser  Gly  Thr  Pro
            15895               15900               15905

Ser  Ser  Leu  Pro  Ser  Pro  Thr  Pro  Leu  Leu  Pro  Phe  Thr  Asn  Thr
            15910               15915               15920

Ile  Thr  Asn  Leu  Met  Pro  Gly  Ser  Arg  Lys  Phe  Asn  Thr  Thr  Glu
            15925               15930               15935

Val  Leu  Gln  Gly  Leu  Leu  Pro  Phe  Lys  Asn  Ser  Val  Gly  Leu  Tyr
            15940               15945               15950

Ser  Gly  Cys  Arg  Leu  Thr  Leu  Arg  Glu  Lys  Gly  Ala  Ala  Thr  Gly
            15955               15960               15965

Asp  Ala  Ile  Cys  His  Pro  Lys  Pro  Gly  Leu  Glu  Leu  Tyr  Trp  Glu
            15970               15975               15980

Leu  Ser  Leu  Thr  Ile  Glu  Leu  Gly  Pro  Tyr  Thr  Leu  Asp  Arg  Ser
            15985               15990               15995

Leu  Tyr  Val  Asn  Gly  Phe  Thr  His  Trp  Ile  Pro  Val  Pro  Thr  Ser
            16000               16005               16010
```

-continued

```
Ser  Thr  Pro  Gly  Thr  Ser  Thr  Val  Asp  Leu  Gly  Ser  Gly  Thr  Pro
16015               16020               16025

Ser  Ser  Leu  Pro  Ser  Pro  Thr  Thr  Ala  Gly  Pro  Leu  Leu  Val  Pro
16030               16035               16040

Phe  Thr  Leu  Asn  Phe  Thr  Ile  Thr  Asn  Leu  Lys  Tyr  Glu  Glu  Asp
16045               16050               16055

Met  His  Cys  Pro  Gly  Ser  Arg  Lys  Phe  Asn  Thr  Thr  Glu  Arg  Val
16060               16065               16070

Leu  Gln  Ser  Leu  Leu  Gly  Pro  Met  Phe  Lys  Asn  Thr  Ser  Val  Gly
16075               16080               16085

Pro  Leu  Tyr  Ser  Gly  Cys  Arg  Leu  Thr  Ser  Leu  Arg  Ser  Glu  Lys
16090               16095               16100

Asp  Gly  Ala  Ala  Thr  Gly  Val  Asp  Ala  Ile  Cys  Thr  His  Arg  Val
16105               16110               16115

Asp  Pro  Lys  Ser  Pro  Gly  Val  Asp  Arg  Glu  Gln  Leu  Tyr  Trp  Glu
16120               16125               16130

Leu  Ser  Gln  Leu  Thr  Asn  Gly  Ile  Lys  Glu  Leu  Gly  Pro  Tyr  Thr
16135               16140               16145

Leu  Asp  Arg  Asn  Ser  Leu  Tyr  Val  Asn  Gly  Phe  Thr  His  Gln  Thr
16150               16155               16160

Ser  Ala  Pro  Asn  Thr  Ser  Thr  Pro  Gly  Thr  Ser  Thr  Val  Gly  Thr
16165               16170               16175

Ser  Gly  Thr  Pro  Ser  Ser  Pro  Thr  Ser  Ala  Gly  Pro  Leu  Leu  Val
16180               16185               16190

Pro  Phe  Thr  Leu  Asn  Phe  Thr  Ile  Thr  Asn  Leu  Gln  Tyr  Glu  Glu
16195               16200               16205

Asp  Met  His  His  Pro  Gly  Ser  Arg  Lys  Phe  Asn  Thr  Thr  Glu  Arg
16210               16215               16220

Val  Leu  Gln  Gly  Leu  Leu  Gly  Pro  Met  Phe  Lys  Asn  Thr  Ser  Val
16225               16230               16235

Gly  Leu  Leu  Tyr  Ser  Gly  Cys  Arg  Leu  Thr  Leu  Leu  Arg  Pro  Glu
16240               16245               16250

Lys  Asn  Gly  Ala  Thr  Thr  Gly  Met  Asp  Ala  Ile  Cys  Thr  His  Arg
16255               16260               16265

Leu  Asp  Pro  Lys  Ser  Pro  Gly  Leu  Glu  Leu  Tyr  Trp  Glu  Leu  Ser
16270               16275               16280

Leu  Thr  Ile  Glu  Leu  Gly  Pro  Tyr  Thr  Leu  Asp  Arg  Ser  Leu  Tyr
16285               16290               16295

Val  Asn  Gly  Phe  Thr  His  Ser  Pro  Thr  Thr  Ser  Thr  Pro  Gly  Thr
16300               16305               16310

Ser  Thr  Val  Gly  Thr  Ser  Gly  Thr  Pro  Ser  Ser  Pro  Thr  Pro  Leu
16315               16320               16325

Leu  Pro  Phe  Thr  Asn  Thr  Ile  Thr  Asn  Leu  Met  Pro  Gly  Ser  Arg
16330               16335               16340

Lys  Phe  Asn  Thr  Thr  Glu  Arg  Val  Leu  Gln  Gly  Leu  Leu  Lys  Pro
16345               16350               16355

Leu  Phe  Arg  Asn  Ser  Ser  Leu  Glu  Tyr  Leu  Tyr  Ser  Gly  Cys  Arg
16360               16365               16370

Leu  Ala  Ser  Leu  Arg  Pro  Glu  Lys  Asp  Ser  Ser  Ala  Met  Ala  Val
16375               16380               16385

Asp  Ala  Ile  Cys  Thr  His  Arg  Pro  Asp  Pro  Glu  Asp  Leu  Gly  Leu
16390               16395               16400

Asp  Arg  Glu  Arg  Leu  Tyr  Trp  Glu  Leu  Ser  Asn  Leu  Thr  Asn  Gly
16405               16410               16415
```

```
Ile Gln Glu Leu Gly Pro Tyr Thr Leu Asp Arg Asn Ser Leu Tyr
16420              16425              16430

Val Asn Gly Phe Thr His Arg Ser Ser Met Pro Thr Thr Ser Thr
16435              16440              16445

Pro Gly Thr Ser Thr Val Asp Val Gly Thr Ser Gly Thr Pro Ser
16450              16455              16460

Ser Ser Pro Ser Pro Thr Thr Ala Gly Pro Leu Leu Ile Pro Phe
16465              16470              16475

Thr Leu Asn Phe Thr Ile Thr Asn Leu Gln Tyr Gly Glu Asp Met
16480              16485              16490

Gly His Pro Gly Ser Arg Lys Phe Asn Thr Glu Arg Val Leu
16495              16500              16505

Gln Gly Leu Leu Gly Pro Ile Phe Lys Asn Thr Ser Val Gly Pro
16510              16515              16520

Leu Tyr Ser Gly Cys Arg Leu Thr Ser Leu Arg Ser Glu Lys Asp
16525              16530              16535

Gly Ala Ala Thr Gly Val Asp Ala Ile Cys Ile His His Leu Asp
16540              16545              16550

Pro Lys Ser Pro Gly Leu Asn Arg Glu Arg Leu Tyr Trp Glu Leu
16555              16560              16565

Ser Gln Leu Thr Asn Gly Ile Lys Glu Leu Gly Pro Tyr Thr Leu
16570              16575              16580

Asp Arg Asn Ser Leu Tyr Val Asn Gly Phe Thr His Arg Thr Ser
16585              16590              16595

Val Pro Thr Thr Ser Thr Pro Gly Thr Ser Val Asp Leu Gly
16600              16605              16610

Thr Ser Gly Thr Pro Phe Ser Leu Pro Ser Pro Ala Thr Ala Gly
16615              16620              16625

Pro Leu Leu Val Leu Phe Thr Leu Asn Phe Thr Ile Thr Asn Leu
16630              16635              16640

Lys Tyr Glu Glu Asp Met His Arg Pro Gly Ser Arg Lys Phe Asn
16645              16650              16655

Thr Thr Glu Arg Val Leu Gln Thr Leu Leu Gly Pro Met Phe Lys
16660              16665              16670

Asn Thr Ser Val Gly Leu Leu Tyr Ser Gly Cys Arg Leu Thr Leu
16675              16680              16685

Leu Arg Ser Glu Lys Asp Gly Ala Ala Thr Gly Val Asp Ala Ile
16690              16695              16700

Cys Thr His Arg Leu Asp Pro Lys Ser Pro Gly Leu Glu Leu Tyr
16705              16710              16715

Trp Glu Leu Ser Leu Thr Ile Glu Leu Gly Pro Tyr Thr Leu Asp
16720              16725              16730

Arg Ser Leu Tyr Val Asn Gly Phe Thr His Ser Pro Thr Thr Ser
16735              16740              16745

Thr Pro Gly Thr Ser Thr Val Gly Thr Ser Gly Thr Pro Ser Ser
16750              16755              16760

Pro Thr Pro Leu Leu Pro Phe Thr Asn Thr Ile Thr Asn Leu Met
16765              16770              16775

Pro Gly Ser Arg Lys Phe Asn Thr Thr Glu Arg Val Leu Gln Gly
16780              16785              16790

Leu Leu Arg Pro Val Phe Lys Asn Thr Ser Val Gly Pro Leu Tyr
16795              16800              16805

Ser Gly Cys Arg Leu Thr Leu Leu Arg Pro Lys Lys Asp Gly Ala
```

-continued

```
        16810           16815           16820

Ala  Thr  Lys  Val  Asp  Ala  Ile  Cys  Thr  Tyr  Arg  Pro  Asp  Pro  Lys
16825           16830           16835

Ser  Pro  Gly  Leu  Asp  Arg  Glu  Gln  Leu  Tyr  Trp  Glu  Leu  Ser  Gln
16840           16845           16850

Leu  Thr  His  Ser  Ile  Thr  Glu  Leu  Gly  Pro  Tyr  Thr  Gln  Asp  Arg
16855           16860           16865

Asp  Ser  Leu  Tyr  Val  Asn  Gly  Phe  Thr  Arg  Ser  Ser  Val  Pro
16870           16875           16880

Thr  Thr  Ser  Ile  Pro  Gly  Thr  Ser  Ala  Val  His  Leu  Glu  Thr  Thr
16885           16890           16895

Gly  Thr  Pro  Ser  Ser  Phe  Pro  Gly  His  Thr  Glu  Pro  Gly  Pro  Leu
16900           16905           16910

Leu  Ile  Pro  Phe  Thr  Phe  Asn  Phe  Thr  Ile  Thr  Asn  Leu  Arg  Tyr
16915           16920           16925

Glu  Glu  Asn  Met  Gln  His  Pro  Gly  Ser  Arg  Lys  Phe  Asn  Thr  Thr
16930           16935           16940

Glu  Arg  Val  Leu  Gln  Gly  Leu  Leu  Thr  Pro  Leu  Phe  Lys  Asn  Thr
16945           16950           16955

Ser  Val  Gly  Pro  Leu  Tyr  Ser  Gly  Cys  Arg  Leu  Thr  Leu  Leu  Arg
16960           16965           16970

Pro  Glu  Lys  Gln  Glu  Ala  Ala  Thr  Gly  Val  Asp  Thr  Ile  Cys  Thr
16975           16980           16985

His  Arg  Val  Asp  Pro  Ile  Gly  Pro  Gly  Leu  Asp  Arg  Glu  Arg  Leu
16990           16995           17000

Tyr  Trp  Glu  Leu  Ser  Gln  Leu  Thr  Asn  Ser  Ile  Thr  Glu  Leu  Gly
17005           17010           17015

Pro  Tyr  Thr  Leu  Asp  Arg  Asp  Ser  Leu  Tyr  Val  Asp  Gly  Phe  Asn
17020           17025           17030

Pro  Trp  Ser  Ser  Val  Pro  Thr  Thr  Ser  Thr  Pro  Gly  Thr  Ser  Thr
17035           17040           17045

Val  His  Leu  Ala  Thr  Ser  Gly  Thr  Pro  Ser  Pro  Leu  Pro  Gly  His
17050           17055           17060

Thr  Ala  Pro  Val  Pro  Leu  Leu  Ile  Pro  Phe  Thr  Leu  Asn  Phe  Thr
17065           17070           17075

Ile  Thr  Asp  Leu  His  Tyr  Glu  Glu  Asn  Met  Gln  His  Pro  Gly  Ser
17080           17085           17090

Arg  Lys  Phe  Asn  Thr  Thr  Glu  Arg  Val  Leu  Gln  Gly  Leu  Leu  Lys
17095           17100           17105

Pro  Leu  Phe  Lys  Ser  Thr  Ser  Val  Gly  Pro  Leu  Tyr  Ser  Gly  Cys
17110           17115           17120

Arg  Leu  Thr  Leu  Leu  Arg  Pro  Glu  Lys  His  Gly  Ala  Ala  Thr  Gly
17125           17130           17135

Val  Asp  Ala  Ile  Cys  Thr  Leu  Arg  Leu  Asp  Pro  Thr  Gly  Pro  Gly
17140           17145           17150

Leu  Asp  Arg  Glu  Arg  Leu  Tyr  Trp  Glu  Leu  Ser  Gln  Leu  Thr  Asn
17155           17160           17165

Ser  Ile  Thr  Glu  Leu  Gly  Pro  Tyr  Thr  Leu  Asp  Arg  Asp  Ser  Leu
17170           17175           17180

Tyr  Val  Asn  Gly  Phe  Asn  Pro  Trp  Ser  Ser  Val  Pro  Thr  Thr  Ser
17185           17190           17195

Thr  Pro  Gly  Thr  Ser  Thr  Val  His  Leu  Ala  Thr  Ser  Gly  Thr  Pro
17200           17205           17210
```

-continued

```
Ser  Ser  Leu  Pro  Gly  His  Thr  Thr  Ala  Gly  Pro  Leu  Leu  Val  Pro
17215               17220                    17225

Phe  Thr  Leu  Asn  Phe  Thr  Ile  Thr  Asn  Leu  Lys  Tyr  Glu  Glu  Asp
17230               17235                    17240

Met  His  Cys  Pro  Gly  Ser  Arg  Lys  Phe  Asn  Thr  Thr  Glu  Arg  Val
17245               17250                    17255

Leu  Gln  Ser  Leu  His  Gly  Pro  Met  Phe  Lys  Asn  Thr  Ser  Val  Gly
17260               17265                    17270

Pro  Leu  Tyr  Ser  Gly  Cys  Arg  Leu  Thr  Leu  Arg  Ser  Glu  Lys
17275               17280                    17285

Asp  Gly  Ala  Ala  Thr  Gly  Val  Asp  Ala  Ile  Cys  Thr  His  Arg  Leu
17290               17295                    17300

Asp  Pro  Lys  Ser  Pro  Gly  Leu  Glu  Leu  Tyr  Trp  Glu  Leu  Ser  Leu
17305               17310                    17315

Thr  Ile  Glu  Leu  Gly  Pro  Tyr  Thr  Leu  Asp  Arg  Ser  Leu  Tyr  Val
17320               17325                    17330

Asn  Gly  Phe  Thr  His  Ser  Pro  Thr  Thr  Ser  Thr  Pro  Gly  Thr  Ser
17335               17340                    17345

Thr  Val  Gly  Thr  Ser  Gly  Thr  Pro  Ser  Ser  Pro  Thr  Pro  Leu  Leu
17350               17355                    17360

Pro  Phe  Thr  Asn  Thr  Ile  Thr  Asn  Leu  Met  Pro  Gly  Ser  Arg  Lys
17365               17370                    17375

Phe  Asn  Thr  Thr  Glu  Val  Leu  Gln  Gly  Leu  Leu  Pro  Phe  Lys  Asn
17380               17385                    17390

Ser  Val  Gly  Leu  Tyr  Ser  Gly  Cys  Arg  Leu  Thr  Leu  Arg  Glu  Lys
17395               17400                    17405

Gly  Ala  Ala  Thr  Gly  Asp  Ala  Ile  Cys  His  Pro  Lys  Pro  Gly  Leu
17410               17415                    17420

Glu  Leu  Tyr  Trp  Glu  Leu  Ser  Leu  Thr  Asn  Ser  Ile  Thr  Glu  Leu
17425               17430                    17435

Gly  Pro  Tyr  Thr  Leu  Asp  Arg  Asp  Ser  Leu  Tyr  Val  Asn  Gly  Phe
17440               17445                    17450

Thr  His  Arg  Ser  Ser  Met  Pro  Thr  Thr  Ser  Ile  Pro  Gly  Thr  Ser
17455               17460                    17465

Ala  Val  His  Leu  Glu  Thr  Ser  Gly  Thr  Pro  Ala  Ser  Leu  Pro  Gly
17470               17475                    17480

His  Thr  Ala  Pro  Gly  Pro  Leu  Leu  Val  Pro  Phe  Thr  Leu  Asn  Phe
17485               17490                    17495

Thr  Ile  Thr  Asn  Leu  Gln  Tyr  Glu  Glu  Asp  Met  Arg  His  Pro  Gly
17500               17505                    17510

Ser  Arg  Lys  Phe  Asn  Thr  Thr  Glu  Arg  Val  Leu  Gln  Gly  Leu  Leu
17515               17520                    17525

Lys  Pro  Leu  Phe  Lys  Ser  Thr  Ser  Val  Gly  Pro  Leu  Tyr  Ser  Gly
17530               17535                    17540

Cys  Arg  Leu  Thr  Leu  Leu  Arg  Pro  Glu  Lys  Arg  Gly  Ala  Ala  Thr
17545               17550                    17555

Gly  Val  Asp  Thr  Ile  Cys  Thr  His  Arg  Leu  Asp  Pro  Leu  Asn  Pro
17560               17565                    17570

Gly  Leu  Glu  Leu  Tyr  Trp  Glu  Leu  Ser  Leu  Thr  Ile  Glu  Leu  Gly
17575               17580                    17585

Pro  Tyr  Thr  Leu  Asp  Arg  Ser  Leu  Tyr  Val  Asn  Gly  Phe  Thr  His
17590               17595                    17600

Ser  Pro  Thr  Thr  Ser  Thr  Pro  Gly  Thr  Ser  Thr  Val  Gly  Thr  Ser
17605               17610                    17615
```

-continued

```
Gly Thr Pro Ser Ser Pro Thr Pro Leu Leu Pro Phe Thr Asn Thr
17620               17625               17630

Ile Thr Asn Leu Met Pro Gly Ser Arg Lys Phe Asn Thr Thr Glu
17635               17640               17645

Val Leu Gln Gly Leu Leu Pro Phe Lys Asn Ser Val Gly Leu Tyr
17650               17655               17660

Ser Gly Cys Arg Leu Thr Leu Arg Glu Lys Gly Ala Ala Thr Gly
17665               17670               17675

Asp Ala Ile Cys His Pro Lys Pro Gly Leu Glu Leu Tyr Trp Glu
17680               17685               17690

Leu Ser Leu Thr Ile Glu Leu Gly Pro Tyr Thr Leu Asp Arg Ser
17695               17700               17705

Leu Tyr Val Asn Gly Phe His Pro Arg Ser Ser Val Pro Thr Thr
17710               17715               17720

Ser Thr Pro Gly Thr Ser Thr Val His Leu Ala Thr Ser Gly Thr
17725               17730               17735

Pro Ser Ser Leu Pro Gly His Thr Ala Pro Val Pro Leu Leu Ile
17740               17745               17750

Pro Phe Thr Leu Asn Phe Thr Ile Thr Asn Leu His Tyr Glu Glu
17755               17760               17765

Asn Met Gln His Pro Gly Ser Arg Lys Phe Asn Thr Thr Glu Arg
17770               17775               17780

Val Leu Gln Gly Leu Leu Gly Pro Met Phe Lys Asn Thr Ser Val
17785               17790               17795

Gly Leu Leu Tyr Ser Gly Cys Arg Leu Thr Leu Leu Arg Pro Glu
17800               17805               17810

Lys Asn Gly Ala Ala Thr Gly Met Asp Ala Ile Cys Ser His Arg
17815               17820               17825

Leu Asp Pro Lys Ser Pro Gly Leu Glu Leu Tyr Trp Glu Leu Ser
17830               17835               17840

Leu Thr Ile Glu Leu Gly Pro Tyr Thr Leu Asp Arg Ser Leu Tyr
17845               17850               17855

Val Asn Gly Phe Thr His Ser Pro Thr Thr Ser Thr Pro Gly Thr
17860               17865               17870

Ser Thr Val Gly Thr Ser Gly Thr Pro Ser Ser Pro Thr Pro Leu
17875               17880               17885

Leu Pro Phe Thr Asn Thr Ile Thr Asn Leu Met Pro Gly Ser Arg
17890               17895               17900

Lys Phe Asn Thr Thr Glu Val Leu Gln Gly Leu Leu Pro Phe Lys
17905               17910               17915

Asn Ser Val Gly Leu Tyr Ser Gly Cys Arg Leu Thr Leu Arg Glu
17920               17925               17930

Lys Gly Ala Ala Thr Gly Asp Ala Ile Cys His Pro Lys Pro Gly
17935               17940               17945

Leu Glu Leu Tyr Trp Glu Leu Ser Leu Thr Ile Glu Leu Gly Pro
17950               17955               17960

Tyr Thr Leu Asp Arg Ser Leu Tyr Val Asn Gly Phe Thr His Gln
17965               17970               17975

Asn Ser Val Pro Thr Thr Ser Thr Pro Gly Thr Ser Thr Val Tyr
17980               17985               17990

Trp Ala Thr Thr Gly Thr Pro Ser Ser Phe Pro Gly His Thr Glu
17995               18000               18005

Pro Gly Pro Leu Leu Ile Pro Phe Thr Phe Asn Phe Thr Ile Thr
```

-continued

```
                  18010               18015                18020

Asn  Leu His Tyr Glu  Glu  Asn Met Gln  His Pro  Gly Ser Arg Lys
18025                 18030               18035

Phe  Asn Thr Thr Glu  Arg  Val Leu Gln  Gly Leu  Leu Thr Pro Leu
18040                 18045               18050

Phe  Lys Asn Thr Ser  Val  Gly Pro Leu  Tyr Ser  Gly Cys Arg Leu
18055                 18060               18065

Thr  Leu Leu Arg Pro  Glu  Lys Gln Glu  Ala Ala  Thr Gly Val Asp
18070                 18075               18080

Thr  Ile Cys Thr His  Arg  Val Asp Pro  Ile Gly  Pro Gly Leu Glu
18085                 18090               18095

Leu  Tyr Trp Glu Leu  Ser  Leu Thr Ile  Glu Leu  Gly Pro Tyr Thr
18100                 18105               18110

Leu  Asp Arg Ser Leu  Tyr  Val Asn Gly  Phe Thr  His Ser Pro Thr
18115                 18120               18125

Thr  Ser Thr Pro Gly  Thr  Ser Thr Val  Gly Thr  Ser Gly Thr Pro
18130                 18135               18140

Ser  Ser Pro Thr Pro  Leu  Leu Pro Phe  Thr Asn  Thr Ile Thr Asn
18145                 18150               18155

Leu  Met Pro Gly Ser  Arg  Lys Phe Asn  Thr Thr  Glu Val Leu Gln
18160                 18165               18170

Gly  Leu Leu Pro Phe  Lys  Asn Ser Val  Gly Leu  Tyr Ser Gly Cys
18175                 18180               18185

Arg  Leu Thr Leu Arg  Glu  Lys Gly Ala  Ala Thr  Gly Asp Ala Ile
18190                 18195               18200

Cys  His Pro Lys Pro  Gly  Leu Glu Leu  Tyr Trp  Glu Leu Ser Leu
18205                 18210               18215

Thr  Ile Glu Leu Gly  Pro  Tyr Thr Leu  Asp Arg  Ser Leu Tyr Val
18220                 18225               18230

Asn  Gly Phe Thr His  Arg  Ser Ser Val  Pro Thr  Thr Ser Ser Pro
18235                 18240               18245

Gly  Thr Ser Thr Val  His  Leu Ala Thr  Ser Gly  Thr Pro Ser Ser
18250                 18255               18260

Leu  Pro Gly His Thr  Ala  Pro Val Pro  Leu Leu  Ile Pro Phe Thr
18265                 18270               18275

Leu  Asn Phe Thr Ile  Thr  Asn Leu His  Tyr Glu  Glu Asn Met Gln
18280                 18285               18290

His  Pro Gly Ser Arg  Lys  Phe Asn Thr  Thr Glu  Arg Val Leu Gln
18295                 18300               18305

Gly  Leu Leu Lys Pro  Leu  Phe Lys Ser  Thr Ser  Val Gly Pro Leu
18310                 18315               18320

Tyr  Ser Gly Cys Arg  Leu  Thr Leu Leu  Arg Pro  Glu Lys His Gly
18325                 18330               18335

Ala  Ala Thr Gly Val  Asp  Ala Ile Cys  Thr Leu  Arg Leu Asp Pro
18340                 18345               18350

Thr  Gly Pro Gly Leu  Glu  Leu Tyr Trp  Glu Leu  Ser Leu Thr Ile
18355                 18360               18365

Glu  Leu Gly Pro Tyr  Thr  Leu Asp Arg  Ser Leu  Tyr Val Asn Gly
18370                 18375               18380

Phe  Thr His Ser Pro  Thr  Thr Ser Thr  Pro Gly  Thr Ser Thr Val
18385                 18390               18395

Gly  Thr Ser Gly Thr  Pro  Ser Ser Pro  Thr Pro  Leu Leu Pro Phe
18400                 18405               18410
```

-continued

```
Thr  Asn  Thr  Ile  Thr  Asn  Leu  Met  Pro  Gly  Ser  Arg  Lys  Phe  Asn
18415               18420                    18425

Thr  Thr  Glu  Val  Leu  Gln  Gly  Leu  Leu  Pro  Phe  Lys  Asn  Ser  Val
18430               18435                    18440

Gly  Leu  Tyr  Ser  Gly  Cys  Arg  Leu  Thr  Leu  Arg  Glu  Lys  Gly  Ala
18445               18450                    18455

Ala  Thr  Gly  Asp  Ala  Ile  Cys  His  Pro  Lys  Pro  Gly  Leu  Glu  Leu
18460               18465                    18470

Tyr  Trp  Glu  Leu  Ser  Leu  Thr  Ile  Glu  Leu  Gly  Pro  Tyr  Thr  Leu
18475               18480                    18485

Asp  Arg  Ser  Leu  Tyr  Val  Asn  Gly  Phe  Thr  His  Arg  Thr  Ser  Val
18490               18495                    18500

Pro  Thr  Thr  Ser  Thr  Pro  Gly  Thr  Ser  Thr  Val  His  Leu  Ala  Thr
18505               18510                    18515

Ser  Gly  Thr  Pro  Ser  Ser  Leu  Pro  Gly  His  Thr  Ala  Pro  Val  Pro
18520               18525                    18530

Leu  Leu  Ile  Pro  Phe  Thr  Leu  Asn  Phe  Thr  Ile  Thr  Asn  Leu  Gln
18535               18540                    18545

Tyr  Glu  Glu  Asp  Met  His  Arg  Pro  Gly  Ser  Arg  Lys  Phe  Asn  Thr
18550               18555                    18560

Thr  Glu  Arg  Val  Leu  Gln  Gly  Leu  Leu  Ser  Pro  Ile  Phe  Lys  Asn
18565               18570                    18575

Ser  Ser  Val  Gly  Pro  Leu  Tyr  Ser  Gly  Cys  Arg  Leu  Thr  Ser  Leu
18580               18585                    18590

Arg  Pro  Glu  Lys  Asp  Gly  Ala  Ala  Thr  Gly  Met  Asp  Ala  Val  Cys
18595               18600                    18605

Leu  Tyr  His  Pro  Asn  Pro  Lys  Arg  Pro  Gly  Leu  Asp  Arg  Glu  Gln
18610               18615                    18620

Leu  Tyr  Cys  Glu  Leu  Ser  Gln  Leu  Thr  His  Asn  Ile  Thr  Glu  Leu
18625               18630                    18635

Gly  Pro  Tyr  Ser  Leu  Asp  Arg  Asp  Ser  Leu  Tyr  Val  Asn  Gly  Phe
18640               18645                    18650

Thr  His  Gln  Asn  Ser  Val  Pro  Thr  Thr  Ser  Thr  Pro  Gly  Thr  Ser
18655               18660                    18665

Thr  Val  Tyr  Trp  Ala  Thr  Thr  Gly  Thr  Pro  Ser  Ser  Phe  Pro  Gly
18670               18675                    18680

His  Thr  Pro  Leu  Leu  Pro  Phe  Thr  Asn  Thr  Ile  Thr  Asn  Leu  Met
18685               18690                    18695

Pro  Gly  Ser  Arg  Lys  Phe  Asn  Thr  Thr  Glu  Val  Leu  Gln  Gly  Leu
18700               18705                    18710

Leu  Pro  Phe  Lys  Asn  Ser  Val  Gly  Leu  Tyr  Ser  Gly  Cys  Arg  Leu
18715               18720                    18725

Thr  Leu  Arg  Glu  Lys  Gly  Ala  Ala  Thr  Gly  Asp  Ala  Ile  Cys  His
18730               18735                    18740

Pro  Lys  Pro  Gly  Leu  Glu  Leu  Tyr  Trp  Glu  Leu  Ser  Leu  Thr  Ile
18745               18750                    18755

Glu  Leu  Gly  Pro  Tyr  Thr  Leu  Asp  Arg  Ser  Leu  Tyr  Val  Asn  Gly
18760               18765                    18770

Phe  Thr  His  Trp  Ser  Ser  Gly  Leu  Thr  Ser  Thr  Pro  Trp  Thr
18775               18780                    18785

Ser  Thr  Val  Asp  Leu  Gly  Thr  Ser  Gly  Thr  Pro  Ser  Pro  Val  Pro
18790               18795                    18800

Ser  Pro  Thr  Thr  Ala  Gly  Pro  Leu  Leu  Val  Pro  Phe  Thr  Leu  Asn
18805               18810                    18815
```

```
Phe Thr Ile Thr Asn Leu Gln Tyr Glu Glu Asp Met His Arg Pro
18820               18825               18830

Gly Ser Arg Lys Phe Asn Ala Thr Glu Arg Val Leu Gln Gly Leu
18835               18840               18845

Leu Ser Pro Ile Phe Lys Asn Thr Ser Val Gly Pro Leu Tyr Ser
18850               18855               18860

Gly Cys Arg Leu Thr Leu Leu Arg Pro Glu Lys Gln Glu Ala Ala
18865               18870               18875

Thr Gly Val Asp Thr Ile Cys Thr His Arg Val Asp Pro Ile Gly
18880               18885               18890

Pro Gly Leu Glu Leu Tyr Trp Glu Leu Ser Leu Thr Ile Glu Leu
18895               18900               18905

Gly Pro Tyr Thr Leu Asp Arg Ser Leu Tyr Val Asn Gly Phe Thr
18910               18915               18920

His Ser Pro Thr Thr Ser Thr Pro Gly Thr Ser Thr Val Gly Thr
18925               18930               18935

Ser Gly Thr Pro Ser Ser Pro Thr Pro Leu Leu Pro Phe Thr Asn
18940               18945               18950

Thr Ile Thr Asn Leu Met Pro Gly Ser Arg Lys Phe Asn Thr Thr
18955               18960               18965

Glu Val Leu Gln Gly Leu Leu Pro Phe Lys Asn Ser Val Gly Leu
18970               18975               18980

Tyr Ser Gly Cys Arg Leu Thr Leu Arg Glu Lys Gly Ala Ala Thr
18985               18990               18995

Gly Asp Ala Ile Cys His Pro Lys Pro Gly Leu Glu Leu Tyr Trp
19000               19005               19010

Glu Leu Ser Leu Thr Ile Glu Leu Gly Pro Tyr Thr Leu Asp Arg
19015               19020               19025

Ser Leu Tyr Val Asn Gly Phe Thr His Arg Ser Phe Gly Leu Thr
19030               19035               19040

Thr Ser Thr Pro Trp Thr Ser Thr Val Asp Leu Gly Thr Ser Gly
19045               19050               19055

Thr Pro Ser Pro Val Pro Ser Pro Thr Ala Gly Pro Leu Leu
19060               19065               19070

Val Pro Phe Thr Leu Asn Phe Thr Ile Thr Asn Leu Gln Tyr Glu
19075               19080               19085

Glu Asp Met His Arg Pro Gly Ser Arg Lys Phe Asn Thr Thr Glu
19090               19095               19100

Arg Val Leu Gln Gly Leu Leu Thr Pro Leu Phe Arg Asn Thr Ser
19105               19110               19115

Val Ser Ser Leu Tyr Ser Gly Cys Arg Leu Thr Leu Leu Arg Pro
19120               19125               19130

Glu Lys Asp Gly Ala Ala Thr Arg Val Asp Ala Val Cys Thr His
19135               19140               19145

Arg Pro Asp Pro Lys Ser Pro Gly Leu Glu Leu Tyr Trp Glu Leu
19150               19155               19160

Ser Leu Thr Ile Glu Leu Gly Pro Tyr Thr Leu Asp Arg Ser Leu
19165               19170               19175

Tyr Val Asn Gly Phe Thr His Ser Pro Thr Thr Ser Thr Pro Gly
19180               19185               19190

Thr Ser Thr Val Gly Thr Ser Gly Thr Pro Ser Ser Pro Thr Pro
19195               19200               19205

Leu Leu Pro Phe Thr Asn Thr Ile Thr Asn Leu Met Pro Gly Ser
```

-continued

```
            19210                19215                19220

Arg  Lys  Phe  Asn  Thr  Thr  Glu  Val  Leu  Gln  Gly  Leu  Leu  Pro  Phe
            19225                19230                19235

Lys  Asn  Ser  Val  Gly  Leu  Tyr  Ser  Gly  Cys  Arg  Leu  Thr  Leu  Arg
            19240                19245                19250

Glu  Lys  Gly  Ala  Ala  Thr  Gly  Asp  Ala  Ile  Cys  His  Pro  Lys  Pro
            19255                19260                19265

Gly  Leu  Glu  Leu  Tyr  Trp  Glu  Leu  Ser  Leu  Thr  Ile  Glu  Leu  Gly
            19270                19275                19280

Pro  Tyr  Thr  Leu  Asp  Arg  Ser  Leu  Tyr  Val  Asn  Gly  Phe  Thr  His
            19285                19290                19295

Trp  Ile  Pro  Val  Pro  Thr  Ser  Ser  Thr  Pro  Gly  Thr  Ser  Thr  Val
            19300                19305                19310

Asp  Leu  Gly  Ser  Gly  Thr  Pro  Ser  Ser  Leu  Pro  Ser  Pro  Thr  Thr
            19315                19320                19325

Ala  Gly  Pro  Leu  Leu  Val  Pro  Phe  Thr  Leu  Asn  Phe  Thr  Ile  Thr
            19330                19335                19340

Asn  Leu  Gln  Tyr  Gly  Glu  Asp  Met  Gly  His  Pro  Gly  Ser  Arg  Lys
            19345                19350                19355

Phe  Asn  Thr  Thr  Glu  Arg  Val  Leu  Gln  Gly  Leu  Leu  Gly  Pro  Ile
            19360                19365                19370

Phe  Lys  Asn  Thr  Ser  Val  Gly  Pro  Leu  Tyr  Ser  Gly  Cys  Arg  Leu
            19375                19380                19385

Thr  Ser  Leu  Arg  Ser  Glu  Lys  Asp  Gly  Ala  Ala  Thr  Gly  Val  Asp
            19390                19395                19400

Ala  Ile  Cys  Ile  His  His  Leu  Asp  Pro  Lys  Ser  Pro  Gly  Leu  Glu
            19405                19410                19415

Leu  Tyr  Trp  Glu  Leu  Ser  Leu  Thr  Ile  Glu  Leu  Gly  Pro  Tyr  Thr
            19420                19425                19430

Leu  Asp  Arg  Ser  Leu  Tyr  Val  Asn  Gly  Phe  Thr  His  Ser  Pro  Thr
            19435                19440                19445

Thr  Ser  Thr  Pro  Gly  Thr  Ser  Thr  Val  Gly  Thr  Ser  Gly  Thr  Pro
            19450                19455                19460

Ser  Ser  Pro  Thr  Pro  Leu  Leu  Pro  Phe  Thr  Asn  Thr  Ile  Thr  Asn
            19465                19470                19475

Leu  Met  Pro  Gly  Ser  Arg  Lys  Phe  Asn  Thr  Thr  Glu  Val  Leu  Gln
            19480                19485                19490

Gly  Leu  Leu  Pro  Phe  Lys  Asn  Ser  Val  Gly  Leu  Tyr  Ser  Gly  Cys
            19495                19500                19505

Arg  Leu  Thr  Leu  Arg  Glu  Lys  Gly  Ala  Ala  Thr  Gly  Asp  Ala  Ile
            19510                19515                19520

Cys  His  Pro  Lys  Pro  Gly  Leu  Glu  Leu  Tyr  Trp  Glu  Leu  Ser  Leu
            19525                19530                19535

Thr  Ile  Glu  Leu  Gly  Pro  Tyr  Thr  Leu  Asp  Arg  Ser  Leu  Tyr  Val
            19540                19545                19550

Asn  Gly  Phe  Thr  His  Gln  Thr  Phe  Ala  Pro  Asn  Thr  Ser  Thr  Pro
            19555                19560                19565

Gly  Thr  Ser  Thr  Val  Asp  Leu  Gly  Thr  Ser  Gly  Thr  Pro  Ser  Ser
            19570                19575                19580

Leu  Pro  Ser  Pro  Thr  Ser  Ala  Gly  Pro  Leu  Leu  Val  Pro  Phe  Thr
            19585                19590                19595

Leu  Asn  Phe  Thr  Ile  Thr  Asn  Leu  Gln  Tyr  Glu  Glu  Asp  Met  His
            19600                19605                19610
```

```
His  Pro  Gly  Ser  Arg  Lys  Phe  Asn  Thr  Thr  Glu  Arg  Val  Leu  Gln
19615               19620                    19625

Gly  Leu  Leu  Gly  Pro  Met  Phe  Lys  Asn  Thr  Ser  Val  Gly  Leu  Leu
19630               19635                    19640

Tyr  Ser  Gly  Cys  Arg  Leu  Thr  Leu  Leu  Arg  Pro  Glu  Lys  Asn  Gly
19645               19650                    19655

Ala  Ala  Thr  Arg  Val  Asp  Ala  Val  Cys  Thr  His  Arg  Pro  Asp  Pro
19660               19665                    19670

Lys  Ser  Pro  Gly  Leu  Glu  Leu  Tyr  Trp  Glu  Leu  Ser  Leu  Thr  Ile
19675               19680                    19685

Glu  Leu  Gly  Pro  Tyr  Thr  Leu  Asp  Arg  Ser  Leu  Tyr  Val  Asn  Gly
19690               19695                    19700

Phe  Thr  His  Ser  Pro  Thr  Thr  Ser  Thr  Pro  Gly  Thr  Ser  Thr  Val
19705               19710                    19715

Gly  Thr  Ser  Gly  Thr  Pro  Ser  Ser  Pro  Thr  Ala  Pro  Val  Pro  Leu
19720               19725                    19730

Leu  Ile  Pro  Phe  Thr  Leu  Asn  Phe  Thr  Ile  Thr  Asn  Leu  His  Tyr
19735               19740                    19745

Glu  Glu  Asn  Met  Gln  His  Pro  Gly  Ser  Arg  Lys  Phe  Asn  Thr  Thr
19750               19755                    19760

Glu  Arg  Val  Leu  Gln  Gly  Leu  Leu  Lys  Pro  Leu  Phe  Lys  Ser  Thr
19765               19770                    19775

Ser  Val  Gly  Pro  Leu  Tyr  Ser  Gly  Cys  Arg  Leu  Thr  Leu  Leu  Arg
19780               19785                    19790

Pro  Glu  Lys  His  Gly  Ala  Ala  Thr  Gly  Val  Asp  Ala  Ile  Cys  Thr
19795               19800                    19805

Leu  Arg  Leu  Asp  Pro  Thr  Gly  Pro  Gly  Leu  Asp  Arg  Glu  Arg  Leu
19810               19815                    19820

Tyr  Trp  Glu  Leu  Ser  Gln  Leu  Thr  Asn  Ser  Val  Thr  Glu  Leu  Gly
19825               19830                    19835

Pro  Tyr  Thr  Leu  Asp  Arg  Asp  Ser  Leu  Tyr  Val  Asn  Gly  Phe  Thr
19840               19845                    19850

Gln  Arg  Ser  Ser  Val  Pro  Thr  Thr  Ser  Ile  Pro  Gly  Thr  Ser  Ala
19855               19860                    19865

Val  His  Leu  Glu  Thr  Ser  Gly  Thr  Pro  Ala  Ser  Leu  Pro  Gly  His
19870               19875                    19880

Thr  Ala  Pro  Gly  Pro  Leu  Leu  Val  Pro  Phe  Thr  Leu  Asn  Phe  Thr
19885               19890                    19895

Ile  Thr  Asn  Leu  Gln  Tyr  Glu  Val  Asp  Met  Arg  His  Pro  Gly  Ser
19900               19905                    19910

Arg  Lys  Phe  Asn  Thr  Thr  Glu  Arg  Val  Leu  Gln  Gly  Leu  Leu  Lys
19915               19920                    19925

Pro  Leu  Phe  Lys  Ser  Thr  Ser  Val  Gly  Pro  Leu  Tyr  Ser  Gly  Cys
19930               19935                    19940

Arg  Leu  Thr  Leu  Leu  Arg  Pro  Glu  Lys  Arg  Gly  Ala  Ala  Thr  Gly
19945               19950                    19955

Val  Asp  Thr  Ile  Cys  Thr  His  Arg  Leu  Asp  Pro  Leu  Asn  Pro  Gly
19960               19965                    19970

Leu  Asp  Arg  Glu  Gln  Leu  Tyr  Trp  Glu  Leu  Ser  Lys  Leu  Thr  Arg
19975               19980                    19985

Gly  Ile  Ile  Glu  Leu  Gly  Pro  Tyr  Leu  Leu  Asp  Arg  Gly  Ser  Leu
19990               19995                    20000

Tyr  Val  Asn  Gly  Phe  Thr  His  Arg  Asn  Phe  Val  Pro  Ile  Thr  Ser
20005               20010                    20015
```

```
Thr  Pro  Gly  Thr  Ser  Thr  Val  His  Leu  Gly  Ser  Glu  Thr  Pro
20020               20025                    20030

Ser  Ser  Leu  Pro  Arg  Pro  Ile  Val  Pro  Gly  Pro  Leu  Leu  Val  Pro
20035               20040                    20045

Phe  Thr  Leu  Asn  Phe  Thr  Ile  Thr  Asn  Leu  Gln  Tyr  Glu  Glu  Ala
20050               20055                    20060

Met  Arg  His  Pro  Gly  Ser  Arg  Lys  Phe  Asn  Thr  Thr  Glu  Arg  Val
20065               20070                    20075

Leu  Gln  Gly  Leu  Leu  Arg  Pro  Leu  Phe  Lys  Asn  Thr  Ser  Ile  Gly
20080               20085                    20090

Pro  Leu  Tyr  Ser  Ser  Cys  Arg  Leu  Thr  Leu  Leu  Arg  Pro  Glu  Lys
20095               20100                    20105

Asp  Lys  Ala  Ala  Thr  Arg  Val  Asp  Ala  Ile  Cys  Thr  His  His  Pro
20110               20115                    20120

Asp  Pro  Gln  Ser  Pro  Gly  Leu  Asn  Arg  Glu  Gln  Leu  Tyr  Trp  Glu
20125               20130                    20135

Leu  Ser  Gln  Leu  Thr  His  Gly  Ile  Thr  Glu  Leu  Gly  Pro  Tyr  Thr
20140               20145                    20150

Leu  Asp  Arg  Asp  Ser  Leu  Tyr  Val  Asp  Gly  Phe  Thr  His  Trp  Ser
20155               20160                    20165

Pro  Ile  Pro  Thr  Thr  Ser  Thr  Pro  Gly  Thr  Ser  Ile  Val  Asn  Leu
20170               20175                    20180

Gly  Thr  Ser  Gly  Ile  Pro  Pro  Ser  Leu  Pro  Glu  Thr  Thr  Pro  Leu
20185               20190                    20195

Leu  Pro  Phe  Thr  Asn  Thr  Ile  Thr  Asn  Leu  Met  Pro  Gly  Ser  Arg
20200               20205                    20210

Lys  Phe  Asn  Thr  Thr  Glu  Arg  Val  Leu  Gln  Gly  Leu  Leu  Lys  Pro
20215               20220                    20225

Leu  Phe  Lys  Ser  Thr  Ser  Val  Gly  Pro  Leu  Tyr  Ser  Gly  Cys  Arg
20230               20235                    20240

Leu  Thr  Leu  Leu  Arg  Pro  Glu  Lys  Asp  Gly  Val  Ala  Thr  Arg  Val
20245               20250                    20255

Asp  Ala  Ile  Cys  Thr  His  Arg  Pro  Asp  Pro  Lys  Ile  Pro  Gly  Leu
20260               20265                    20270

Asp  Arg  Gln  Gln  Leu  Tyr  Trp  Glu  Leu  Ser  Gln  Leu  Thr  His  Ser
20275               20280                    20285

Ile  Thr  Glu  Leu  Gly  Pro  Tyr  Thr  Leu  Asp  Arg  Asp  Ser  Leu  Tyr
20290               20295                    20300

Val  Asn  Gly  Phe  Thr  Gln  Arg  Ser  Ser  Val  Pro  Thr  Thr  Ser  Thr
20305               20310                    20315

Pro  Gly  Thr  Phe  Thr  Val  Gln  Pro  Glu  Thr  Ser  Glu  Thr  Pro  Ser
20320               20325                    20330

Ser  Leu  Pro  Gly  Pro  Thr  Ala  Thr  Gly  Pro  Val  Leu  Leu  Pro  Phe
20335               20340                    20345

Thr  Leu  Asn  Phe  Thr  Ile  Thr  Asn  Leu  Gln  Tyr  Glu  Glu  Asp  Met
20350               20355                    20360

His  Arg  Pro  Gly  Ser  Arg  Lys  Phe  Asn  Thr  Thr  Glu  Arg  Val  Leu
20365               20370                    20375

Gln  Gly  Leu  Leu  Met  Pro  Leu  Phe  Lys  Asn  Thr  Ser  Val  Ser  Ser
20380               20385                    20390

Leu  Tyr  Ser  Gly  Cys  Arg  Leu  Thr  Leu  Leu  Arg  Pro  Glu  Lys  Asp
20395               20400                    20405

Gly  Ala  Ala  Thr  Arg  Val  Asp  Ala  Val  Cys  Thr  His  Arg  Pro  Asp
```

```
                20410               20415               20420

Pro Lys Ser Pro Gly Leu Asp Arg Glu Arg Leu Tyr Trp Lys Leu
20425               20430               20435

Ser Gln Leu Thr His Gly Ile Thr Glu Leu Gly Pro Tyr Thr Leu
20440               20445               20450

Asp Arg His Ser Leu Tyr Val Asn Gly Phe Thr His Gln Ser Ser
20455               20460               20465

Met Thr Thr Thr Arg Thr Pro Asp Thr Ser Thr Met His Leu Ala
20470               20475               20480

Thr Ser Arg Thr Pro Ala Ser Leu Ser Gly Pro Thr Thr Ala Ser
20485               20490               20495

Pro Leu Leu Val Leu Phe Thr Ile Asn Phe Thr Ile Thr Asn Leu
20500               20505               20510

Arg Tyr Glu Glu Asn Met His His Pro Gly Ser Arg Lys Phe Asn
20515               20520               20525

Thr Thr Glu Arg Val Leu Gln Gly Leu Leu Arg Pro Val Phe Lys
20530               20535               20540

Asn Thr Ser Val Gly Pro Leu Tyr Ser Gly Cys Arg Leu Thr Leu
20545               20550               20555

Leu Arg Pro Lys Lys Asp Gly Ala Ala Thr Lys Val Asp Ala Ile
20560               20565               20570

Cys Thr Tyr Arg Pro Asp Pro Lys Ser Pro Gly Leu Asp Arg Glu
20575               20580               20585

Gln Leu Tyr Trp Glu Leu Ser Gln Leu Thr His Ser Ile Thr Glu
20590               20595               20600

Leu Gly Pro Tyr Thr Leu Asp Arg Asp Ser Leu Tyr Val Asn Gly
20605               20610               20615

Phe Thr Gln Arg Ser Ser Val Pro Thr Thr Ser Ile Pro Gly Thr
20620               20625               20630

Pro Thr Val Asp Leu Gly Thr Ser Gly Thr Pro Val Ser Lys Pro
20635               20640               20645

Gly Pro Ser Ala Ala Ser Pro Leu Leu Val Leu Phe Thr Leu Asn
20650               20655               20660

Phe Thr Ile Thr Asn Leu Arg Tyr Glu Glu Asn Met Gln His Pro
20665               20670               20675

Gly Ser Arg Lys Phe Asn Thr Thr Glu Arg Val Leu Gln Gly Leu
20680               20685               20690

Leu Arg Ser Leu Phe Lys Ser Thr Ser Val Gly Pro Leu Tyr Ser
20695               20700               20705

Gly Cys Arg Leu Thr Leu Leu Arg Pro Glu Lys Asp Gly Thr Ala
20710               20715               20720

Thr Gly Val Asp Ala Ile Cys Thr His His Pro Asp Pro Lys Ser
20725               20730               20735

Pro Arg Leu Asp Arg Glu Gln Leu Tyr Trp Glu Leu Ser Gln Leu
20740               20745               20750

Thr His Asn Ile Thr Glu Leu Gly His Tyr Ala Leu Asp Asn Asp
20755               20760               20765

Ser Leu Phe Val Asn Gly Phe Thr His Arg Ser Ser Val Ser Thr
20770               20775               20780

Thr Ser Thr Pro Gly Thr Pro Thr Val Tyr Leu Gly Ala Ser Lys
20785               20790               20795

Thr Pro Ala Ser Ile Phe Gly Pro Ser Ala Ala Ser His Leu Leu
20800               20805               20810
```

-continued

Ile Leu Phe Thr Leu Asn Phe Thr Ile Thr Asn Leu Arg Tyr Glu
20815                 20820             20825

Glu Asn Met Trp Pro Gly Ser Arg Lys Phe Asn Thr Thr Glu Arg
20830                 20835             20840

Val Leu Gln Gly Leu Leu Arg Pro Leu Phe Lys Asn Thr Ser Val
20845                 20850             20855

Gly Pro Leu Tyr Ser Gly Ser Arg Leu Thr Leu Leu Arg Pro Glu
20860                 20865             20870

Lys Asp Gly Glu Ala Thr Gly Val Asp Ala Ile Cys Thr His Arg
20875                 20880             20885

Pro Asp Pro Thr Gly Pro Gly Leu Asp Arg Glu Gln Leu Tyr Leu
20890                 20895             20900

Glu Leu Ser Gln Leu Thr His Ser Ile Thr Glu Leu Gly Pro Tyr
20905                 20910             20915

Thr Leu Asp Arg Asp Ser Leu Tyr Val Asn Gly Phe Thr His Arg
20920                 20925             20930

Ser Ser Val Pro Thr Thr Ser Thr Gly Val Val Ser Glu Glu Pro
20935                 20940             20945

Phe Thr Leu Asn Phe Thr Ile Asn Asn Leu Arg Tyr Met Ala Asp
20950                 20955             20960

Met Gly Gln Pro Gly Ser Leu Lys Phe Asn Ile Thr Asp Asn Val
20965                 20970             20975

Met Lys His Leu Leu Ser Pro Leu Phe Gln Arg Ser Ser Leu Gly
20980                 20985             20990

Ala Arg Tyr Thr Gly Cys Arg Val Ile Ala Leu Arg Ser Val Lys
20995                 21000             21005

Asn Gly Ala Glu Thr Arg Val Asp Leu Leu Cys Thr Tyr Leu Gln
21010                 21015             21020

Pro Leu Ser Gly Pro Gly Leu Pro Ile Lys Gln Val Phe His Glu
21025                 21030             21035

Leu Ser Gln Gln Thr His Gly Ile Thr Arg Leu Gly Pro Tyr Ser
21040                 21045             21050

Leu Asp Lys Asp Ser Leu Tyr Leu Asn Gly Tyr Asn Glu Pro Gly
21055                 21060             21065

Leu Asp Glu Pro Pro Thr Thr Pro Lys Pro Ala Thr Thr Phe Leu
21070                 21075             21080

Pro Pro Leu Ser Glu Ala Thr Thr Ala Met Gly Tyr His Leu Lys
21085                 21090             21095

Thr Leu Thr Leu Asn Phe Thr Ile Ser Asn Leu Gln Tyr Ser Pro
21100                 21105             21110

Asp Met Gly Lys Gly Ser Ala Thr Phe Asn Ser Thr Glu Gly Val
21115                 21120             21125

Leu Gln His Leu Leu Arg Pro Leu Phe Gln Lys Ser Ser Met Gly
21130                 21135             21140

Pro Phe Tyr Leu Gly Cys Gln Leu Ile Ser Leu Arg Pro Glu Lys
21145                 21150             21155

Asp Gly Ala Ala Thr Gly Val Asp Thr Thr Cys Thr Tyr His Pro
21160                 21165             21170

Asp Pro Val Gly Pro Gly Leu Asp Ile Gln Gln Leu Tyr Trp Glu
21175                 21180             21185

Leu Ser Gln Leu Thr His Gly Val Thr Gln Leu Gly Phe Tyr Val
21190                 21195             21200

Leu Asp Arg Asp Ser Leu Phe Ile Asn Gly Tyr Ala Pro Gln Asn
21205                 21210             21215

```
Leu  Ser  Ile  Arg  Gly  Glu  Tyr  Gln  Ile  Asn  Phe  His  Ile  Val  Asn
21220               21225                    21230

Trp  Asn  Leu  Ser  Asn  Pro  Asp  Pro  Thr  Ser  Glu  Tyr  Ile  Thr
21235               21240                    21245

Leu  Leu  Arg  Asp  Ile  Gln  Asp  Lys  Val  Thr  Thr  Leu  Tyr  Lys  Gly
21250               21255                    21260

Ser  Gln  Leu  His  Asp  Thr  Phe  Arg  Phe  Cys  Leu  Val  Thr  Asn  Leu
21265               21270                    21275

Thr  Met  Asp  Ser  Val  Leu  Val  Thr  Val  Lys  Ala  Leu  Phe  Ser  Ser
21280               21285                    21290

Asn  Leu  Asp  Pro  Ser  Leu  Val  Glu  Gln  Val  Phe  Leu  Asp  Lys  Thr
21295               21300                    21305

Leu  Asn  Ala  Ser  Phe  His  Trp  Leu  Gly  Ser  Thr  Tyr  Gln  Leu  Val
21310               21315                    21320

Asp  Ile  His  Val  Thr  Glu  Met  Glu  Ser  Ser  Val  Tyr  Gln  Pro  Thr
21325               21330                    21335

Ser  Ser  Ser  Ser  Thr  Gln  His  Phe  Tyr  Leu  Asn  Phe  Thr  Ile  Thr
21340               21345                    21350

Asn  Leu  Pro  Tyr  Ser  Gln  Asp  Lys  Ala  Gln  Pro  Gly  Thr  Thr  Asn
21355               21360                    21365

Tyr  Gln  Arg  Asn  Lys  Arg  Asn  Ile  Glu  Asp  Ala  Leu  Asn  Gln  Leu
21370               21375                    21380

Phe  Arg  Asn  Ser  Ser  Ile  Lys  Ser  Tyr  Phe  Ser  Asp  Cys  Gln  Val
21385               21390                    21395

Ser  Thr  Phe  Arg  Ser  Val  Pro  Asn  Arg  His  His  Thr  Gly  Val  Asp
21400               21405                    21410

Ser  Leu  Cys  Asn  Phe  Ser  Pro  Leu  Ala  Arg  Arg  Val  Asp  Arg  Val
21415               21420                    21425

Ala  Ile  Tyr  Glu  Glu  Phe  Leu  Arg  Met  Thr  Arg  Asn  Gly  Thr  Gln
21430               21435                    21440

Leu  Gln  Asn  Phe  Thr  Leu  Asp  Arg  Ser  Ser  Val  Leu  Val  Asp  Gly
21445               21450                    21455

Tyr  Ser  Pro  Asn  Arg  Asn  Glu  Pro  Leu  Thr  Gly  Asn  Ser  Asp  Leu
21460               21465                    21470

Pro  Phe  Trp  Ala  Val  Ile  Leu  Ile  Gly  Leu  Ala  Gly  Leu  Leu  Gly
21475               21480                    21485

Leu  Ile  Thr  Cys  Leu  Ile  Cys  Gly  Val  Leu  Val  Thr  Thr  Arg  Arg
21490               21495                    21500

Arg  Lys  Lys  Glu  Gly  Glu  Tyr  Asn  Val  Gln  Gln  Cys  Pro  Gly
21505               21510                    21515

Tyr  Tyr  Gln  Ser  His  Leu  Asp  Leu  Glu  Asp  Leu  Gln
21520               21525                    21530

<210> SEQ ID NO 46
<211> LENGTH: 2337
<212> TYPE: PRT
<213> ORGANISM: Homo sapiens

<400> SEQUENCE: 46

Met  Val  Arg  Phe  Gly  Asp  Glu  Leu  Gly  Gly  Arg  Tyr  Gly  Gly  Pro  Gly
  1                  5                   10                  15

Gly  Gly  Glu  Arg  Ala  Arg  Gly  Gly  Gly  Ala  Gly  Gly  Ala  Gly  Pro
                20                  25                  30

Gly  Pro  Gly  Gly  Leu  Gln  Pro  Gly  Gln  Arg  Val  Leu  Tyr  Lys  Gln  Ser
             35                  40                  45
```

```
Ile Ala Gln Arg Ala Arg Thr Met Ala Leu Tyr Asn Pro Ile Pro Val
     50                  55                  60

Lys Gln Asn Cys Phe Thr Val Asn Arg Ser Leu Phe Val Phe Ser Glu
65                  70                  75                  80

Asp Asn Val Val Arg Lys Tyr Ala Lys Arg Ile Thr Glu Trp Pro Pro
                 85                  90                  95

Phe Glu Tyr Met Ile Leu Ala Thr Ile Ala Asn Cys Ile Val Leu
             100                 105                 110

Ala Leu Glu Gln His Leu Pro Asp Gly Asp Lys Thr Pro Met Ser Glu
         115                 120                 125

Arg Leu Asp Asp Thr Glu Pro Tyr Phe Ile Gly Ile Phe Cys Phe Glu
         130                 135                 140

Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Leu Thr
                 165                 170                 175

Gly Ile Leu Ala Thr Ala Gly Thr Asp Phe Asp Leu Arg Thr Leu Arg
             180                 185                 190

Ala Val Arg Val Leu Arg Pro Leu Lys Leu Val Ser Gly Ile Pro Ser
         195                 200                 205

Leu Gln Val Val Leu Lys Ser Ile Met Lys Ala Met Val Pro Leu Leu
210                 215                 220

Gln Ile Gly Leu Leu Leu Phe Phe Ala Ile Leu Met Phe Ala Ile Ile
225                 230                 235                 240

Gly Leu Glu Phe Tyr Met Gly Lys Phe His Lys Ala Cys Phe Pro Asn
             245                 250                 255

Ser Thr Asp Ala Glu Pro Val Gly Asp Phe Pro Cys Gly Lys Glu Ala
         260                 265                 270

Pro Ala Arg Leu Cys Glu Gly Asp Thr Glu Cys Arg Glu Tyr Trp Pro
         275                 280                 285

Gly Pro Asn Phe Gly Ile Thr Asn Phe Asp Asn Ile Leu Phe Ala Ile
     290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
                 325                 330                 335

Ile Pro Leu Ile Ile Ile Gly Ser Phe Phe Met Leu Asn Leu Val Leu
             340                 345                 350

Gly Val Leu Ser Gly Glu Phe Ala Lys Glu Arg Glu Arg Val Glu Asn
         355                 360                 365

Arg Arg Ala Phe Leu Lys Leu Arg Gln Gln Gln Ile Glu Arg Glu
         370                 375                 380

Leu Asn Gly Tyr Leu Glu Trp Ile Phe Lys Ala Glu Glu Val Met Leu
385                 390                 395                 400

Ala Glu Glu Asp Arg Asn Ala Glu Glu Lys Ser Pro Leu Asp Val Leu
                 405                 410                 415

Lys Arg Ala Ala Thr Lys Lys Ser Arg Asn Asp Leu Ile His Ala Glu
             420                 425                 430

Glu Gly Glu Asp Arg Phe Ala Asp Leu Cys Ala Val Gly Ser Pro Phe
         435                 440                 445

Ala Arg Ala Ser Leu Lys Ser Gly Lys Thr Glu Ser Ser Ser Tyr Phe
         450                 455                 460

Arg Arg Lys Glu Lys Met Phe Arg Phe Phe Ile Arg Arg Met Val Lys
```

```
                465                 470                 475                 480
        Ala Gln Ser Phe Tyr Trp Val Val Leu Cys Val Val Ala Leu Asn Thr
                        485                 490                 495

Leu Cys Val Ala Met Val His Tyr Asn Gln Pro Arg Arg Leu Thr Thr
                        500                 505                 510

Thr Leu Tyr Phe Ala Glu Phe Val Phe Leu Gly Leu Phe Leu Thr Glu
                        515                 520                 525

Met Ser Leu Lys Met Tyr Gly Leu Gly Pro Arg Ser Tyr Phe Arg Ser
                        530                 535                 540

Ser Phe Asn Cys Phe Asp Phe Gly Val Ile Val Gly Ser Val Phe Glu
        545                 550                 555                 560

Val Val Trp Ala Ala Ile Lys Pro Gly Ser Ser Phe Gly Ile Ser Val
                        565                 570                 575

Leu Arg Ala Leu Arg Leu Leu Arg Ile Phe Lys Val Thr Lys Tyr Trp
                        580                 585                 590

Ser Ser Leu Arg Asn Leu Val Val Ser Leu Leu Asn Ser Met Lys Ser
                        595                 600                 605

Ile Ile Ser Leu Leu Phe Leu Leu Phe Leu Phe Ile Val Val Phe Ala
                        610                 615                 620

Leu Leu Gly Met Gln Leu Phe Gly Gly Gln Phe Asn Phe Gln Asp Glu
        625                 630                 635                 640

Thr Pro Thr Thr Asn Phe Asp Thr Phe Pro Ala Ala Ile Leu Thr Val
                        645                 650                 655

Phe Gln Ile Leu Thr Gly Glu Asp Trp Asn Ala Val Met Tyr His Gly
                        660                 665                 670

Ile Glu Ser Gln Gly Gly Val Ser Lys Gly Met Phe Ser Ser Phe Tyr
                        675                 680                 685

Phe Ile Val Leu Thr Leu Phe Gly Asn Tyr Thr Leu Leu Asn Val Phe
                        690                 695                 700

Leu Ala Ile Ala Val Asp Asn Leu Ala Asn Ala Gln Glu Leu Thr Lys
        705                 710                 715                 720

Asp Glu Glu Glu Met Glu Glu Ala Ala Asn Gln Lys Leu Ala Leu Gln
                        725                 730                 735

Lys Ala Lys Glu Val Ala Glu Val Ser Pro Met Ser Ala Ala Asn Ile
                        740                 745                 750

Ser Ile Ala Ala Arg Gln Gln Asn Ser Ala Lys Ala Arg Ser Val Trp
                        755                 760                 765

Glu Gln Arg Ala Ser Gln Leu Arg Leu Gln Asn Leu Arg Ala Ser Cys
                        770                 775                 780

Glu Ala Leu Tyr Ser Glu Met Asp Pro Glu Glu Arg Leu Arg Phe Ala
        785                 790                 795                 800

Thr Thr Arg His Leu Arg Pro Asp Met Lys Thr His Leu Asp Arg Pro
                        805                 810                 815

Leu Val Val Glu Leu Gly Arg Asp Gly Ala Arg Gly Pro Val Gly Gly
                        820                 825                 830

Lys Ala Arg Pro Glu Ala Ala Glu Ala Pro Glu Gly Val Asp Pro Pro
                        835                 840                 845

Arg Arg His His Arg His Arg Asp Lys Asp Lys Thr Pro Ala Ala Gly
        850                 855                 860

Asp Gln Asp Arg Ala Glu Ala Pro Lys Ala Glu Ser Gly Glu Pro Gly
        865                 870                 875                 880

Ala Arg Glu Glu Arg Pro Arg Pro His Arg Ser His Ser Lys Glu Ala
                        885                 890                 895
```

```
Ala Gly Pro Pro Glu Ala Arg Ser Glu Arg Gly Arg Gly Pro
        900                 905                 910

Glu Gly Gly Arg Arg His His Arg Gly Ser Pro Glu Ala Ala
        915                 920                 925

Glu Arg Glu Pro Arg Arg His Arg Ala His Arg His Gln Asp Pro Ser
        930                 935                 940

Lys Glu Cys Ala Gly Ala Lys Gly Glu Arg Arg Ala Arg His Arg Gly
945                 950                 955                 960

Gly Pro Arg Ala Gly Pro Arg Glu Ala Glu Ser Gly Glu Glu Pro Ala
                965                 970                 975

Arg Arg His Arg Ala Arg His Lys Ala Gln Pro Ala His Glu Ala Val
                980                 985                 990

Glu Lys Glu Thr Thr Glu Lys Glu Ala Thr Glu Lys Glu Ala Glu Ile
        995                 1000                1005

Val Glu Ala Asp Lys Glu Lys Glu Leu Arg Asn His Gln Pro Arg Glu
        1010                1015                1020

Pro His Cys Asp Leu Glu Thr Ser Gly Thr Val Thr Val Gly Pro Met
1025                1030                1035                1040

His Thr Leu Pro Ser Thr Cys Leu Gln Lys Val Glu Glu Gln Pro Glu
                1045                1050                1055

Asp Ala Asp Asn Gln Arg Asn Val Thr Arg Met Gly Ser Gln Pro Pro
                1060                1065                1070

Asp Pro Asn Thr Ile Val His Ile Pro Val Met Leu Thr Gly Pro Leu
                1075                1080                1085

Gly Glu Ala Thr Val Val Pro Ser Gly Asn Val Asp Leu Glu Ser Gln
        1090                1095                1100

Ala Glu Gly Lys Lys Glu Val Glu Ala Asp Asp Val Met Arg Ser Gly
1105                1110                1115                1120

Pro Arg Pro Ile Val Pro Tyr Ser Ser Met Phe Cys Leu Ser Pro Thr
                1125                1130                1135

Asn Leu Leu Arg Arg Phe Cys His Tyr Ile Val Thr Met Arg Tyr Phe
                1140                1145                1150

Glu Val Val Ile Leu Val Val Ile Ala Leu Ser Ser Ile Ala Leu Ala
        1155                1160                1165

Ala Glu Asp Pro Val Arg Thr Asp Ser Pro Arg Asn Asn Ala Leu Lys
1170                1175                1180

Tyr Leu Asp Tyr Ile Phe Thr Gly Val Phe Thr Phe Glu Met Val Ile
1185                1190                1195                1200

Lys Met Ile Asp Leu Gly Leu Leu Leu His Pro Gly Ala Tyr Phe Arg
                1205                1210                1215

Asp Leu Trp Asn Ile Leu Asp Phe Ile Val Ser Gly Ala Leu Val
                1220                1225                1230

Ala Phe Ala Phe Ser Gly Ser Lys Gly Lys Asp Ile Asn Thr Ile Lys
        1235                1240                1245

Ser Leu Arg Val Leu Arg Val Leu Arg Pro Leu Lys Thr Ile Lys Arg
        1250                1255                1260

Leu Pro Lys Leu Lys Ala Val Phe Asp Cys Val Val Asn Ser Leu Lys
1265                1270                1275                1280

Asn Val Leu Asn Ile Leu Ile Val Tyr Met Leu Phe Met Phe Ile Phe
                1285                1290                1295

Ala Val Ile Ala Val Gln Leu Phe Lys Gly Lys Phe Phe Tyr Cys Thr
        1300                1305                1310

Asp Glu Ser Lys Glu Leu Glu Arg Asp Cys Arg Gly Gln Tyr Leu Asp
        1315                1320                1325
```

```
Tyr Glu Lys Glu Glu Val Glu Ala Gln Pro Arg Gln Trp Lys Lys Tyr
    1330                1335                1340

Asp Phe His Tyr Asp Asn Val Leu Trp Ala Leu Leu Thr Leu Phe Thr
1345                1350                1355                1360

Val Ser Thr Gly Glu Gly Trp Pro Met Val Leu Lys His Ser Val Asp
                1365                1370                1375

Ala Thr Tyr Glu Glu Gln Gly Pro Ser Pro Gly Tyr Arg Met Glu Leu
                1380                1385                1390

Ser Ile Phe Tyr Val Val Tyr Phe Val Val Phe Pro Phe Phe Phe Val
                1395                1400                1405

Asn Ile Phe Val Ala Leu Ile Ile Ile Thr Phe Gln Glu Gln Gly Asp
                1410                1415                1420

Lys Val Met Ser Glu Cys Ser Leu Glu Lys Asn Glu Arg Ala Cys Ile
1425                1430                1435                1440

Asp Phe Ala Ile Ser Ala Lys Pro Leu Thr Arg Tyr Met Pro Gln Asn
                1445                1450                1455

Arg Gln Ser Phe Gln Tyr Lys Thr Trp Thr Phe Val Val Ser Pro Pro
                1460                1465                1470

Phe Glu Tyr Phe Ile Met Ala Met Ile Ala Leu Asn Thr Val Val Leu
                1475                1480                1485

Met Met Lys Phe Tyr Asp Ala Pro Tyr Glu Tyr Glu Leu Met Leu Lys
                1490                1495                1500

Cys Leu Asn Ile Val Phe Thr Ser Met Phe Ser Met Glu Cys Val Leu
1505                1510                1515                1520

Lys Ile Ile Ala Phe Gly Val Leu Asn Tyr Phe Arg Asp Ala Trp Asn
                1525                1530                1535

Val Phe Asp Phe Val Thr Val Leu Gly Ser Ile Thr Asp Ile Leu Val
                1540                1545                1550

Thr Glu Ile Ala Asn Asn Phe Ile Asn Leu Ser Phe Leu Arg Leu Phe
                1555                1560                1565

Arg Ala Ala Arg Leu Ile Lys Leu Leu Arg Gln Gly Tyr Thr Ile Arg
                1570                1575                1580

Ile Leu Leu Trp Thr Phe Val Gln Ser Phe Lys Ala Leu Pro Tyr Val
1585                1590                1595                1600

Cys Leu Leu Ile Ala Met Leu Phe Phe Ile Tyr Ala Ile Ile Gly Met
                1605                1610                1615

Gln Val Phe Gly Asn Ile Ala Leu Asp Asp Asp Thr Ser Ile Asn Arg
                1620                1625                1630

His Asn Asn Phe Arg Thr Phe Leu Gln Ala Leu Met Leu Leu Phe Arg
                1635                1640                1645

Ser Ala Thr Gly Glu Ala Trp His Glu Ile Met Leu Ser Cys Leu Ser
                1650                1655                1660

Asn Gln Ala Cys Asp Glu Gln Ala Asn Ala Thr Glu Cys Gly Ser Asp
1665                1670                1675                1680

Phe Ala Tyr Phe Tyr Phe Val Ser Phe Ile Phe Leu Cys Ser Phe Leu
                1685                1690                1695

Met Leu Asn Leu Phe Val Ala Val Ile Met Asp Asn Phe Glu Tyr Leu
                1700                1705                1710

Thr Arg Asp Ser Ser Ile Leu Gly Pro His His Leu Asp Glu Phe Ile
                1715                1720                1725

Arg Val Trp Ala Glu Tyr Asp Pro Ala Ala Cys Gly Arg Ile Ser Tyr
                1730                1735                1740

Asn Asp Met Phe Glu Met Leu Lys His Met Ser Pro Pro Leu Gly Leu
```

```
            1745                1750                1755                1760
Gly Lys Lys Cys Pro Ala Arg Val Ala Tyr Lys Arg Leu Val Arg Met
                1765                1770                1775
Asn Met Pro Ile Ser Asn Glu Asp Met Thr Val His Phe Thr Ser Thr
                1780                1785                1790
Leu Met Ala Leu Ile Arg Thr Ala Leu Glu Ile Lys Leu Ala Pro Ala
                1795                1800                1805
Gly Thr Lys Gln His Gln Cys Asp Ala Glu Leu Arg Lys Glu Ile Ser
                1810                1815                1820
Val Val Trp Ala Asn Leu Pro Gln Lys Thr Leu Asp Leu Leu Val Pro
1825                1830                1835                1840
Pro His Lys Pro Asp Glu Met Thr Val Gly Lys Val Tyr Ala Ala Leu
                1845                1850                1855
Met Ile Phe Asp Phe Tyr Lys Gln Asn Lys Thr Thr Arg Asp Gln Met
                1860                1865                1870
Gln Gln Ala Pro Gly Gly Leu Ser Gln Met Gly Pro Val Ser Leu Phe
                1875                1880                1885
His Pro Leu Lys Ala Thr Leu Glu Gln Thr Gln Pro Ala Val Leu Arg
                1890                1895                1900
Gly Ala Arg Val Phe Leu Arg Gln Lys Ser Ser Thr Ser Leu Ser Asn
1905                1910                1915                1920
Gly Gly Ala Ile Gln Asn Gln Glu Ser Gly Ile Lys Glu Ser Val Ser
                1925                1930                1935
Trp Gly Thr Gln Arg Thr Gln Asp Ala Pro His Glu Ala Arg Pro Pro
                1940                1945                1950
Leu Glu Arg Gly His Ser Thr Glu Ile Pro Val Gly Arg Ser Gly Ala
                1955                1960                1965
Leu Ala Val Asp Val Gln Met Gln Ser Ile Thr Arg Arg Gly Pro Asp
                1970                1975                1980
Gly Glu Pro Gln Pro Gly Leu Glu Ser Gln Gly Arg Ala Ala Ser Met
1985                1990                1995                2000
Pro Arg Leu Ala Ala Glu Thr Gln Pro Val Thr Asp Ala Ser Pro Met
                2005                2010                2015
Lys Arg Ser Ile Ser Thr Leu Ala Gln Arg Pro Arg Gly Thr His Leu
                2020                2025                2030
Cys Ser Thr Thr Pro Asp Arg Pro Pro Ser Gln Ala Ser Ser His
                2035                2040                2045
His His His Arg Cys His Arg Arg Asp Arg Lys Gln Arg Ser
                2050                2055                2060
Leu Glu Lys Gly Pro Ser Leu Ser Ala Asp Met Asp Gly Ala Pro Ser
2065                2070                2075                2080
Ser Ala Val Gly Pro Gly Leu Pro Pro Gly Glu Gly Pro Thr Gly Cys
                2085                2090                2095
Arg Arg Glu Arg Glu Arg Gln Glu Arg Gly Arg Ser Gln Glu Arg
                2100                2105                2110
Arg Gln Pro Ser Ser Ser Ser Glu Lys Gln Arg Phe Tyr Ser Cys
                2115                2120                2125
Asp Arg Phe Gly Gly Arg Glu Pro Pro Lys Pro Lys Pro Ser Leu Ser
                2130                2135                2140
Ser His Pro Thr Ser Pro Thr Ala Gly Gln Glu Pro Gly Pro His Pro
2145                2150                2155                2160
Gln Gly Ser Gly Ser Val Asn Gly Ser Pro Leu Leu Ser Thr Ser Gly
                2165                2170                2175
```

-continued

```
Ala Ser Thr Pro Gly Arg Gly Gly Arg Arg Gln Leu Pro Gln Thr Pro
            2180                2185                2190

Leu Thr Pro Arg Pro Ser Ile Thr Tyr Lys Thr Ala Asn Ser Ser Pro
            2195                2200                2205

Ile His Phe Ala Gly Ala Gln Thr Ser Leu Pro Ala Phe Ser Pro Gly
            2210                2215                2220

Arg Leu Ser Arg Gly Leu Ser Glu His Asn Ala Leu Leu Gln Arg Asp
2225                2230                2235                2240

Pro Leu Ser Gln Pro Leu Ala Pro Gly Ser Arg Ile Gly Ser Asp Pro
            2245                2250                2255

Tyr Leu Gly Gln Arg Leu Asp Ser Glu Ala Ser Val His Ala Leu Pro
            2260                2265                2270

Glu Asp Thr Leu Thr Phe Glu Glu Ala Val Ala Thr Asn Ser Gly Arg
            2275                2280                2285

Ser Ser Arg Thr Ser Tyr Val Ser Ser Leu Thr Ser Gln Ser His Pro
            2290                2295                2300

Leu Arg Arg Val Pro Asn Gly Tyr His Cys Thr Leu Gly Leu Ser Ser
2305                2310                2315                2320

Gly Gly Arg Ala Arg His Ser Tyr His His Pro Asp Gln Asp His Trp
            2325                2330                2335

Cys

<210> SEQ ID NO 47
<211> LENGTH: 4
<212> TYPE: PRT
<213> ORGANISM: Artificial Sequence
<220> FEATURE:
<223> OTHER INFORMATION: linker sequence

<400> SEQUENCE: 47

Gly Gly Gly Ser
  1
```

US 8,426,367 B2

PEPTIDES SPECIFIC FOR HUMAN BLOOD OUTGROWTH ENDOTHELIAL CELLS

CROSS-REFERENCE TO RELATED APPLICATIONS

This is a U.S. National Phase of PCT/US2008/055874, filed Mar. 5, 2008, and claims the benefit of U.S. Provisional Application Ser. No. 60/892,987, filed Mar. 5, 2007, each of which is hereby incorporated in its entirety by reference herein.

FEDERALLY SPONSORED RESEARCH OR DEVELOPMENT

This invention was made with United States Government support under Grant Nos. RO1 HL616656, HL061656, HL085293, and HL065619 awarded by the National Institutes of Health. The United States Government has certain rights in this invention.

REFERENCE TO SEQUENCE LISTING SUBMITTED ELECTRONICALLY

The official copy of the sequence listing is submitted electronically via EFS-Web as an ASCII formatted sequence listing with a file named "377827$_{13}$SequenceListing.txt", created on Sep. 4, 2009, and having a size of 223 kilobytes and is filed concurrently with the specification. The sequence listing contained in this ASCII formatted document is part of the specification and is herein incorporated by reference in its entirety.

FIELD OF THE INVENTION

The present invention is directed to compositions and methods for treating vascular disease and ischemia by enhancing the retention of outgrowth endothelial cells at the site of vascular injury.

BACKGROUND OF THE INVENTION

Cardiovascular disease and its associated maladies, dysfunctions and complications are a principal cause of disability and the chief cause of death in the United States. One factor contributing to cardiovascular disease is atherosclerosis. Atherosclerosis has been generally recognized as the leading health care problem both with respect to mortality and health care costs.

Atherosclerosis is a disease characterized by the deposition of fatty substances, primarily cholesterol, and subsequent fibrosis in the inner layer of an artery, resulting in plaque deposition on the inner surface of the arterial wall and degeneration. If allowed to progress, atherosclerosis can cause narrowing and obstruction of the lumen of the artery resulting in diminished or occluded blood flow. This can lead to ischemia or infarction of the predominantly affected organ or anatomical region, such as the brain, heart, intestine, or extremities.

Angiogenesis is the process of new blood vessel development from preexisting vasculature. Angiogenesis is a normal process in growth and development, as well as in wound healing. It can occur during coronary artery disease, peripheral artery disease and stroke when there is insufficient blood supply and oxygen to the tissues. Vasculogenesis is the process of blood vessel formation from endothelial progenitor cells (EPC) that differentiate in situ.

Until recently, vasculogenesis was thought to be limited to embryologic development. However, the discovery of circulating endothelial progenitor cells has provided evidence that postnatal vasculogenesis also occurs in adults. Progenitor cell-based regenerative strategies offer new perspectives in cell therapies and tissue engineering for achieving an effective revascularization of ischemic or injured tissues. Cultures from peripheral blood contain cells termed early-EPC that share some endothelial but also monocytic characteristics and exhibit a restricted capacity of expansion. Another cell population isolated from peripheral blood cultures is called late-EPC or blood outgrowth endothelial cells (BOEC) that have a cobblestone morphology and have high proliferative capacity.

SUMMARY OF THE INVENTION

Compositions and methods for binding outgrowth endothelial cells (OEC) are provided. The compositions comprise peptide ligands capable of binding OEC with high affinity and specificity. The compositions of the invention include peptides set forth in Table 1 and variants and derivatives thereof. Compositions also include the nucleotide sequences encoding the peptides of the invention. The nucleotide sequences can be used in DNA constructs or expression cassettes for transformation and expression in mammals.

The compositions find use in methods for the isolation of OEC and for the recruitment and retention of OEC to sites of therapeutic interest. Methods for use of the compositions in cell therapies including angiogenesis, blood vessel repair, ischemic tissue repair, and therapeutic revascularization are provided. The compositions can be used in combination with biomedical devices. Methods for the identification and isolation of other peptides capable of binding OEC are also provided.

DETAILED DESCRIPTION OF THE INVENTION

Overview

Figure 1A:
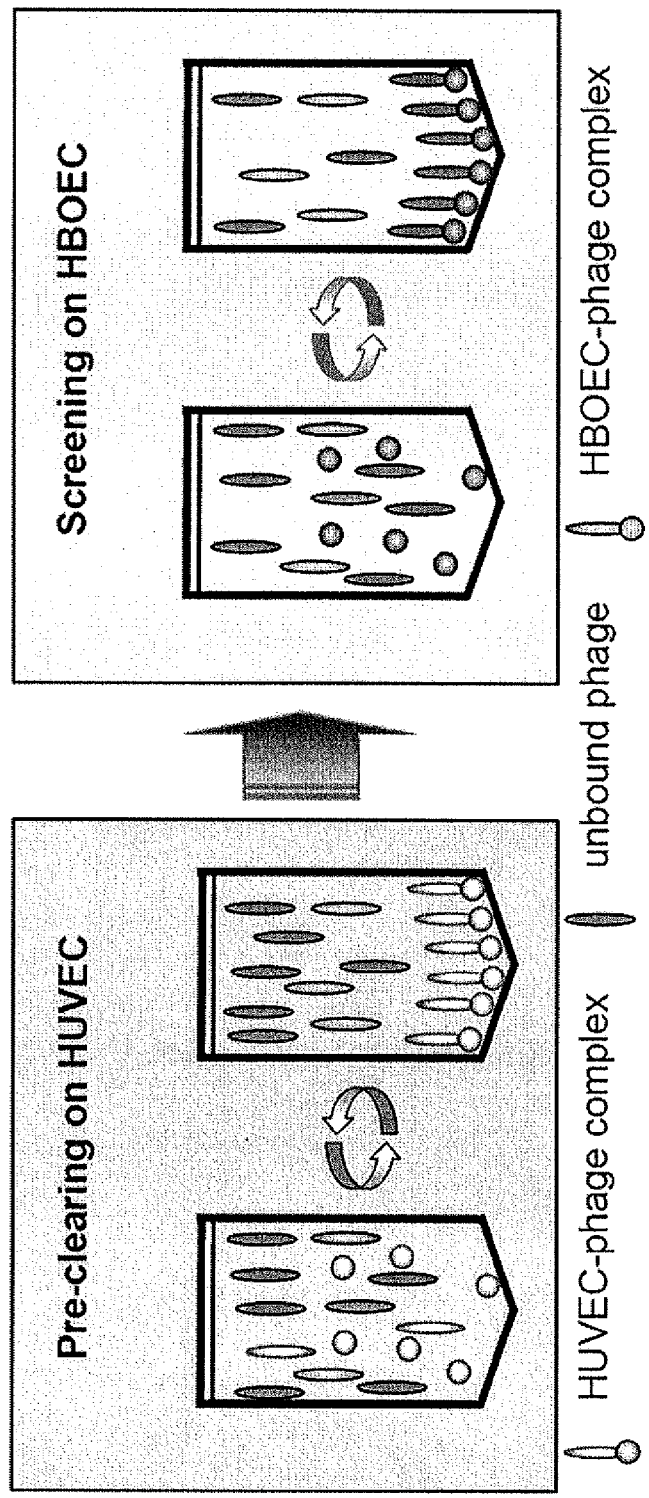
FIG. 1A provides a schematic representation of the biopanning procedure for selection of peptide ligands that bind specifically to OEC.

The present invention provides novel peptides for use in therapeutic methods employing cell therapy to treat vascular diseases, including atherosclerosis and heart disease. The invention is further directed to a method for inducing angiogenesis or neovascularization in a mammal by administering to the mammal an effective amount of the peptides of the invention in combination with OECs. The compositions may further employ a population of endothelial precursor cells, cardiac microvascular endothelial cells (CMECs), young bone marrow cells, stem cells, embryonic stem cell lines or hematopoietic stem cells to treat vascular disease or ischemia.

The invention is based on studies demonstrating the effectiveness of outgrowth endothelial cells (OEC) for treating vascular disease and ischemia by promoting neovascularization and re-endothelialization. Neovascularization refers to the development of new blood vessels from endothelial precursor cells by any means, such as by vasculogenesis, angiogenesis, or the formation of new blood vessels from endothelial precursor cells that link to existing blood vessels. Angiogenesis is the process by which new blood vessels grow from the endothelium of existing blood vessels in a developed animal Angiogenesis is essential for wound healing and for reproduction. Re-endothelialization refers to the homing of circulating endothelial precursor cells to sites of intimal injury such as occurs in atherosclerotic plaques.

Endothelial precursor cells such as OECs circulate in the blood and selectively migrate, or "home," to sites of active angiogenesis (see U.S. Pat. No. 5,980,887, Isner et al., the contents of which are incorporated herein by reference in their entirety). OECs (also referred to as are circulating bone marrow-derived endothelial cells and late EPCs) are closer to mature endothelial cells in phenotype but show surprising proliferative, migrating, and tube-forming capabilities. OECs exhibit the typical "cobblestone" morphology of endothelial cells. These cells incorporate acetylated low-density lipoprotein (LDL) and are uniformly positive for vWF, P1H12, thrombomodulin, flk-1, VE-cadherin, PECAM-1, CD34, CD36, and integrin $\alpha_V$. They are uniformly negative for monocyte marker CD14.

Such endothelial precursor cells are capable of homing to sites of cardiac angiogenic induction and homing to sites of intimal injury to facilitate re-endothelialization. These cells can restore and stimulate cardiac angiogenesis in an aging host, for example, by healing injured vascular tissues, reducing the size of atherosclerotic lesions, stimulating angiogenesis, generating cardiac myocytes and promoting formation of new blood vessels and new endothelial tissues.

The present invention provides compositions and methods for identifying, purifying, and characterizing OECs, as well as improving the therapeutic efficacy of OECs in treating vascular disorders and injury.

Compositions

Peptides capable of specific binding to outgrowth endothelial cells (OEC) with high affinity are provided. The peptides of the invention comprise those set forth in SEQ ID NO:1-38 and variants and derivatives thereof. Some of the peptides are characterized by the presence of consensus motifs. These consensus motifs are underlined in some of the peptides listed in Table 1.

All of the peptides set forth in Table 1 contain 12 amino acids. However, it is recognized that the peptides may contain fewer than 12 amino acids or more than 12 amino acids. The peptides of the invention comprise at least 6, at least 7, at least 8, at least 9 at least 10, at least 11, at least 12, up to at least about 40 amino acids. That is, the peptides may comprise at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, up to at least about 40 amino acids.

As indicated above, the peptides may contain at least one consensus motif. The motifs include PLR, PPR, TP, TPT, TPS, TPG, PPS, and MPT.

The term "peptide" broadly refers to an amino acid chain that includes naturally occurring amino acids, synthetic amino acids, genetically encoded amino acids, non-genetically encoded amino acids, and combinations thereof. Peptides can include both L-form and D-form amino acids.

Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; and ornithine.

Representative derivatized amino acids include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine.

Biologically active variants of the peptides of the invention are also encompassed by the present invention. Such variants should retain binding activity to OEC, particularly the ability to specifically bind OEC. Binding activity can be measured by methods in the art. For example, see the experimental section of the present application. Preferably, the variant has at least the same activity as the native molecule. The activity can also be associated with the affinity and/or specificity of OEC binding, or can be associated with particular downstream in vivo activities such as improved perfusion, decreased neointimal formation, decreased thromboses, and greater capillary density when administered to a subject as described elsewhere herein.

Suitable biologically active variants can be fragments and derivatives. By "fragment" is intended a peptide consisting of only a part of the intact peptide sequence and structure, and can be a C-terminal deletion or N-terminal deletion of amino acids or deletions at both the C- and N-terminal ends. By "derivatives" is intended any suitable modification of a binding peptide or peptide fragment encompassing any change in amino acid residues, so long as the binding activity is retained.

Peptide variants will generally have at least 70%, preferably at least 80%, more preferably about 90% to 95% or more, about 96%, about 97%, and most preferably about 98%, about 99% or more amino acid sequence identity to the amino acid sequence of the reference peptide molecule. A variant may differ by as few as 3, 2, or even 1 amino acid residue. Methods for determining identity between sequences are well known in the art. See, for example, the ALIGN program (Dayhoff (1978) in *Atlas of Protein Sequence and Structure* 5:Suppl. 3 (National Biomedical Research Foundation, Washington, D.C.) and programs in the Wisconsin Sequence Analysis Package, Version 8 (available from Genetics Computer Group, Madison, Wis.), for example, the GAP program. For purposes of optimal alignment of the two sequences, the contiguous segment of the amino acid sequence of the variant may have additional amino acid residues or deleted amino acid residues with respect to the amino acid sequence of the reference molecule. The contiguous segment used for comparison to the reference amino acid sequence will comprise at least twelve (12), at least about 13, at least about 14, about 15, about 16, about 17, about 18, about 19, about 20, about 25, about 30, at least about 35 or more amino acids. Corrections for increased sequence identity associated with inclusion of gaps in the variant's amino acid sequence can be made by assigning gap penalties. Methods of sequence alignment are well known in the art. However, when calculating the percent identity of a sequence compared to an amino acid sequence consisting of any one of SEQ ID NO:1-38, the percent identity is calculated across the entirety of any one of SEQ ID NO:1-38, and gaps are typically not allowed.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Meyers and Miller (1988) *Computer Applic. Biol. Sci.* 4:11-17.

For example, preferably, conservative amino acid substitutions may be made. A "nonessential" amino acid residue is a residue that can be altered without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). See, for example, Sambrook J., and Russell, D. W. (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY).

The peptides of the invention can be subject to various changes, substitutions, insertions, and deletions where such changes provide for certain advantages in its use. Thus, the term "peptide" encompasses any of a variety of forms of peptide derivatives including, for example, amides, conjugates with proteins, cyclone peptides, polymerized peptides, conservatively substituted variants, analogs, fragments, chemically modified peptides, and peptide mimetics. Any peptide that has desired binding characteristics can be used in the practice of the present invention.

By "binds specifically" or "specific binding" is intended that the peptides bind to OEC but do not bind to other cell types. In some embodiments, a peptide that binds specifically to OEC binds at least 10%, 20%, 30%, 40%, 50%, 60%, 70%, 80%, 90%, 100%, 200%, 300%, 400%, 500%, or a higher percentage more than the peptide binds to an appropriate control such as, for example, a different cell type.

One aspect of the invention pertains to isolated nucleic acid molecules comprising nucleotide sequences encoding binding peptides or biologically active portions thereof. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleic acid molecules that are fragments of these binding peptide encoding nucleotide sequences are also encompassed by the present invention. By "fragment" is intended a portion of the nucleotide sequence encoding a binding peptide. Nucleic acid molecules that are fragments of a binding peptide nucleotide sequence comprise at least about 15, 20, 50, 75, 100 contiguous nucleotides. By "contiguous" nucleotides is intended nucleotide residues that are immediately adjacent to one another.

The skilled artisan will further appreciate that changes can be introduced by mutation into the nucleotide sequences of the invention thereby leading to changes in the amino acid sequence of the encoded binding peptides, without altering the binding specificity or affinity of the peptides. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded peptide. Mutations can be introduced by standard techniques, such as site-directed mutagenesis and PCR-mediated mutagenesis. Such variant nucleotide sequences are also encompassed by the present invention.

Uses

The peptides of the invention find use in methods for the isolation, recruitment, and retention of OEC. Thus, the peptides of the invention can be used to sequester OEC cells at therapeutic sites of interest and in cell-based therapeutic revascularization approaches to ischemic disease and endothelial injury. "Therapeutic sites of interest" include areas where angiogenesis is desired, areas of ischemic injury, areas of organ transplantation, areas of vascular injury, and the like. Thus, strategies can enhance the number of endothelial cells in the vessel wall following injury and limit complications such as thrombosis, vasospasm, and neointimal formation, through reconstitution of a luminal barrier and cellular secretion of paracrine factors.

The peptides of the invention can be introduced at a therapeutic site of interest. Any method for introducing the peptides at the site may be employed. In the same manner, a therapeutic site of interest can be seeded with at least one peptide of the invention to aid in the selection and retention of OEC at the site. By "seeding" or "seeded" is intended any means for introducing the peptides at the site. Such methods include injection, infusion, and the like. It is recognized that the peptides may be introduced at the site to capture and retain endogenous OEC at the site of interest. Alternatively, peptides with OEC bound may be introduced at the therapeutic site. In the same manner, the peptides may be delivered by gene delivery techniques. That is, the peptides may be expressed at a site of interest by vectors designed to express the peptides in a mammal Vascular Diseases The vascular diseases treated by the present invention are vascular diseases of mammals. The word mammal means any mammal Some examples of mammals include, for example, pet animals, such as dogs and cats; farm animals, such as pigs, cattle, sheep, and goats; laboratory animals, such as mice and rats; primates, such as monkeys, apes, and chimpanzees; and humans. In some embodiments, humans are preferably treated by the methods of the invention.

According to the invention, endothelial cells within normal vascular tissues change as they grow older, exhibit reduced angiogenesis, reduced capacity for re-endothelization and lose their ability to communicate with other cells by secreting signaling agents. These changes can lead to a diminished capacity for blood vessel formation, a reduction in blood flow to the associated organ or system, and an inability to recover from injuries or diseases that adversely affect blood vessels.

Accordingly, the invention relates to methods for treating endothelial dysfunction, or a vascular condition, or a circulatory condition, such as a condition associated with loss, injury or disruption of the vasculature within an anatomical site or system. The term "vascular condition" or "vascular disease" refers to a state of vascular tissue where blood flow is, or can become, impaired.

Many pathological conditions can lead to vascular diseases that are associated with alterations in the normal vascular condition of the affected tissues and/or systems. Examples of vascular conditions or vascular diseases to which the methods of the invention apply are those in which the vasculature of the affected tissue or system is senescent or otherwise altered in some way such that blood flow to the tissue or system is reduced or in danger of being reduced. Examples of vascular conditions that can be treated with the compositions and methods of the invention include atherosclerosis, preeclampsia, peripheral vascular disease, erectile dysfunction, cancers, renal failure, heart disease, and stroke. Vascular, circulatory or hypoxic conditions to which the methods of the invention apply also include those associated with, but not limited to, maternal hypoxia (e.g., placental hypoxia, preeclampsia), abnormal pregnancy, peripheral vascular disease (e.g., arteriosclerosis), transplant accelerated arteriosclerosis, deep vein thrombosis, erectile dysfunction, cancers, renal failure, stroke, heart disease, sleep apnea, hypoxia during sleep, female sexual dysfunction, fetal hypoxia, smoking, anemia, hypovolemia, vascular or circulatory conditions which increase risk of metastasis or tumor progression, hemorrhage, hypertension, diabetes, vasculopathologies, surgery (e.g., per-surgical hypoxia, post-operative hypoxia), Raynaud's disease, endothelial dysfunction, regional perfusion deficits (e.g., limb, gut, renal ischemia), myocardial infarction, stroke, thrombosis, frost bite, decubitus ulcers, asphyxiation, poisoning (e.g., carbon monoxide, heavy metal), altitude sickness, pulmonary hypertension, sudden infant death syndrome (SIDS), asthma, chronic obstructive pulmonary disease (COPD), congenital circulatory abnormalities (e.g., Tetralogy of Fallot) and Erythroblastosis (blue baby syndrome). In particular embodiments, the invention is a method of treating loss of circulation or endothelial dysfunction in an individual.

Thus, the invention is directed to compositions useful in a method of treating diseases such as stroke, atherosclerosis, acute coronary syndromes including unstable angina, thrombosis and myocardial infarction, plaque rupture, both primary and secondary (in-stent) restenosis in coronary or peripheral arteries, transplantation-induced sclerosis, peripheral limb disease, intermittent claudication and diabetic complications (including ischemic heart disease, peripheral artery disease, congestive heart failure, retinopathy, neuropathy and nephropathy), or thrombosis.

In some embodiments, the vascular condition or vascular disease arises from damaged myocardium. As used herein "damaged myocardium" refers to myocardial cells that have been exposed to ischemic conditions. These ischemic conditions may be caused by a myocardial infarction, or other cardiovascular disease. The lack of oxygen causes death of the cells in the surrounding area, leaving an infarct that can eventually scar.

Preferably, damaged myocardium is treated with the methods and compositions of the invention before damage occurs (e.g. when damage is suspected of occurring) or as quickly as possible after damage occurs. Hence, the methods and compositions of the invention are advantageously employed on aged heart tissues that are in danger of ischemia, heart attack or loss of blood flow. The methods and compositions of the invention are also advantageously employed on recently damaged myocardium and on not so recently damaged myocardium.

As used herein "recently damaged myocardium" refers to myocardium that has been damaged within one week of treatment being started. In a preferred embodiment, treatment with the compositions of the invention is initiated within three days of myocardial damage. In a further preferred embodiment, treatment is initiated within 12 hours of myocardial damage.

In one embodiment, the present invention may be used to enhance blood vessel formation in ischemic tissue, i.e., a tissue having a deficiency in blood as the result of an ischemic disease. Such tissues can include, for example, muscle, brain, kidney and lung Ischemic diseases include, for example, cerebrovascular ischemia, renal ischemia, pulmonary ischemia, limb ischemia, ischemic cardiomyopathy and myocardial ischemia.

The methods of the present invention may also be used to treat blood vessel injuries that result in denuding of the endothelial lining of the vessel wall. For example, primary angioplasty is becoming widely used for the treatment of acute myocardial infarction. In addition, endovascular stents are becoming widely used as an adjunct to balloon angioplasty. Stents are useful for rescuing a sub-optimal primary result as well as for diminishing restenosis. To date, however, the liability of the endovascular prosthesis has been its susceptibility to thrombotic occlusion in approximately 3% of patients with arteries 3.3 mm or larger. If patients undergo stent deployment in arteries smaller than this size, the incidence of sub-acute thrombosis is even higher. Sub-acute thrombosis is currently prevented only by the aggressive use of anticoagulation. The combination of vascular intervention and intense anticoagulation creates significant risks with regard to peripheral vascular trauma at the time of the stent/angioplasty procedure. Acceleration of re-endothelialization by administration of stents, implants, or biomedical devices coated with a peptide capable of attracting OECs to a patient undergoing, or subsequent to, angioplasty and/or stent deployment can stabilize an unstable plaque and prevent re-occlusion.

Pharmaceutical Compositions

The invention encompasses pharmaceutical compositions comprising the peptides of the invention. It is recognized that the pharmaceutical composition may contain a plurality of a single binding peptide or mixtures of peptides. Likewise when the peptides are used to coat implants, a single peptide may be used or a combination of peptides may be used. Pharmaceutical compositions formulated with a mixture of at least one binding peptide can be made by methods known in the art. See *Remington's Pharmaceutical Sciences* (18$^{th}$ ed.; Mack Pub. Co.: Eaton, Pa., 1990), herein incorporated by reference. The pharmaceutical composition is administered to supply a desired therapeutic dose to promote a desired therapeutic response of the peptide to the therapeutic area. By "desired therapeutic response" is intended an improvement in the condition or in the symptoms associated with the condition, and the promotion of angiogenesis.

The compositions of this invention will be formulated in a unit dosage such as a solution, suspension or emulsion, in association with a pharmaceutically acceptable carrier. Such carriers are inherently nontoxic and nontherapeutic. Examples of such carriers are saline, Ringer's solution, dextrose solution, and Hanks' solution. Nonaqueous carriers such as fixed oils and ethyl oleate may also be used. The vehicle may contain minor amounts of additives such as substances that enhance chemical stability, including buffers and preservatives.

Suitable methods of delivery of the pharmaceutical composition include, but are not limited to, gel formulations, viscous solutions, sustained-release formulations, implant delivery systems, such as pumps, and the like. Such delivery systems allow for the controlled and concentrated delivery of the peptide(s) to a therapeutic site. The exact formulation employed will depend on the type of application that is desired.

A pharmaceutically effective amount of a pharmaceutical composition of the invention is administered to a subject. By "pharmaceutically effective amount" is intended an amount that is useful in the treatment of a disease or condition, where treatment can be for a therapeutic purpose as noted herein above. In this manner, a pharmaceutically effective amount of the composition will administer a therapeutically effective dose or amount of the binding peptide to the subject in need of treatment. By "therapeutically effective dose or amount" or "effective amount" is intended an amount of the binding peptide that, when administered brings about a positive therapeutic response with respect to angiogenesis, blood vessel repair, ischemic tissue repair, and therapeutic revascularization. In some embodiments of the invention, the therapeutically effective dose is in the range from about 0.1 µg/kg to about 100 mg/kg body weight, about 0.001 mg/kg to about 50 mg/kg, about 0.01 mg/kg to about 30 mg/kg, about 0.1 mg/kg to about 25 mg/kg, about 1 mg/kg to about 20 mg/kg, about 3 mg/kg to about 15 mg/kg, about 5 mg/kg to about 12 mg/kg, about 7 mg/kg to about 10 mg/kg or any range of value therein. It is recognized that the method of treatment may comprise a single administration of a therapeutically effective dose or multiple administrations of a therapeutically effective dose.

It is understood that the effective amount may vary depending on the nature of the effect desired, frequency of treatment, any concurrent treatment, the health, weight of the recipient, and the like. See, e.g., Berkow et al., eds., Merck Manual, 16th edition, Merck and Co., Rahway, N.J. (1992); Goodman et al., eds., Goodman and Gilman's The Pharmacological Basis of Therapeutics, 8th edition, Pergamon Press, Inc., Elmsford, N.Y. (1990); Avery's Drug Treatment: Principles and Practice of Clinical Pharmacology and Therapeutics, 3rd edition, ADIS Press, LTD., Williams and Wilkins, Baltimore, Md. (1987), Ebadi, Pharmacology, Little, Brown and Co., Boston (1985), Katzung, Basic and Clinical Phamacology, Appleton and Lange, Norwalk, Conn. (1992), which references and references cited therein, are entirely incorporated herein by reference.

The pharmaceutical composition may be contained in a pharmaceutically-acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. The use of such media and agents for delivering cells is well known in the art. Except insofar as any conventional media or agent is incompatible with the cells or polypeptides provided herein, use thereof in the compositions is contemplated. Supplementary active compounds can also be incorporated into the compositions.

A pharmaceutical composition of the invention is formulated to be compatible with its intended route of administration. Examples of routes of administration include intravenous, intraarterial, intracoronary, parenteral, subcutaneous, subdermal, subcutaneous, intraperitoneal, intraventricular infusion, infusion catheter, balloon catheter, bolus injection, direct application to tissue surfaces during surgery, or other convenient routes. Solutions or suspensions used for such administration can include other components such as sterile diluents like water for dilution, saline solutions, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The composition can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHORE EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions to accompany the cellular suspensions can be prepared by incorporating an active compound (e.g., a PDGF B polypeptide or PDGF AB protein) in the required amount in an appropriate solvent with a selected combination of ingredients, followed by filter sterilization. Generally, dispersions are prepared by incorporating active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

It is especially advantageous to formulate the cells and/or compositions in dosage unit form for ease of administration and uniformity of dosage. Dosage unit form as used herein refers to physically discrete units suited as unitary dosages for the subject to be treated. Each unit can then contain a predetermined quantity of the peptides and/or cells and other components calculated to produce the desired therapeutic effect in association with the required pharmaceutical carrier.

The pharmaceutical compositions may be co-administered with other agents known to mobilize hematopoietic precursors, with agents known to promote the differentiation of embryonic endothelial cell precursors, or with agents believed to induce angiogenesis, for example, 3-hydroxy-3-methylglutaryl coenzyme A reductase inhibitors (statins), endothelial growth factor, vascular endothelial growth factor (VEGF), fibroblast growth factor (FGF), granulocyte-colony stimulating factor (G-CSF), granulocyte-macrophage-colony stimulating factor (GM-CSF), stem cell factor (SCF), interleukin-3 (Tong et al., Exptl. Hematol. 22:1016-1024, 1994; de Revel et al., Blood 83:3795-3799, 1994; Schots et al., Bone Marrow Transplantation 17:509-515, 1996), and angiopoietin (Takehara et al., Cell 49:415-422, 1987; Suri et al., Cell 87:1171-1180, 1996).

Implants, Stents and Biomedical Devices

It is recognized that the peptides can be administered to therapeutic sites alone or alternatively may be attached to an acceptable implant, stent, or other biomedical device. In this manner, the implant may be coated with peptides. In some embodiments, the peptides will be attached to the implants. Likewise, when the peptides are administered directly and when they are used as coatings for implants, OEC may be attached to the peptides.

The term "implant" generally refers to a structure that is introduced into a human or animal body to restore a function of a damaged tissue or to provide a new function. An implant device can be created using any biocompatible material. Representative implants include but are not limited to: vascular prostheses, artificial heart valves, hip endoprostheses, artificial joints, jaw or facial implants, tendon and ligament replacements, skin replacements, bone replacements, bone graft devices, stents, shunts, nerve growth guides, intraocular lenses, and the like. Implants further comprise scaffolds that merely hold the peptides and/or bound OEC at therapeutic sites of interest. In general, tissue scaffolds are small, porous, implants made of specially designed biomaterials that support a therapeutic site and assist the body in growing new, functional tissue. If the scaffold is degradable, when the damaged or lost tissue has been successfully replaced by new tissue, the scaffold will have completely resorbed.

An "implantable" device is the device, which is adapted for permanent or temporary insertion into or application against a tissue of a mammal such as, for example, a human. Examples of implantable devices or components include, but are not limited to, an artificial heart, cardiac pacer leads, automatic implantable cardiodefibrilator leads, a prosthetic heart valve, a cardiopulmonary bypass membrane, a ventricular assist device, an annuloplasty ring, a dermal graft, a vascular graft, a vascular, cardiovascular, or structural stent, a catheter, a guide wire, a vascular or cardiovascular shunt, a dura mater graft, a cartilage graft, a cartilage implant, a pericardium graft, a ligament prosthesis, a tendon prosthesis, a urinary bladder prosthesis, a pledget, a suture, a permanently in-dwelling percutaneous device, an artificial joint, an artificial limb, a bionic construct (i.e. one of the aforementioned devices or components comprising a microprocessor or other electronic component), and a surgical patch.

Implants are made of a variety of materials that are known in the art and include but are not limited to: a polymer or a mixture of polymers including, for example, biodegradable plastics, polylactic acid, polyglycolic acid, polylactic acid-polyglycolic acid copolymers, polyanhidrides, polyorthoesters, polystyrene, polycarbonate, nylon, PVC, collagen (including, for example, processed collagen such as cross-linked collagen), glycosaminoglycans, hyaluronic acid, alginate, silk, fibrin, cellulose, and rubber; plastics such as polyethylene (including, for example, high-density polyethylene (HDPE)), PEEK (polyetheretherketone), and polytetrafluoroethylene; metals such as titanium, titanium alloy, stainless steel, and cobalt chromium alloy; metal oxides; non-metal oxides; silicone; bioactive glass; ceramic material such as, for example, aluminum oxide, zirconium oxide, and calcium phosphate; other suitable materials such as demineralized bone matrix; and combinations thereof. The term "polymer" as used herein refers to any of numerous natural and synthetic compounds of usually high molecular weight consisting of up to millions of repeated linked units, each a relatively simple molecule.

Synthetic grafts useful in the present invention may be composed of any material suitable for this purpose. To be suitable, a graft must be suturable to the host vessel, durable, and impervious to blood loss at implantation. Typically, synthetic grafts are pretreated prior to implantation, e.g., preclotted with autologous blood, or are coated with partially hydrolyzed proteins during manufacture. Preferred materials for the vascular grafts used in accord with the subject methods include polyethylene terephthalate and polytetrafluoroethylene (PTFE). In one embodiment, the synthetic vascular graft is composed of polyethylene terephthalate, which may be knit or woven. It is within the contemplation of this invention that these or other synthetic substances can be chemically modified to enhance their susceptibility to colonization by circulating endothelial precursor cells.

Thus, the present invention provides methods for preparing an implant to be surgically placed into a patient wherein the device is coated with at least one binding peptide. Methods for attaching peptides to implants are generally known in the art, i.e., by the use of bovine serum albumin, by the use of acrylic acid coupling, bromoalkylation, etc. The peptides may be applied by dipping, spraying, or brushing a solution containing the peptide onto the implant. See, e.g., Harris et al. (2004) *Biomaterials* 25: 4135-4148 and U.S. patent application Ser. No. 10/644,703, filed Aug. 19, 2003 and published on May 6, 2004 with Publication No. 20040087505.

In one embodiment of the invention, the peptide mediates OEC cell attachment to the surface of an implant. By enhancing OEC adhesion, the peptides of the invention can accelerate healing, accelerate angiogenesis and improve the function of the implanted device. Implants can be coated with the peptides of the invention before implantation. Likewise in some embodiments, the implants will be coated with peptides bound to OECs for implantation. This method is referred to herein as "seeding" the OECs on the implantation device.

There are multiple techniques known in the art for the seeding of selected cells to an implantation device (see, for example, U.S. Pat. Nos. 5,674,722; 5,785,965; and 5,766,584). Typically, the implantation device is incubated in vitro, optionally with rotation, to allow the binding of the endothelial cells to the surface of the device. After several hours or days of culture, the device may be implanted into the host. Alternatively, the endothelial cells may be mixed with blood prior to application onto the implantation device.

More specifically, the number of cells deposited on the device coated with the peptides of the invention may be between about $10^3$ cells/cm$^2$ and $10^{12}$ cells/cm$^2$ of device surface, typically about $5 \times 10^5$ cells/cm$^2$. The cells are deposited in any convenient sterile medium, e.g. phosphate buffered saline (PBS), normal saline, M199, Dulbecco's Modified Eagles Medium (DMEM), and the like. The volume of medium will be sufficient to resuspend the cells, generally ranging from about 1 to 25 ml of medium.

After deposition, the device may be implanted immediately into the recipient or may be maintained in a conventional endothelial cell culture for a period of time. Cells employed for seeding on the implantable device may be obtained by any method known in the art. Cells may be obtained at the time of the implantation procedure using standard biopsy techniques, whether the procedure is angioplasty, open field surgery or for diagnostic purposes. The cells may also be dissociated with collagenase or trypsin and seeded directly into a matrix as exemplified below for immediate implantation or for culturing in vitro as required to generate the number of cells to be implanted. Specifically, cells may be isolated by standard methods described in, for example, Gimbrone, M. (1976) Progress Hemostasis and Thrombosis 3:1-28 and U.S. Pat. No. 5,131,907.

Gene Therapy

Recently, the feasibility of gene therapy for modulating angiogenesis has been demonstrated (Takeshita, et al., Laboratory Investigation, 75:487-502 (1996); Isner, et al., Lancet, 348:370 (1996); U.S. Ser. No. 08/545,998; Tsurumi et al. (1996) *Circulation* 94(12):3281-90). The peptides of the invention find use in gene therapy for modification of vascular responses including restoration of endothelial integrity, repairing of ischemic injury, promoting angiogenesis, and the like. The peptides of the invention optimize cell delivery and cell retention to the site of interest, particularly OECs at the site of vascular injury.

The peptides of the invention can be expressed from vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

In one embodiment, a host cell is genetically modified to contain a stably integrated gene that confers a therapeutic effect by methods available in the art. In one embodiment, the gene that confers a therapeutic effect is a gene that encodes one or more of the peptides of the invention. Expression of this gene in an area in need of re-endothelialization and/or vascular repair can lead to the recruitment and retention of OECs at the site of repair.

In another embodiment, the gene that confers a therapeutic effect is a gene that encodes a therapeutic peptide or protein other than the peptides of the invention. When used in combination with the peptides of the invention, vascular repair is enhanced. For example, genetically-modified OECs or other suitable endothelial precursor cells can be used to administer therapeutic agents such as angiogenic enzymes, peptides and/or proteins with angiogenic activity, or nucleic acids or genes that encode therapeutic polypeptides involved in vascular repair. Nucleic acids encoding such therapeutic agents are introduced into OECs or endothelial precursor cells based upon their ability to optimally treat one or more vascular conditions. For example, the endothelial precursor cell can be designed to help control, diminish or otherwise facilitate improved arterial blood flow in the region of an atherosclerotic lesion.

Recombinant expression vectors are made and introduced into the cells using standard techniques, e.g., electroporation, lipid-mediated transfection, or calcium-phosphate mediated transfection, and cells containing stably integrated expression constructs are selected or otherwise identified, also using standard techniques known in the art. Methods for making recombinant DNA expression constructs, introducing them into eukaryotic cells, and identifying cells in which the expression construct is stably integrated and efficiently expressed, are described, for example, in Sambrook, et al., Molecular Cloning: A Laboratory Manual, 2d Edition, Cold Spring Harbor Laboratory Press (1989); Sambrook, et al., Molecular Cloning: A Laboratory Manual, 2d Edition, Cold Spring Harbor Laboratory Press (2001). Such methods useful for practicing the present invention are also described, for example, in U.S. Pat. No. 5,980,887.

The therapeutic agent nucleic acid sequences may be inserted into the vector by a variety of procedures. In general, DNA is inserted into an appropriate restriction endonuclease site(s) using techniques known in the art. See generally, Sambrook et al., 1989, Molecular Cloning, A Laboratory Manual, 2d ed., Cold Spring Harbor Laboratory Press, Cold Spring Harbor, N.Y.; Sambrook and Russell, Molecular Cloning: A Laboratory Manual, 3rd edition (Jan. 15, 2001) Cold Spring Harbor Laboratory Press, ISBN: 0879695765; Ausubel et al., Current Protocols in Molecular Biology, Green Publishing Associates and Wiley Interscience, NY (1989)). Construction of suitable expression vectors containing a therapeutic agent can employ standard ligation techniques that are known to the skilled artisan.

The expression cassette or vector of the invention includes a promoter. A promoter is a nucleotide sequence that controls expression of an operably linked nucleic acid sequence by providing a recognition site for RNA polymerase, and possibly other factors, required for proper transcription. A promoter includes a minimal promoter, consisting only of all basal elements needed for transcription initiation, such as a TATA-box and/or other sequences that serve to specify the site of transcription initiation. Any promoter able to direct transcription of an RNA encoding the selected therapeutic agent may be used. Accordingly, many promoters may be included within the expression cassette or vector of the invention. Some useful promoters include, constitutive promoters, inducible promoters, regulated promoters, cell specific promoters, viral promoters, and synthetic promoters. A promoter may be obtained from a variety of different sources. For example, a promoter may be derived entirely from a native gene, be composed of different elements derived from different promoters found in nature, or be composed of nucleic acid sequences that are entirely synthetic. A promoter may be derived from many different types of organisms and tailored for use within a given cell, for example, an OEC or other endothelial precursor cell.

Many mammalian promoters are known in the art that may be used in conjunction with the expression cassette of the invention. Mammalian promoters often have a transcription initiating region, which is usually placed proximal to the 5' end of the coding sequence, and a TATA box, usually located 25 30 base pairs (bp) upstream of the transcription initiation site. The TATA box is thought to direct RNA polymerase II to begin RNA synthesis at the correct site. A mammalian promoter may also contain an upstream promoter element, usually located within 100 to 200 bp upstream of the TATA box. An upstream promoter element determines the rate at which transcription is initiated and can act in either orientation (Sambrook et al., "Expression of Cloned Genes in Mammalian Cells", in: Molecular Cloning: A Laboratory Manual, 2nd ed., 1989).

Mammalian viral genes are often highly expressed and have a broad host range; therefore sequences encoding mammalian viral genes often provide useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallothionein gene, also provide useful promoter sequences. Expression may be either constitutive or regulated.

A mammalian promoter may also be associated with an enhancer. The presence of an enhancer will usually increase transcription from an associated promoter. An enhancer is a regulatory DNA sequence that can stimulate transcription up to 1000-fold when linked to homologous or heterologous promoters, with synthesis beginning at the normal RNA start site. Enhancers are active when they are placed upstream or downstream from the transcription initiation site, in either normal or flipped orientation, or at a distance of more than 1000 nucleotides from the promoter. (Maniatis et al., Science, 236:1237 (1987); Alberts et al., Molecular Biology of the Cell, 2nd ed., 1989)). Enhancer elements derived from viruses are often times useful, because they usually have a broad host range. Examples include the SV40 early gene enhancer (Dijkema et al., EMBO J., 4:761 (1985) and the enhancer/promoters derived from the long terminal repeat (LTR) of the Rous Sarcoma Virus (Gorman et al., Proc. Natl. Acad. Sci. USA, 79:6777 (1982b)) and from human cytomegalovirus (Boshart et al., Cell, 41: 521 (1985)). Additionally, some enhancers are regulatable and become active only in the presence of an inducer, such as a hormone or metal ion (Sassone-Corsi and Borelli, Trends Genet., 2:215 (1986); Maniatis et al., Science, 236:1237 (1987)).

It is understood that many promoters and associated regulatory elements may be used within the expression cassette of the invention to transcribe an encoded protein or peptide. The promoters described above are provided merely as examples and are not to be considered as a complete list of promoters that are included within the scope of the invention.

The expression cassettes and vectors of the invention may contain a nucleic acid sequence for increasing the translation efficiency of an mRNA encoding a therapeutic agent of the invention. Such increased translation serves to increase production of the therapeutic agent. Because eukaryotic mRNA does not contain a Shine-Dalgamo sequence, the selection of the translational start codon is usually determined by its proximity to the cap at the 5' end of an mRNA. However, the nucleotides immediately surrounding the start codon in eukaryotic mRNA influence the efficiency of translation. Accordingly, one skilled in the art can determine what nucleic acid sequences will increase translation of a protein or peptide encoded by the expression cassettes and vectors of the invention.

Termination sequences can also be included in the cassettes and vectors of the invention. Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation (Birmstiel et al., Cell, 41:349 (1985); Proudfoot and Whitelaw, "Termination and 3' end processing of eukaryotic RNA", in: Transcription and Splicing (eds. B. D. Hames and D. M. Glover) 1988; Proudfoot, Trends Biochem. Sci., 14:105 (1989)). These sequences direct the transcription of an mRNA that can be translated into the polypeptide encoded by the DNA. Examples of transcription terminator/polyadenylation signals include those derived from SV40 (Sambrook et al., "Expression of cloned genes in cultured mammalian cells", in: Molecular Cloning: A Laboratory Manual, 1989).

As indicated above, nucleic acids encoding the therapeutic agents can be inserted into any convenient vector. Vectors that may be used include, but are not limited to, those that can be replicated in prokaryotes and eukaryotes. For example, vectors may be used that are replicated in bacteria, yeast, insect cells, and mammalian cells. Examples of vectors include plasmids, phagemids, bacteriophages, viruses, retroviruses, cosmids, and F-factors. However, specific vectors may be used for specific cells types. Additionally, shuttle vectors may be used for cloning and replication in more than one cell type. Such shuttle vectors are known in the art. The nucleic acid constructs or libraries may be carried extrachromosomally within a host cell or may be integrated into a host cell chromosome. Numerous examples of vectors are known in the art and are commercially available. (Sambrook and Russell, Molecular Cloning: A Laboratory Manual, 3rd edition (Jan. 15, 2001) Cold Spring Harbor Laboratory Press, ISBN: 0879695765; New England Biolab, Beverly, Mass.; Stratagene, La Jolla, Calif.; Promega, Madison, Wis.; ATCC, Rockville, Md.; CLONTECH, Palo Alto, Calif.; Invitrogen, Carlabad, Calif.; Origene, Rockville, Md.; Sigma, St. Louis, Mo.; Pharmacia, Peapack, N.J.; USB, Cleveland, Ohio). These vectors also provide many promoters and other regulatory elements that those of skill in the art may include within the nucleic acid constructs of the invention through use of known recombinant techniques.

Recombinant retroviruses can also be used which are constructed to carry or express at least one selected peptide of interest. Retrovirus vectors that can be employed include those described in EP 0 415 731; WO 90/07936; WO 94/03622; WO 93/25698; WO 93/25234; U.S. Pat. No. 5,219, 740; WO 93/11230; WO 93/10218; Vile and Hart, Cancer Res. 53:3860-3864 (1993); Vile and Hart, Cancer Res. 53:962-967 (1993); Ram et al., Cancer Res. 53:83-88 (1993); Takamiya et al., J. Neurosci. Res. 33:493-503 (1992); Baba et al., J. Neurosurg. 79:729-735 (1993); U.S. Pat. No. 4,777, 127; GB Patent No. 2,200,651; WO 91/02805; and EP 0 345 242.

Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles.

It is recognized that alphavirus-based vectors can be used that can function as gene delivery vehicles. Such vectors can be constructed from a wide variety of alphaviruses, including, for example, Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532). Representative examples of such vector systems include those described in U.S. Pat. Nos. 5,091,309; 5,217,879; and 5,185,440; and PCT Publication Nos. WO 92/10578; WO 94/21792; WO 95/27069; WO 95/27044; and WO 95/07994.

Gene delivery vehicles of the present invention can also employ parvovirus such as adeno-associated virus (AAV) vectors. Representative examples include the AAV vectors disclosed by Srivastava in WO 93/09239, Samulski et al., J. Vir. 63:3822-3828 (1989); Mendelson et al., Virol. 166:154-165 (1988); and Flotte et al., P.N.A.S. 90:10613-10617 (1993).

Representative examples of adenoviral vectors include those described by Berkner, Biotechniques 6:616-627 (Biotechniques); Rosenfeld et al., Science 252:431-434 (1991); WO 93/19191; Kolls et al., P.N.A.S.: 215-219 (1994); Kass-Eisler et al., P.N.A.S. 90:11498-11502 (1993); Guzman et al., Circulation 88:2838-2848 (1993); Guzman et al., Cir. Res. 73:1202-1207 (1993); Zabner et al., Cell 75:207-216 (1993); Li et al., Hum. Gene Ther. 4:403-409 (1993); Cailaud et al., Eur. J. Neurosci. 5:1287-1291 (1993); Vincent et al., Nat. Genet. 5:130-134 (1993); Jaffe et al., Nat. Genet. 1:372-378 (1992); and Levrero et al., Gene 101:195-202 (1992). Exemplary adenoviral gene therapy vectors employable in this invention also include those described in WO 94/12649, WO 93/03769; WO 93/19191; WO 94/28938; WO 95/11984 and WO 95/00655. Administration of DNA linked to killed adenovirus as described in Curiel, Hum. Gene Ther. 3:147-154 (1992), may be employed.

A nucleic acid construct, or an expression vector can also be inserted into any mammalian vector that is known in the art or that is commercially available, for example, as provided by CLONTECH (Carlsbad, Calif.), Promega (Madision, Wis.), or Invitrogen (Carlsbad, Calif.). Such vectors may contain additional elements such as enhancers and introns having functional splice donor and acceptor sites. Nucleic acid constructs may be maintained extrachromosomally or may integrate in the chromosomal DNA of a host cell. Mammalian vectors include those derived from animal viruses, which require trans-acting factors to replicate. For example, vectors containing the replication systems of papovaviruses, such as SV40 (Gluzman, Cell, 23:175 (1981)) or polyomaviruses, replicate to extremely high copy number in the presence of the appropriate viral T antigen. Additional examples of mammalian vectors include those derived from bovine papillomavirus and Epstein-Barr virus. Additionally, the vector may have two replication systems, thus allowing it to be maintained, for example, in mammalian cells for expression and in a prokaryotic host for cloning and amplification. Examples of such mammalian-bacteria shuttle vectors include pMT2 (Kaufman et al., Mol. Cell. Biol., 9:946 (1989)) and pHEBO (Shimizu et al., Mol. Cell. Biol., 6:1074 (1986)).

Methods for introduction of heterologous polynucleotides into mammalian cells are known in the art and include lipid-mediated transfection, dextran-mediated transfection, calcium phosphate precipitation, polybrene-mediated transfection, protoplast fusion, electroporation, encapsulation of -the polynucleotide(s) in liposomes, biollistics, and direct microinjection of the DNA into nuclei. The choice of method depends on the cell being transformed as certain transformation methods are more efficient with one type of cell than another. (Felgner et al., Proc. Natl. Acad. Sci., 84:7413 (1987); Felgner et al., J. Biol. Chem., 269:2550 (1994); Graham and van der Eb, Virology, 52:456 (1973); Vaheri and Pagano, Virology, 27:434 (1965); Neuman et al., EMBO J., 1:841 (1982); Zimmerman, Biochem. Biophys. Acta., 694: 227 (1982); Sanford et al., Methods Enzymol., 217:483 (1993); Kawai and Nishizawa, Mol. Cell. Biol, 4:1172 (1984); Chaney et al., Somat. Cell Mol. Genet., 12:237

(1986); Aubin et al., Methods Mol. Biol., 62:319 (1997)). In addition, many commercial kits and reagents for transfection of eukaryotic cells are available.

Following transformation or transfection of a nucleic acid into a cell, the cell may be selected for the presence of the nucleic acid through use of a selectable marker. A selectable marker is generally encoded on the nucleic acid being introduced into the recipient cell. However, co-transfection of selectable marker can also be used during introduction of nucleic acid into a host cell. Selectable markers that can be expressed in the recipient host cell may include, but are not limited to, genes that render the recipient host cell resistant to drugs such as actinomycin $C_1$, actinomycin D, amphotericin, ampicillin, bleomycin, carbenicillin, chloramphenicol, geneticin, gentamycin, hygromycin B, kanamycin monosulfate, methotrexate, mitomycin C, neomycin B sulfate, novobiocin sodium salt, penicillin G sodium salt, puromycin dihydrochloride, rifampicin, streptomycin sulfate, tetracycline hydrochloride, and erythromycin. (Davies et al., Ann. Rev. Microbiol., 32: 469 (1978)). Selectable markers may also include biosynthetic genes, such as those in the histidine, tryptophan, and leucine biosynthetic pathways. Upon transfection or transformation of a cell, the cell is placed into contact with an appropriate selection agent.

The expression cassettes may further comprise a selectable suicide gene, such as thymidine kinase (TK), which allows negative selection of grafted cells upon completion of treatment or in the event of undesired complications. TK-expressing cells can be negatively selected by the administration of gancyclovir according to methodology known in the art. Alternatively, the cassette may encode cytosine deaminase, which causes the cells to die in the presence of added 5-fluorocytosine. The expressed gene can be lethal as a toxin or lytic agent.

It is recognized that the OEC may be isolated and modified by genetic modification prior to delivery to a site of interest. See, for example, Nabel et al. 1989 Science 244:1342-1344; Wilson et al. 1989 Science 244:1344-1346; Iwaguro et al. 2002 Circulation 105:732-738; Jevrumovic et al. 2004 Am J Physiol Heart Circ Physiol 287:H494-500; all of which are herein incorporated by reference.

Laboratory and Clinical Uses

The invention also encompasses methods for the identification and isolation of additional peptides capable of specifically binding OEC. The peptides can be isolated by the methods set forth herein. Phage display technology is well-known in the art and can be used to identify candidate peptides from a library of diverse peptides. Phage display describes a selection technique in which a library of variants of a peptide or protein is expressed on the outside of a phage virion, while the genetic material encoding each variant resides on the inside (Sidhu et al. (2003) *Chembiochem*, 4:14-25; Ferrer et al. (1999) *J. Pept. Res.*, 54:32-42; and, BouHamdan et al. (1998) *J. Biol. Chem.* 273:8009-8016). This creates a physical linkage between each variant protein sequence and the DNA encoding it, which allows rapid partitioning based on binding affinity to a given target molecule (antibodies, enzymes, cell-surface receptors, etc.) by an in vitro selection process called "panning" or "biopanning" (Whaley et al. (2000) *Nature* 405:665-668). Panning methods can include, for example, solution phase screening, solid phase screening, or cell-based screening.

In its simplest form, panning is carried out by incubating a library of phage-displayed peptides with a plate (or bead) coated with the target, washing away the unbound phage, and eluting the specifically bound phage. The eluted phage is then amplified and taken through additional binding/amplification cycles to enrich the pool in favor of binding sequences. After 3-4 rounds, individual clones are characterized by DNA sequencing and ELISA. Once a candidate peptide is identified, directed or random mutagenesis of the sequence may be used to optimize the binding properties of the peptide.

In another embodiment, antibodies can be raised against the peptides of the invention. These antibodies can be used to isolate or identify OECs by contacting the antibody with a population of cells that has been incubated with a sufficient amount of one or more of the OEC-binding peptides disclosed herein. The antibodies can be free in solution or bound to a solid support as discussed infra. Methods for producing antibodies are well known in the art (see, for example, Harlow and Lane (1988) "Antibodies: A Laboratory Manual," Cold Spring Harbor Laboratory, Cold Spring Harbor, N.Y.; U.S. Pat. No. 4,196,265).

OECs can be also be identified and/or purified by contacting the cells with the OEC-binding peptides of the invention. The specific and selective binding of the OECs to the peptide(s) permits the OECs to be sufficiently distinguished from contaminating cells that do not express the peptide-binding antigen. The term purified as applied to the endothelial precursor cell population utilized herein means that the population is significantly enriched in endothelial precursor cells relative to the crude population of cells from which the endothelial precursor cells are isolated. The peptides can be part of one or more reagents or kits suitable for these purposes.

When used for isolating and/or characterizing the populations of OECs, the peptides of the invention can be conjugated with labels that expedite identification and separation of the OECs from other cells in a population or sample. Examples of such labels include magnetic beads, biotin, which may be removed by avidin or streptavidin, fluorochromes, which may be used in connection with a fluorescence-activated cell sorter, and the like.

In one embodiment, the peptide is attached to a solid support. Some suitable solid supports include nitrocellulose, agarose beads, polystyrene beads, hollow fiber membranes, and plastic petri dishes. For example, the molecule can be covalently linked to Pharmacia Sepharose 6 MB macro beads. The exact conditions and duration of incubation for the solid phase-linked peptides with the crude cell mixture will depend upon several factors specific to the system employed, as is well known in the art. Cells that are bound to the peptide are removed from the cell suspension by physically separating the solid support from the cell suspension. For example, the unbound cells may be eluted or washed away with physiologic buffer after allowing sufficient time for the solid support to bind the OECs.

The bound cells are separated from the solid phase by any appropriate method, depending mainly upon the nature of the solid phase. For example, bound cells can be eluted from a plastic petri dish by vigorous agitation. Alternatively, bound cells can be eluted by enzymatically "nicking" or digesting an enzyme-sensitive "spacer" sequence between the solid phase and the peptide (or an antibody raised against the peptide as discussed supra). Suitable spacer sequences bound to agarose beads are commercially available, for example, from Pharmacia.

The eluted, enriched fraction of cells may then be washed with a buffer by centrifugation and preserved in a viable state at low temperatures for later use according to conventional technology. The cells may also be used immediately, for example by being infused intravenously into a recipient.

The peptides disclosed herein may also be used to identify and/or purify OECs by means of flow cytometry, for example by means of a fluorescence-activated cell sorter (FACS), such as those manufactured by Becton-Dickinson under the names FACScan or FACSCalibur. By means of this technique, OECs are tagged with a particular fluorescent dye (i.e., "stained") by means of one or more peptides of the invention which have been conjugated to such a dye. When the stained cells are placed on the instrument, a stream of cells is directed through an argon laser beam that excites the fluorochrome to emit light. This emitted light is detected by a photo-multiplier tube (PMT) specific for the emission wavelength of the fluorochome by virtue of a set of optical filters. The signal detected by the PMT is amplified in its own channel and displayed by a computer in a variety of different forms—e.g., a histogram, dot display, or contour display. Thus, fluorescent cells which emit at one wavelength express a molecule that is reactive with the specific fluorochrome-labeled peptide, whereas non-fluorescent cells do not express this molecule. The flow cytometer is also semi-quantitative in that it displays the amount of fluorescence (fluorescence intensity) expressed by the cell. This correlates, in a relative sense, to the number of the peptide-binding molecules expressed by the cell.

Fluorochromes which are typically used with FACS machines include fluorescein isothiocyanate (FITC), which has an emission peak at 525 nm (green), R-phycoerythrin (PE), which has an emission peak at 575 nm (orange-red), propidium iodide (PI), which has an emission peak at 620 nm (red), 7-aminoactinomycin D (7-AAD), which has an emission peak at 660 nm (red), R-phycoerythrin Cy5 (RPE-Cy5), which has an emission peak at 670 nm (red), and allophycocyanin (APC), which has an emission peak at 655-750 nm (deep red).

These and other types of FACS machines may have the additional capability to physically separate the various fractions by deflecting the cells of different properties into different containers.

In another embodiment, OECs are concentrated (or "enriched") from blood or blood products. In this manner, blood is withdrawn directly from the circulating peripheral blood of a donor and percolated continuously through a column containing the solid phase-linked binding molecule, such as an OEC-binding peptide, to capture OECs. The OEC-depleted blood is returned immediately to the donor's circulatory system by methods known in the art, such as hemapheresis. The blood is processed in this way until a sufficient number of progenitor cells binds to the column. The stem cells are then isolated from the column by methods known in the art. This method allows rare OECs to be harvested from a very large volume of blood. Transplantation of new cells into the damaged blood vessels has the potential to repair damaged vascular tissue, e.g., veins, arteries, capillaries, thereby restoring vascular function.

The following examples are offered by way of illustration and not by way of limitation.

EXPERIMENTAL

Introduction

Progenitor cell-based regenerative strategies offer new perspectives in cell therapies and tissue engineering for achieving an effective revascularization of ischemic or injured tissues. Asahara et al. (1997) first described that peripheral blood contains a small subset of circulating bone marrow derived cells termed endothelial progenitor cells (EPC). Recent reports from in-vitro studies underline the observation that so-called EPC represent a heterogeneous population of cells with different capacities to assume a differentiated and functional endothelium phenotype in-vitro or with respect to proliferation (Gulati et al. 2003a; Gulati and Simari 2004; Rehman et al. 2003). Cultures from peripheral blood contain cells termed early-EPC that share some endothelial but also monocytic characteristics and exhibit a restricted capacity of expansion. Another cell population isolated from peripheral blood cultures is the so called late-EPC or blood outgrowth endothelial cells (BOEC) that have a cobblestone morphology characteristic of an endothelial phenotype. Furthermore, these cells express several endothelial markers and have high proliferative capacity (Lin et al. 2000).

Endothelial progenitors have been implicated in myocardial repair after infarction, in the propagation of angiogenesis following ischemia, and in vascular repair after injury (Gulati et al. 2003b; Hajitou et al. 2006; Iwakura et al. 2003). In spite of the enormous therapeutic potential of these cells, the molecular characteristics and EPC biology are incompletely understood. Endothelial progenitor cell-specific markers are needed to facilitate the development of future progenitor therapies which may be either pharmacological or device based. Towards this end, phage display technology was used to identify new peptide ligands that bind with high affinity and specificity to human blood outgrowth endothelial cells (HBOEC).

Since the invention of phage display systems in 1985 (Smith 1985), display technologies have proven to be a valuable tool for a variety of biological, clinical and biotechnological applications (Ballard et al. 2006a; Ballard et al. 2006b; Edelberg et al. 2004; Smith and Petrenko 1997). These include the characterization of receptor- and antibody-binding sites, the study of protein ligand interactions, and the isolation and evolution of proteins or enzymes exhibiting improved or otherwise altered binding characteristics with their ligands. Phage display screening relies on the use of chimeric proteins that consist of a target sequence fused to a phage coat protein to achieve display. Using standard molecular biology techniques, the DNA sequence of the inserted region can be randomized to create a library of phage, each of which will synthesize a different version of the chimera on its surface. By incubating the library with a target of interest, washing out weak or non binders, and repeating the process to enrich for tight binders, a subset can be selected from the original library exhibiting the ability to tightly interact with the desired target. This in vitro selection process is known as biopanning Because the chimera is encoded within the phage genome the identity of the selected sequences, e.g., their amino acid composition can be deduced by DNA sequencing.

Biopanning on whole cells with no directive pressures on the selective scheme has many advantages: the receptors are more likely to be in their native conformation, with all their natural posttranslational modifications, and neither purification nor prior knowledge of a particular target receptor is required. An additional strength of this approach is that it is highly inductive, in that it does not rely on knowledge of which cell surface molecules are present, their concentration, or their specificity. Furthermore, this approach ensures that the selected peptide sequence binds to its target in the presence of many other biological macromolecules and allows for selection of membrane proteins that are often difficult to express and purify.

Materials and Methods

Isolation of Human Blood Outgrowth Endothelial Cells from Peripheral Blood:

The use of human material described in this study was approved by the responsible ethical committee. Fresh blood was collected from healthy volunteer donors by venipuncture and anticoagulated with buffered sodium citrate. The anticoagulated blood was diluted 1:1 with HBSS (Sigma-Aldrich)

containing 1 mM EDTA and 0.5% BSA. Buffy coat mononuclear cells were obtained from diluted blood by density gradient centrifugation method using Histopaque 1077 (Sigma-Aldrich) (Lin et al. 2000). The cells were washed in PBS three times at 400 g for 10 min before culturing. Buffy coat mononuclear cells from 100 ml peripheral blood were resuspended in EGM-2 medium (endothelial cell growth medium 2; Cambrex Bioscience, Walkersville, Md.) without further subpopulation enrichment procedures and placed into one well of a six well plate coated with type 1 collagen (BD Biosciences, Bedford, Mass.). The plate was incubated at 37° C. in a humidified environment with 5% $CO_2$. Non adherent cells were removed after 48 hours and every second day thereafter. Colonies with cobblestone morphology appeared after 3-4 weeks in culture. These cells were cultured until they formed larger colonies. Colonies were selected, trypsinized, and expanded over several passages by using standard cell culture procedures.

Isolation of Human Lymphocytes and Neutrophils:

Lymphocytes and neutrophils were obtained from the same preparation. Lymphocytes were collected from the supernatant of the cultured buffy coat mononuclear cells that were allowed to adhere for 48 hours. The cell concentration was adjusted to $1.10^5$ cells per ml.

Neutrophils were collected from the lower portion of the density gradient preparation. The upper layers were removed and processed as described above. The neutrophil-rich Histopaque layer was transferred to a centrifuge tube and diluted in fresh RPMI to wash the cells free of Histopaque. The suspension was centrifuged at 700×g for 15 min at room temperature. The supernatant was aspirated and the pellet resuspended in 10 ml of RPMI and centrifuged at 700×g for 10 min at room temperature. Contaminating red cells were lysed by quickly re-suspending the pellet in sterile water at 4° C. After 30 sec an equal volume of 1.8% saline solution was added in order to return the solution to isotonicity. The suspension was then centrifuged for 10 min at 250×g at 4° C. The cell lysis step was repeated. The final pellet was re-suspended and concentration adjusted to $1.10^5$ cells per ml.

Human Umbilical Vein Endothelial Cells (HUVEC):

HUVEC were from the American Type Culture Collection (ATCC, Manassas, Va.). Passages 4 to 8 were used in this study. HUVEC were cultured in EGM-MV medium (Cambrex) at 37° C. in an incubator with humid atmosphere and 5% $CO_2$.

Peripheral blood human HL-60 promyelocytic cells from the American Type Culture Collection (ATCC) were cultured in RPMI 1640 medium supplemented with 20% fetal bovine serum.

Biopanning Procedure

Cells at 80% confluence were detached by treating with 0.05% trypsin-EDTA, washed once with EGM-2 medium and resuspended in EGM-2 containing 1% BSA at $1.10^5$ cells per ml. In the pre-clearing step, 1 ml of HUVEC suspension at $1.10^5$ cells per ml were incubated with 10 µl of PhD-12 peptide phage display system (New England Biolabs, Beverly, Mass.) within 1.5 ml Eppendorf tube for 2 hours at 4° C.; the mixture was then centrifuged. In the screening step, the unbound phage pool remaining in the supernatant was transferred to a fresh tube and incubated with 1 ml of HBOEC at $1.10^5$ cells per ml. After 1 hour incubation at 4° C., the cell-phage complexes were separated by centrifugation. Following five intensive washes with TBS-0.5% Tween-20 buffer the bound phage was non-specifically eluted with 0.2 M Glycine-HCl buffer (pH 2.2) for 10 min. The eluate was immediately neutralized by 1M Tris.HCl buffer (pH 9.0). An aliquot of the eluted phage was used for determining titer by plaque assay. The rest of the phage eluate was amplified in mid-log phase E. coli ER2738 (New England Biolabs), and purified by precipitation with polyethylene glycol. An aliquot of the amplified phage was subsequently re-applied to newly trypsinized cells for a total of three biopanning rounds and two amplification steps.

DNA Sequencing

After three rounds of biopanning E. Coli ER2738 were infected with the recovered phage and then plated onto LB agar plates. Single phage colonies were picked and amplified in LB medium. DNA was purified and sequenced by using a primer hybridizing to −96 position of the insert following the manufactures instructions. DNA sequencing was performed by the UNC-CH Genome Analysis Facility (Chapel Hill, N.C.).

Homogeneous Phage Recovery

Once isolated individual phage clones were subjected to evaluation of relative binding. High titer stocks of homogeneous phage were generated. Serially diluted phage ($1.10^9$ pfu, $1.10^{10}$ pfu, and $1.10^{11}$ pfu) were incubated with HBOEC ($1.10^5$ cells) for 1 h at 4° C. and then subjected to the same wash protocol used for the selection experiments. In parallel the same procedure was carried in a blocked Eppendorf tube without HBOEC to test for non specific binding for each selected sequence to the plastic container. Binding ratio is defined as recovery of phage bound to the target cells normalized to the recovery of phage non-specifically bound to the plastic.

Assaying for Binding Specificity

The specificity of HBOEC-selected phage clones was determined by biopanning on a panel of other cell types. The biopanning procedure was carried as described above with the exception of including the pre-clearing incubation step.

Immunofluorescence Staining:

Cells were seeded on glass cover slips coated with rat tail collagen in 12-well plates. Cells were incubated at 37° C. for 30 min prior to fixation with 10 mg/ml DiI-Ac-LDL (acetylated low density lipoprotein DiI complex; Molecular Probes). After fixation with 4% paraformaldehyde, cells were permiabilized with 0.1% Triton-X in PBS. Cells were then incubated with rabbit anti-human vWF antibody (von Willebrand Factor; DACO) in PBS-1% BSA, and then with secondary antibody coupled with AlexaFluor 488 (Molecular Probes). Cell nuclei were counter stained with DAPI (Sigma-Aldrich).

Peptide Synthesis:

All active and control peptide sequences were synthesized using standard FMoc chemistry by solid phase peptide synthesizer (Commonwealth Biotech. Inc., Richmond, Va.). The peptides were purified by HPLC and chemical purity was confirmed by mass spectrometry (MALDITOF).

Proliferation Assay:

Cell proliferation assays were performed in triplicate in 12-well culture plates. HBOEC (2000 cells per well) were plated and grown overnight in EGM-2 supplemented with 2% FBS. Cells were quiesced in EBM-2 medium containing 0.5% FBS for 16 h. Cells were re-fed with medium containing escalating concentrations of free peptides. Cell proliferation at 12 h, 36 h, and 96 h was determined by total and viable cell counts by Trypan blue exclusion. Proliferation was normalized to the cell number before the addition of free peptides.

In Vitro Tube Formation Assay:

For the angiogenesis and cell migration assays, cells were detached with 1 mM EDTA (Sigma-Aldrich) to avoid cell membrane antigen proteolysis. After detachment, HBOEC were incubated with peptides in a dose dependent manner, seeded on Matrigel matrix in 96-well plate (10000 cells per well) and cultured for 6 hours at 37° C. with 5% CO2. Capillary-like structures were examined by phase contrast microscopy and digital images were taken and quantified by computer assisted analysis.

Cell Migration Assay:

HBOEC migration was measured by using a 48-well Boyden chamber with 8 μm pore-size filters. EDTA-detached-HBOEC were incubated with peptides in a dose dependent manner and seeded at a density 5000 cells per well. Recombinant human VEGF (25 ng/ml, R&D systems) was diluted in EBM-2 medium supplemented with 2% FBS and placed in the lower chamber. Cells were incubated at 37° C. for 12 hours.

Response to VEGF Assay:

Response to VEGF assays were performed in triplicate in 12-well culture plates. HBOEC (2000 cells per well) were plated and grown overnight in EGM-2 supplemented with 2% FBS. Cells were quiesced in EBM-2 medium containing 0.5% FBS for 16 h. Cells were re-fed with medium containing escalating concentrations of free peptides, VEGF (25 ng/ml) and 2% FBS in EBM-2 medium. Cell proliferation for 96 h and total and viable cell counts were determined by Trypan blue exclusion. Cell numbers were normalized to conditions without VEGF.

Synthesis of Peptide Modified Terpolymers:

Peptide sequences were immobilized to methacrylic terpolymers via one step chain transfer controlled free radical polymerization as described by Fussell and Cooper (Fussell 2004a and Fussell 2004b). The monomers used in the reactions were n-hexyl methacrylate (HMA) (Alfa Aesar, Ward Hill, Mass.), methyl methacrylate (MMA) (ACROS Organics, Pittsburgh, Pa.), and methacrylic acid (MAA) (ACROS Organics, Pittsburgh, Pa.), with 2,2-azobisisobutyronitrile (AIBN) (Aldrich Chemical, Milwaukee, Wis.) as the initiator. The molar ratio of the monomers in the reaction mixture was HMA:MMA:MAA—20:78:2. The peptides were added with the monomers after the solvent was purged with argon. The reaction temperature for the polymerization was 55-60° C. and reactions were carried out overnight.

Amino Acid Analysis:

The amount of peptide incorporation was determined from amino acid analysis performed by Commonwealth Biotechnologies, Inc. (Richmond, Va.).

Cell Binding Assay:

Peptide grafted materials were coated on round microscope cover glass slides. Glass slides were sterilized by immersion in 70% ethanol. After washing with PBS, the cover slips were placed in tissue culture polystyrene plates and incubated with an HBOEC suspension in serum free medium at a concentration $1 \times 10^4$ cells/ml. After two hours of incubation, medium was aspirated, loosely attached cells were washed with PBS and the cells were fixed with 4% paraformaldehyde. Cell nuclei were stained with DAPI and examined under fluorescent microscope. Digital images were taken from 15 random fields per sample and quantified by computer assisted analysis.

Data Analysis:

Data are representative of at least three independent experiments and quantitative analyses are presented as means±SD. Statistical analysis, where applicable, was performed in Microsoft Excel. A two-tailed unpaired Student's t-test was used to compare the differences. A value of P<0.05 was considered statistically significant.

Results

Identification of Phage Clones that Bind HBOEC:

The strategy adopted for selection of peptide ligands that bind specifically to HBOEC involved a two-step biopanning procedure as outlined on FIG. 1A. First, to decrease non-specific binding the phage library was pre-cleared with non-HBOEC. The phage library was incubated with HUVEC and centrifuged to separate HUVEC-phage complexes and unbound phage clones. Second, the unbound phage pool was incubated with HBOEC for 1 hour at 4° C. After stringent washing, the phage that bound to HBOEC were harvested and amplified back to the original input titer of the library and used for subsequent rounds of biopanning. After three rounds of selection, individual phage were isolated and the peptide ligand sequences were determined for 40 randomly chosen phage clones. Thirty-eight different peptide sequences were deduced and two phage clones contained no inserts. The sequencing results are summarized in Table 1. The population of peptides contained a number of potential consensus motifs. By scoring the most commonly observed amino acids at each position, the primary consensus sequence, SPTPS(P/L)PP-SAGG (SEQ ID NO:39), was determined. Although this individual peptide was not isolated in the screen, the consensus motifs TPS and PPS appeared in the isolated peptide ligands (see Table 1). Analysis of peptide sequences using BLAST (Altschul et al. 1997), identified a number of different homologies listed in Table 2.

Homogeneous Phage Recovery

Figure 1B:
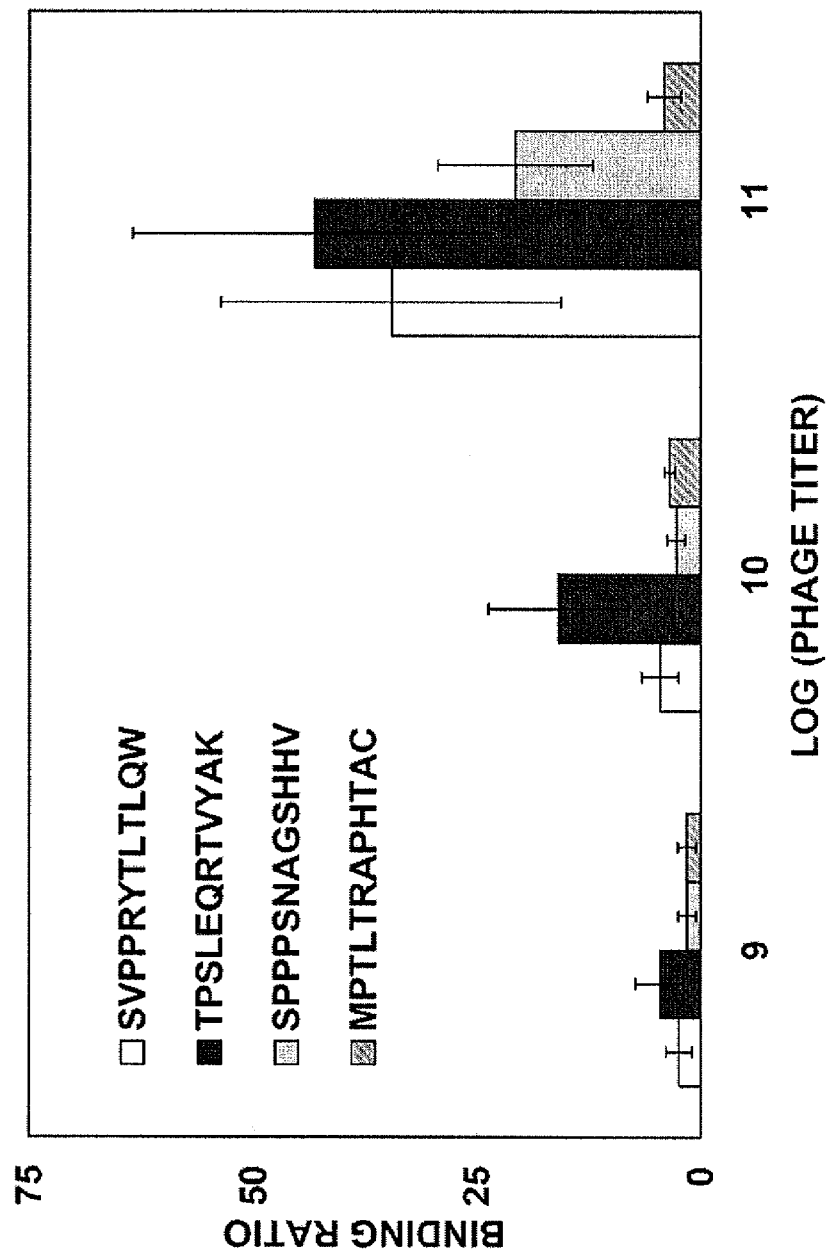
FIG. 1B shows a concentration dependence of four selected phage clones (SEQ ID NO:7, white bar; SEQ ID NO:17, dark gray bar; SEQ ID NO:32, light gray bar; SEQ ID NO:37, gray striped bar), binding to human blood OEC (HBOEC); Homogeneous phage at the indicated concentrations were biopanned on HBOEC for 1 hour at 4° C. Values showing the mean±standard deviation from triplicate determinations.

After selection of putative HBOEC specific ligands, pure high titer stocks of homogeneous phage were generated for further assessment of binding characteristics. The initial analysis, disclosed herein, includes four phage clones: SVP-PRYTLTLQW (SED ID NO:7), TPSLEQRTVYAK (SEQ ID NO:17), SPPPSNAGSHHV (SEQ ID NO:32), and MPTL-TRAPHTAC (SEQ ID NO:37) bearing different consensus motifs (see also Table 1). FIG. 1B, shows the concentration dependence of homogeneous recovery for the selected phage clones. It is seen from the figure that all four ligands bind HBOEC over a range of concentrations in a dose-dependent manner. The highest recovery is displayed by the phage expressing the TPSLEQRTVYAK (SEQ ID NO:17) peptide. This finding suggests either higher affinity for the TPSLEQRTVYAK (SEQ ID NO:17) ligand or availability of more binding sites on the HBOEC surface. The lowest affinity/avidity was exhibited by a ligand containing the MPT motif.

Figure 2:
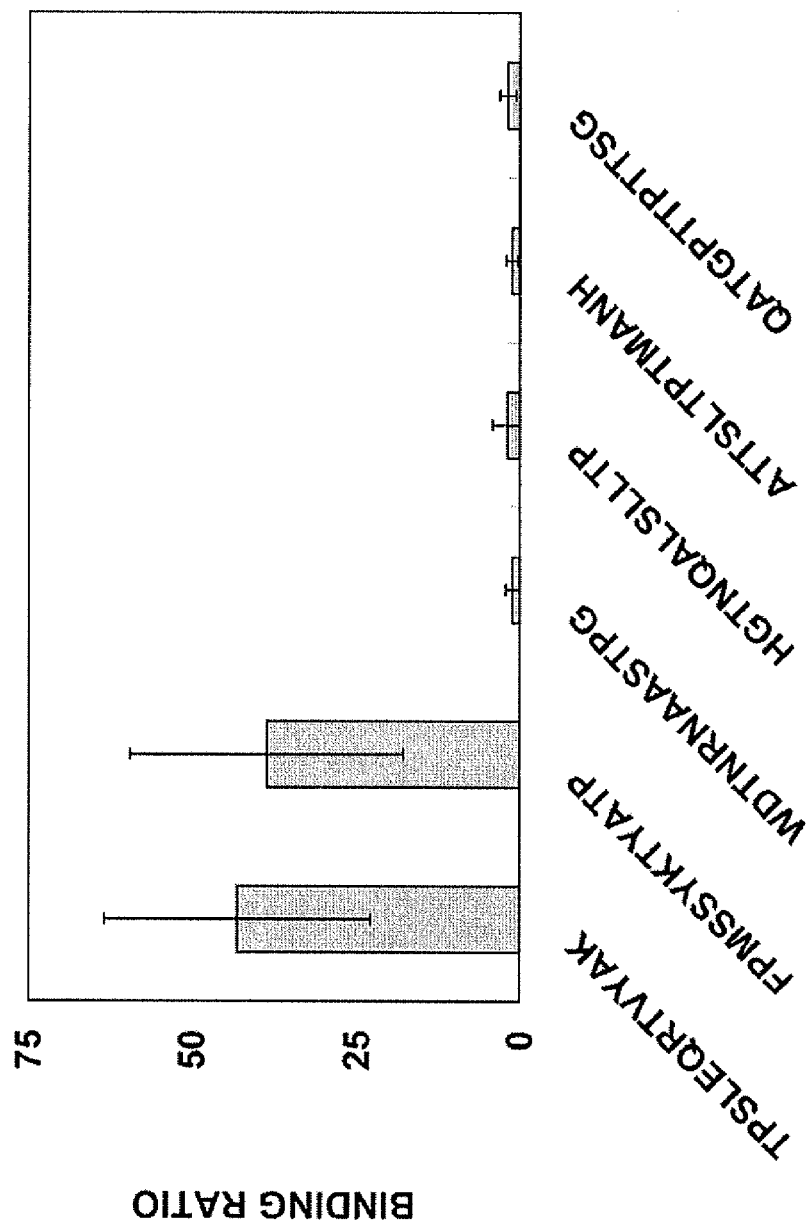
FIG. 2 exhibits binding of ligands containing TP(S/T/G) motif (from left to right, SEQ ID NO:17, 19, 21, 13, 15, and 16). $1.10^{11}$ of homogeneous phage were biopanned on HBOEC for 1 hour at 4° C. All determinations were performed at least three times and the data are shown as mean±standard deviation.

Next, the question of whether the consensus motif in a sequence determines ligand binding was addressed. Homogeneous recovery was examined in a group of phage bearing the TP(S/T/G) motif. HBOEC ($1 \cdot 10^5$ cells) were biopanned on $1 \cdot 10^{11}$ pfu of homogeneous phage. FIG. 2 shows different recoveries. Although some phage demonstrate lower recovery and therefore lower affinity/avidity for HBOEC, other phage display higher recoveries. Again the phage expressing the TPSLEQRTVYAK (SEQ ID NO:17) peptide ligand showed the highest recovery, having a binding ratio of 43±20. The binding profile on FIG. 2 demonstrates that recovery may not be determined solely by the consensus motif and that the amino acids flanking the consensus motif may impact binding interactions as well.

Cell Specificity

Figure 3:
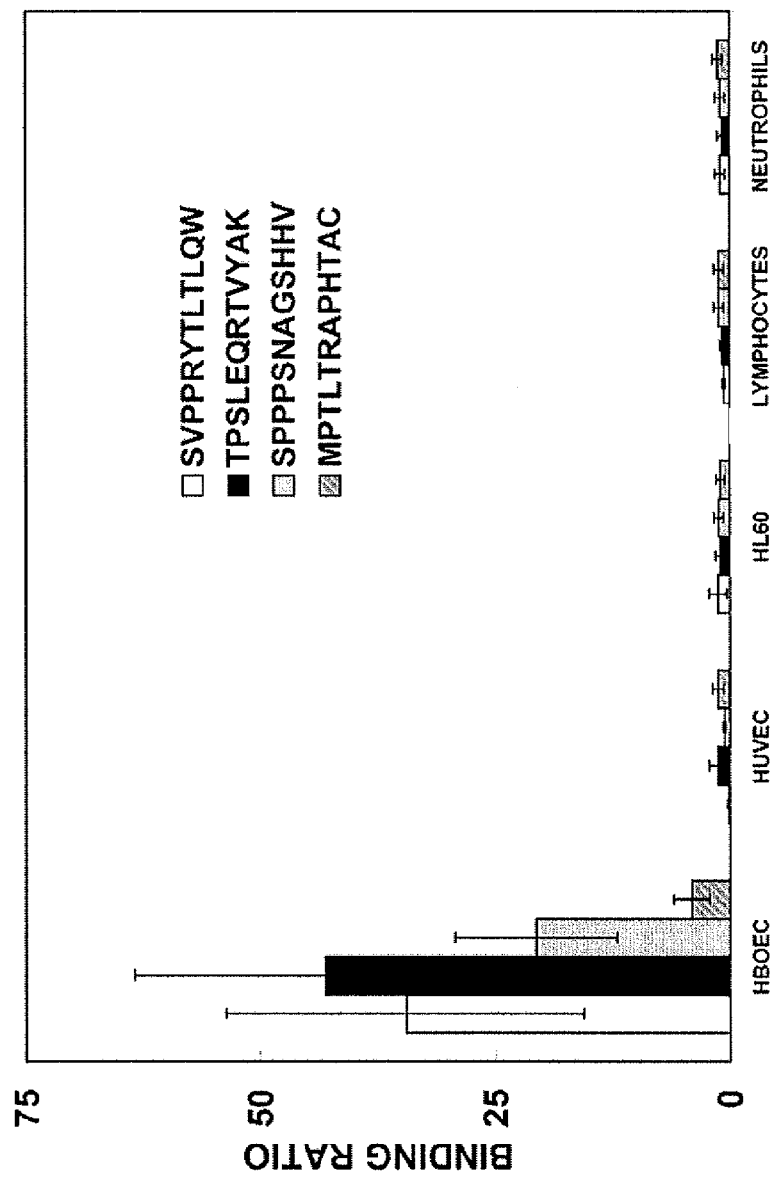
FIG. 3 displays cell specificity of ligands selected by biopanning on HBOEC (SEQ ID NO:7, white bar; SEQ ID NO:17, dark gray bar; SEQ ID NO:32, light gray bar; SEQ ID NO:37, gray striped bar). Specificity determinations used inputs of $1.10^{11}$ phage and incubations of 1 hour at 4° C. Values showing the mean±standard deviation of triplicate determinations.

While phage clones expressing the SVPPRYTLTLQW (SED ID NO:7), TPSLEQRTVYAK (SEQ ID NO:17), SPPP-SNAGSHHV (SEQ ID NO:32), and MPTLTRAPHTAC (SEQ ID NO:37) ligands demonstrate good recoveries, there is no assurance that the selected sequences will exhibit specificity for the target cells. To assess cell specificity, the above phage clones were screened against a panel of other cell types. FIG. 3 shows the specificity profile of the selected phage clones. No significant recovery is seen for any of the clones for the cell types tested except for the target cells.

Functional Characterization of Phage Display Selected Ligands on a Peptide Level.

To examine the effect of phage display-selected peptide ligands on endothelial cell function, free peptides were synthesized by a solid phase peptide technology. The C-terminus of the active peptides was extended with a Gly-Gly-Gly-Ser linker (SEQ ID NO:40) followed by an additional cysteine.

Figure 4:
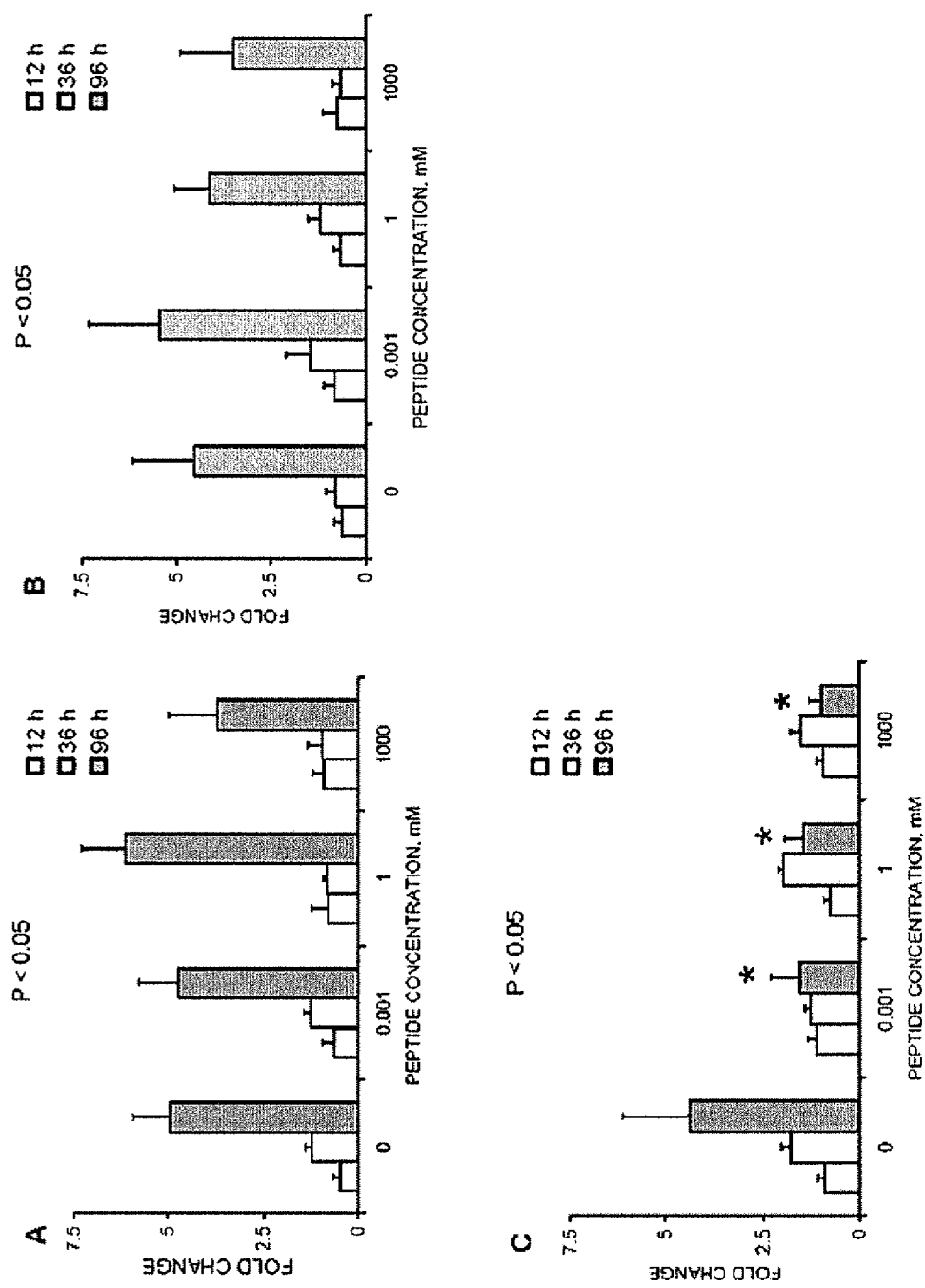
FIG. 4 demonstrates the functional characterization on a peptide level. HBOEC were incubated with the phage display-identified peptides in a dose-dependent manner and proliferation was monitored over time. A. TPS-peptide. B. SYQ-peptide. C. SWD-peptide.
Figure 5:
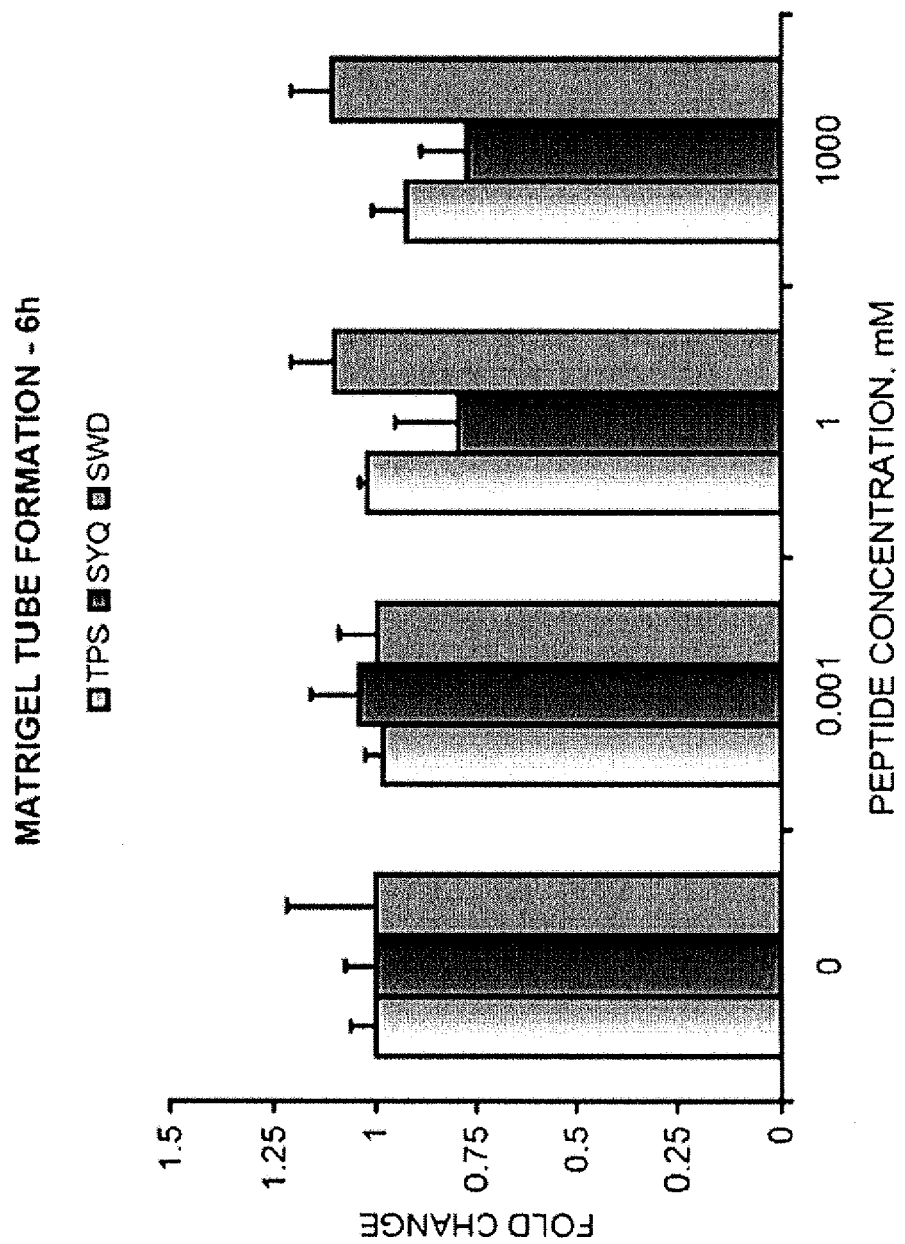
FIG. 5 represents the quantification of the tube formation ability of the HBOEC-synthetic peptide complexes as a function of peptide concentration. HBOEC were incubated with the phage display-identified peptides in a dose-dependent manner and tube formation was monitored after 6 hours.
Figure 6:
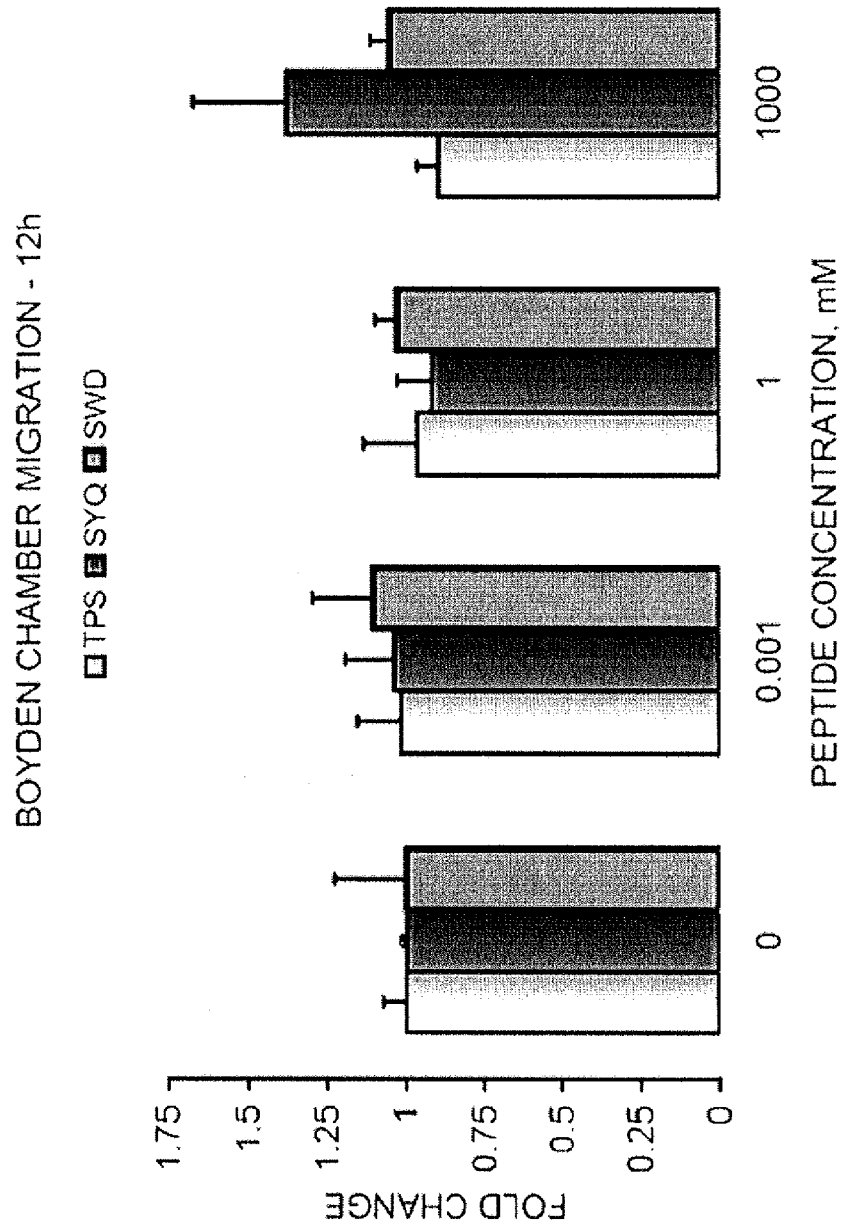
FIG. 6 represents the quantification of the migration ability of the HBOEC-synthetic peptide complexes as a function of peptide concentration. HBOEC were incubated with the phage display-identified peptides in a dose-dependent manner and migration in a Boyden chamber assay was monitored after 12 hours.
Figure 7:
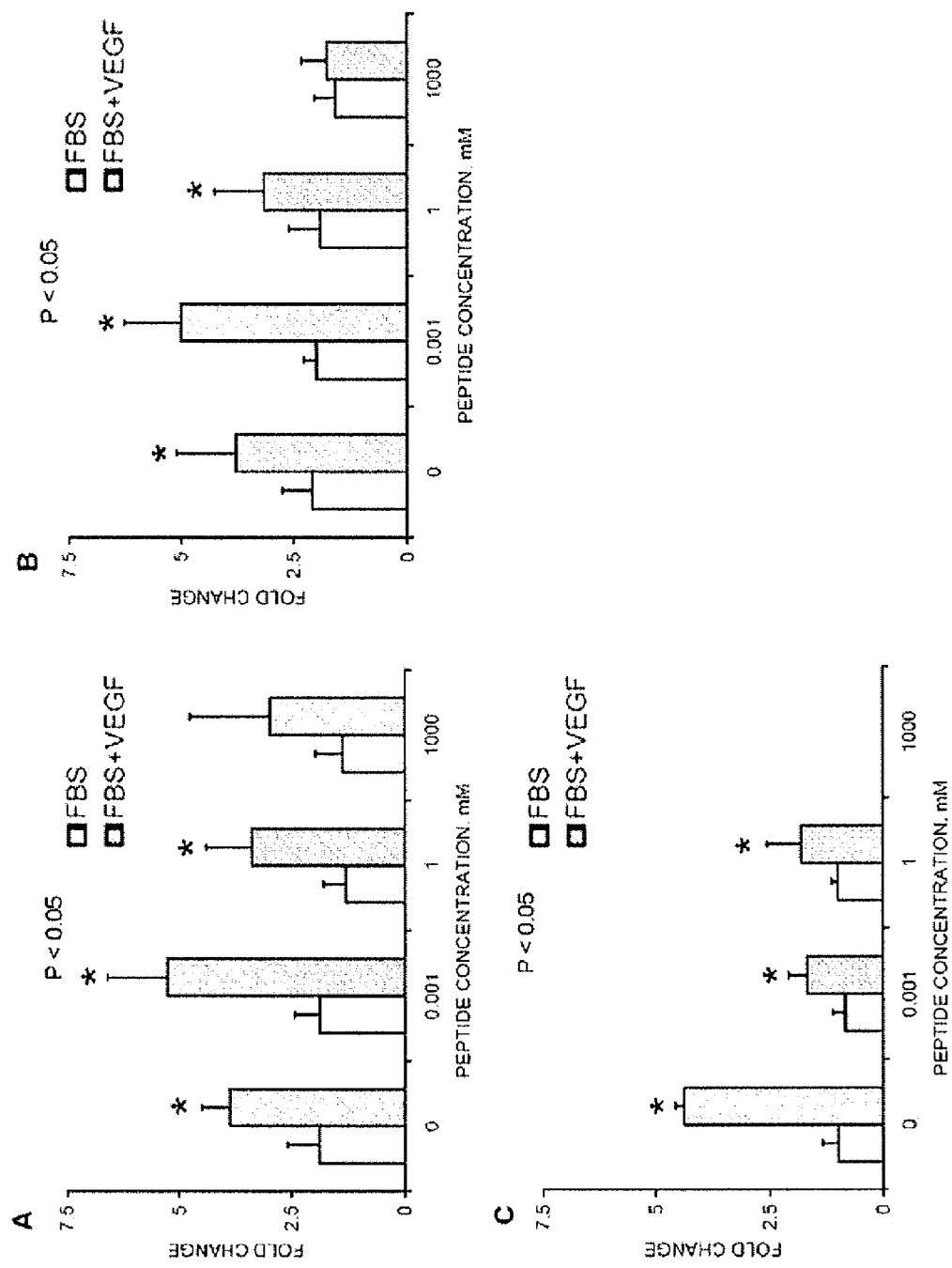
FIG. 7 represents the quantification of response to VEGF. HBOEC were incubated with the phage display-identified peptides in a dose-dependent manner and their response to VEGF was monitored after 96 hours. A. TPS-peptide. B. SYQ-peptide. C. SWD-peptide.

Proliferation data of HBOEC incubated with increasing concentrations of free peptides are presented in FIG. 4. The results from the tube formation, migration, and response to VEGF assays are shown in FIGS. 5, 6, and 7 respectively. As can be seen from these figures, the TPS- and SYQ-peptides supported endothelial cell function while the SWD-peptide displayed apoptotic properties and caused cell death. Thus only the TPS- and SYQ-peptides were used in subsequent studies to develop peptide grafted synthetic materials.

Functional Characterization of Immobilized Peptides to Optimized Biomaterials in In Vitro Assays of Cell Binding.

Figure 8:
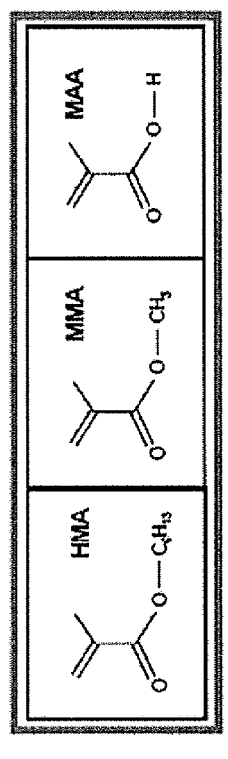
FIG. 8 represents the functional characterization of peptides immobilized to a biomaterial surface and the design of peptide modified bioactive materials. A. Hexylmethacrylate (HMA), methylmethacrylate (MMA), and methacrylic acid (MAA) were used to synthesize methacrylic terpolymers via free radical polymerization reaction. B. Peptide sequences were attached using chain transfer chemistry with terminal cysteine residue serving as a chain transfer agent. C. Bar graph quantifying cell attachment of HBOEC on peptide modified HMA:MMA:MAA terpolymer films. RGE-modified terpolymer surfaces were used as a negative control; Fibronectin (FN) coated wells were used as a positive control. SYQ and TPS denote HBOEC specific peptides identified by phage display selection. The cell-adhesive RGD peptide was included in the study as well. The peptide density in all materials is similar, around 2 μmol peptide per gram terpolymer as determined by amino acid analysis. D. Bar graph quantifying cell attachment of HUVEC on peptide modified HMA:MMA:MAA terpolymer films.
Figure 8:
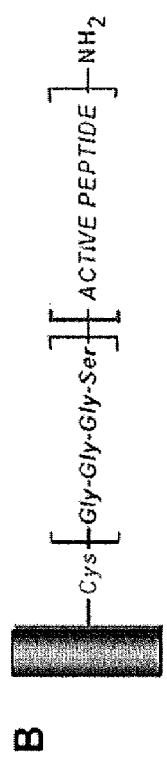
Figure 8:
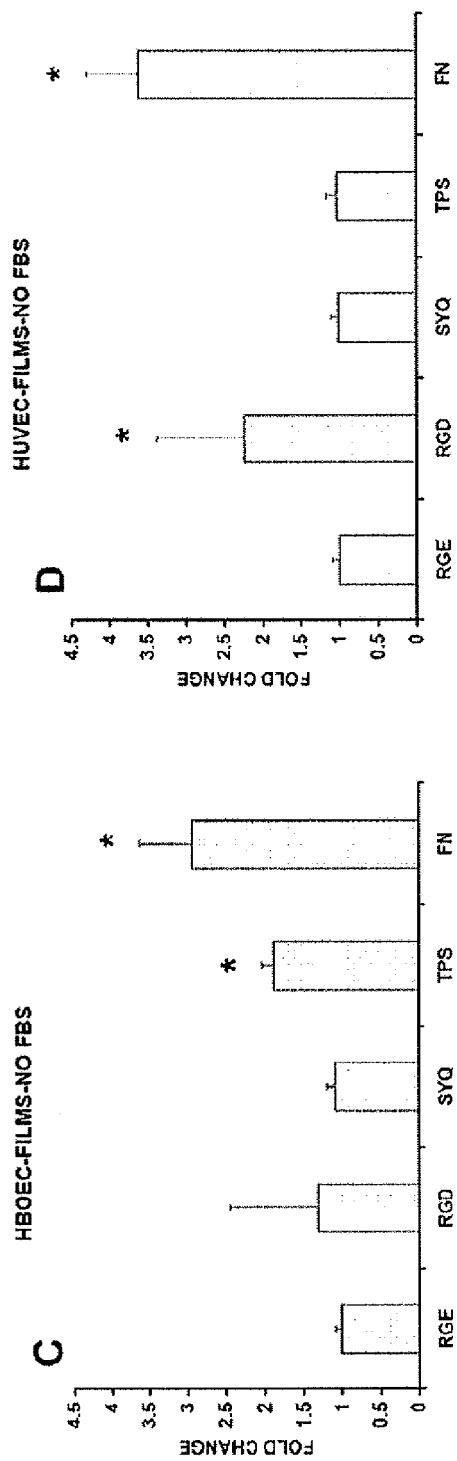

Phage display-selected peptide ligands were immobilized onto a methacrylic-based terpolymer matrix (FIG. 8A, B). Methacrylates were chosen because of their widespread usage in biomedical applications and their ease of synthesis via free radical polymerization reaction. Free radical polymerization chemistry also provides a unique option for attaching peptide sequences using a chain transfer reaction (Fussell 2004a and Fussell 2004b). Phage display-selected ligands were incorporated into methacrylic terpolymers using a C-terminal cysteine residue as a chain transfer agent. FIG. 8C shows a bar graph quantifying HBOEC attachment to peptide-modified materials after 2 hours of incubation in a serum-free endothelial growth medium (EGM-2 Single Quotes, Cambrex). Peptide concentrations used were similar; approximately 2 μmol peptide per gram of terpolymer as determined by amino acid analysis. An RGE-containing terpolymer was used as a negative control to which HBOEC attachment was normalized. Glass cover slips coated with fibronectin were used as positive controls. The cell adhesive RGD peptide was also included in the study. Panel D in FIG. 8 represents results of HUVEC binding to the various peptide-modified substrates. While HUVEC attachment to RGD and fibronectin substrates was statistically significant compared to RGE negative controls, HUVEC did not attach to HBOEC-specific, peptide-modified substrates. The results from FIGS. 8C and D collectively show that the phage display-selected TPS-peptide was able to specifically modulate HBOEC binding when immobilized to a prosthetic surface. Other peptide sequences selected from the library screen are characterized in a similar manner for cell-specific binding to peptides conjugated to biocompatible surfaces.

In Vivo Assay for Ligand Directed Endothelium Repair and Regeneration

Figure 9:
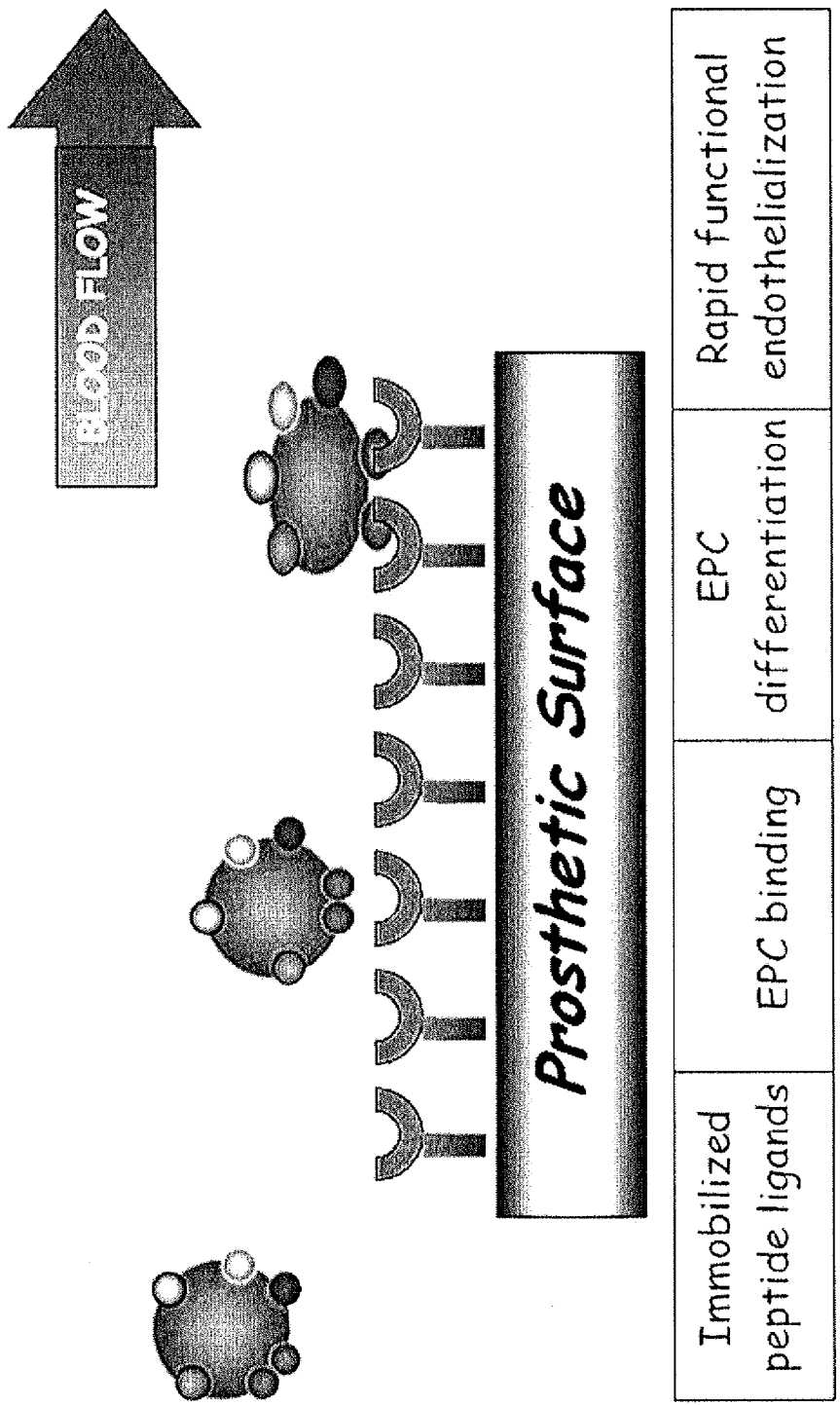
FIG. 9 is a schematic of the EPC capture technology for spontaneous endogenous endothelialization. The bioengineered prosthetic surface is a biocompatible terpolymer matrix with covalently-coupled, high-affinity peptide ligands that bind EPC from the circulation.
Figure 10:
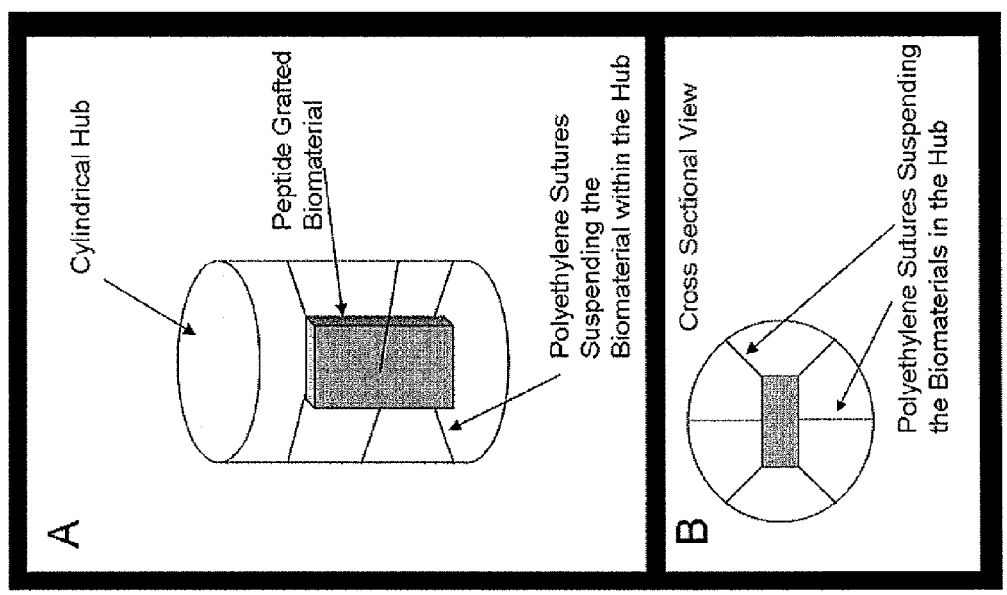
FIG. 10 is a schematic of the vascular construct for EPC capture in a porcine carotid artery model. A. Peptide-modified methacrylic terpolymer in the form of a rectangular sheet measuring 6.0 mm×6.0 mm×0.5 mm is suspended in the axis of a hollow cylindrical hub constructed of woven polyester, commercially-available vascular graft (length=2.5 cm, diameter=1 cm). This combination is held in mid-axial position by smooth polyethylene sutures anchoring the prosthesis and extending radially to the suspended biomaterial. B. Cross-sectional view.
Figure 11:
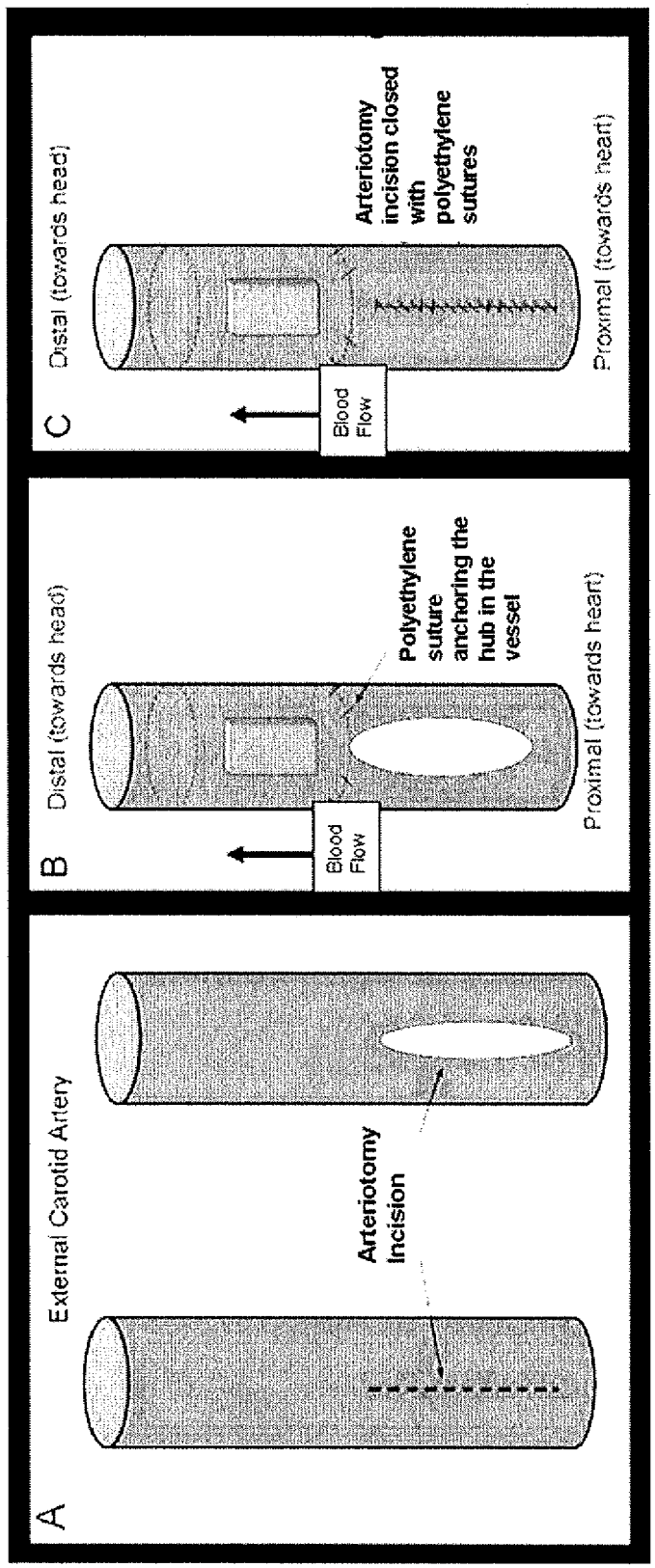
FIG. 11 is a schematic of the vascular surgery for EPC capture in a porcine carotid artery model. A. Longitudinal arteriotomy incision of the external carotid artery. B. The implant is inserted into the lumen of the external carotid artery distal to the arteriotomy incision. The prosthesis is fixed to the arterial wall with 6-0 polyethylene sutures in a simple continuous pattern, anchoring the edge of the cylindrical hub around the circumference of the arterial wall. C. The longitudinal arteriotomy incision is sutured with 6-0 polypropylene sutures in a continuous pattern.

In vivo experiments are useful for triaging clinically useful peptides that bind with high affinity and specificity to circulating endothelial progenitor cells. Thus, additional studies are directed to whether the bioactive peptide-based materials provide a microenvironment for efficient attachment of endothelial progenitor cells, and to their differentiation and formation of functional endothelial monolayer (schematically illustrated in FIG. 9). While not bound by any particular theory or mechanism, endothelial progenitor cells from the peripheral circulation may be recruited to bioactive scaffolds that are functionalized with endothelial progenitor cell-specific ligands and these recruited cells may significantly contribute to enhanced endothelialization. A porcine carotid artery model is utilized to study endothelialization of implants as detailed in FIGS. 10 and 11. This experimental design eliminates the possibility of endothelial cells migrating from adjacent tissues, ensuring that the cells adhering to the test surface are derived from the flowing blood.

Discussion

Phage display has proven to be a powerful strategy for the selection of peptides with desired binding properties (Hajitou et al. 2006; Rothe et al. 2006). The goal of the studies disclosed herein was to select peptide ligands that bind HBOEC with high affinity and specificity. The screening protocol resulted in the isolation of a panel of novel peptides and identification of several consensus motifs. Although no single peptide was sequenced from multiple clones, it has been previously shown that individual peptides isolated in this manner are efficient in binding their target in post phage display analysis (Cwirla et al. 1990; Koivunen et al. 1994). Small peptide motifs such as P(P/L)R, TP(T/S/G), PPS, and MPT appeared in these peptides. Although the overall significance of these peptides is unknown, the isolation of a number of peptides possessing identical motifs may be important in the binding of individual phage clones to the HBOEC surface. It has been suggested from other studies (Barry et al. 1996; Edelberg et al. 2004; Palmer et al. 1997; Szardenings et al. 1997) that peptides isolated from phage display often bind sites of protein-protein interaction raising the possibility that the HBOEC-binding peptides may target a functionally important binding site. A number of interesting homologies were identified (see Table 2), most notably interleukin-11 and ovarian cancer related tumor marker CA125 which may have implications for extending the understanding of HBOEC biology.

Phage selected through unbiased screens typically display specificity of 10-100 fold for the targeted cell type over other cell types (Oyama et al. 2006). The experiments disclosed herein confirm these observations. This finding is interesting when considering that the library was depleted only on HUVEC. While not bound by any particular theory or mechanism, this specificity suggests that the selected phage clones are not binding to a common receptor but may be targeting a less common receptor that is expressed on the target cell type.

TABLE 1

Peptide sequences identified by phage display. Potential consensus motifs are indicated with underlining. The primary consensus sequence, obtained by most commonly observed amino acid at each position, is presented in bold.

| PEPTIDE | SEQ ID NO: |
|---|---|
| HPAIVHISPQWA | 1 |
| QMVYG<u>PLR</u>STEQ | 2 |
| NSLTS<u>EPLR</u>YGG | 3 |
| APFAHSGPLAFS | 4 |
| TPLHPKSLMVWH | 5 |
| SNSMHLMTMTGL | 6 |
| SV<u>PPR</u>YTLTLQW | 7 |
| TLDWTKP<u>PLR</u>SG | 8 |
| ASQGYPEHRHAS | 9 |
| HKSYLPVPSLYG | 10 |
| QTTKLHIMDTGF | 11 |
| ISPAPHLLTSRF | 12 |

TABLE 1-continued

Peptide sequences identified by phage display. Potential consensus motifs are indicated with underlining. The primary consensus sequence, obtained by most commonly observed amino acid at each position, is presented in bold.

| PEPTIDE | SEQ ID NO: |
|---|---|
| HGTNQALSLLTP | 13 |
| VLNPQTTVMPPL | 14 |
| ATTSLTPTMANH | 15 |
| QATGPTTPTTSG | 16 |
| TPSLEQRTVYAK | 17 |
| LYSASTPPDPGG | 18 |
| FPMSSYKTYATP | 19 |
| INTPANRNPVLG | 20 |
| WDTNRNAASTPG | 21 |
| SYQTLKQHLPYG | 22 |
| HHVDSLPTLDWK | 23 |
| KLPHQPPSAAVH | 24 |
| SPWTSFLQWARG | 25 |
| QFPPKLTNNSML | 26 |
| YTDNSLGTSVGK | 27 |
| TSLRELPAEWSR | 28 |
| SHGKPPSRSPWT | 29 |
| YNLGQLEAQITS | 30 |
| ITLSATKGAAPS | 31 |
| SPPPSNAGSHHV | 32 |
| THPPNPSVSIGG | 33 |
| MPTSSTAPPPLI | 34 |
| ANYFSSPIKHAT | 35 |
| HPPHNMHLPAFS | 36 |
| MPTLTRAPHTAC | 37 |
| LPRKTPDYLQTR | 38 |
| SPTPS(P/L)PPSAGG | 39 |

TABLE 2

Identified sequence homologies. Table showing potentially relevant sequence homologies identified by BLAST. The underlined amino acids correspond to exact matches in peptide sequence.

| Peptide Sequence | Protein Accession |
|---|---|
| SV<u>PP</u>RYTLTLQW | Mucin glycoprotein (968-979) AAQ82434 |
| <u>HKSYLPVPSLYG</u> | Transmembrane protein 2 (41-47) CAI15172 |
| KL<u>PHQPPS</u>AAVH | T-cell specific adaptor protein (354-361) AAF69027 |
| TP<u>SLEQRTV</u>YAK | 2700029M09Rik protein - glycoprotein (202-208) AAH42740 |
| HH<u>VDSLPTLDWK</u> | Interleukin-11 (70-78) NP_000632 |
| HH<u>VDSLPTLDWK</u> | Ovarian cancer related tumor marker CA125 (3732-3739) AAL65133 |
| <u>MPTLTRAP</u>HTAC | Ovarian cancer related tumor marker CA125 (10670-10677) AAL65133 |
| S<u>PPPSNAG</u>SHHV | Voltage dependent calcium channel (2040-2049) CAI17142 |

The amino acid sequences represented the accession numbers can be found in SEQ ID NO:40-46, respectively.

REFERENCES

Altschul S F, Madden T L, Schaffer A A, Zhang J H, Zhang Z, Miller W, Lipman D J. 1997. Gapped BLAST and PSI-BLAST: a new generation of protein database search programs. Nucleic Acids Research 25(17):3389-3402.

Asahara T, Murohara T, Sullivan A, Silver M, vanderZee R, Li T, Witzenbichler B, Schatteman G, Isner J M. 1997. Isolation of putative progenitor endothelial cells for angiogenesis. Science 275(5302):964-967.

Ballard V L T, Holm J M, Edelberg J M. 2006a. A quantitative approach to phage display analysis for molecular profiling of vascular heterogeneity. Faseb Journal 20(4):A32-A32.

Ballard V L T, Holm J M, Edelberg J M. 2006b. Quantitative PCR-based approach for rapid phage display analysis: a foundation for high throughput vascular proteomic profiling. Physiological Genomics 26(3):202-208.

Barry M A, Dower W J, Johnston S A. 1996. Toward cell-targeting gene therapy vectors: Selection of cell-binding peptides from random peptide-presenting phage libraries. Nature Medicine 2(3):299-305.

Cwirla S E, Peters E A, Barrett R W, Dower W J. 1990. Peptides on Phage—a Vast Library of Peptides for Identifying Ligands. Proceedings of the National Academy of Sciences of the United States of America 87(16):6378-6382.

Edelberg J M, Wong A, Holm J M, Xaymardan M, Duignan I, Chin A, Kizer J R, Cai D Q. 2004. Phage display identification of age-associated TNF alpha-mediated cardiac oxidative induction. Physiological Genomics 18(3):255-260.

Fussell G. 2004a. Synthesis and characterization of acrylic terpolymers with RGD peptides for biomedical applications. Biomaterials. p 2971-2978.

Fussell G. 2004b. Endothelial cell adhesion on RGD-containing methacrylate terpolymers. Journal of biomedical materials research. p 265-273.

Gulati R, Jevremovic D, Peterson T E, Chatterjee S, Shah V, Vile R G, Simari R D. 2003a. Diverse origin and function of cells with endothelial phenotype obtained from adult human blood. Circulation Research 93(11):1023-1025.

Gulati R, Jevremovic D, Peterson T E, Witt T A, Kleppe L S, Mueske C S, Lerman A, Vile R G, Simari R D. 2003b. Autologous culture-modified mononuclear cells confer vascular protection after arterial injury. Circulation 108(12): 1520-1526.

Gulati R, Simari R D. 2004. Autologous cell-based therapies for vascular disease. Trends in Cardiovascular Medicine 14(7):262-267.

Hajitou A, Pasqualini R, Arap W. 2006. Vascular targeting: Recent advances and therapeutic perspectives. Trends in Cardiovascular Medicine 16(3):80-88.

Iwakura A, Luedemann C, Shastry S, Hanley A, Kearney M, Aikawa R, Isner J M, Asahara T, Losordo D W. 2003. Estrogen-mediated, endothelial nitric oxide synthase-dependent mobilization of bone marrow-derived endothelial progenitor cells contributes to reendothelialization after arterial injury. Circulation 108(25):3115-3121.

Koivunen E, Wang B C, Ruoslahti E. 1994. Isolation of a Highly Specific Ligand for the Alpha(5)Beta(1) Integrin from a Phage Display Library. Journal of Cell Biology 124(3):373-380.

Lin Y, Weisdorf D, Solovey A, Hebbel R P. 2000. Origins of circulating endothelial cells and endothelial outgrowth from blood. Journal of Clinical Investigation 105(1):71-77.

Oyama T, Rombel I T, Sarnli K N, Zhou X, Brown K C. 2006. Isolation of multiple cell-binding ligands from different phage displayed-peptide libraries. Biosensors & Bioelectronics 21(10):1867-1875.

Palmer D B, George A J T, Ritter M A. 1997. Selection of antibodies to cell surface determinants on mouse thymic epithelial cells using a phage display library. Immunology 91(3): 473-478.

Rehman J, Li J L, Orschell C M, March K L. 2003. Peripheral blood "endothelial progenitor cells" are derived from monocyte/macrophages and secrete angiogenic growth factors. Circulation 107(8):1164-1169.

Rothe A, Hosse R J, Power B E. 2006. In vitro display technologies reveal novel biopharmaceutics. Faseb Journal 20(10):1599-1610.

Smith G P. 1985. Filamentous Fusion Phage—Novel Expression Vectors That Display Cloned Antigens on the Virion Surface. Science 228(4705):1315-1317.

Smith G P, Petrenko V A. 1997. Phage display. Chemical Reviews 97(2):391-410.

Szardenings M, Tornroth S, Mutulis F, Muceniece R, Keinanen K, Kuusinen A, Wikberg J E S. 1997. Phage display selection on whole cells yields a peptide specific for melanocortin receptor 1. Journal of Biological Chemistry 272(44): 27943-27948.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

---

That which is claimed:

1. An isolated peptide that binds outgrowth endothelial cells (OEC) wherein said peptide comprises the amino acid sequence of SEQ ID NO:26 or a variant thereof, wherein said variant differs from SEQ ID NO:26 by one amino acid and wherein said variant binds OEC.

2. The peptide of claim 1, wherein said peptide has from about 11 to about 30 amino acids.

3. The peptide of claim 1, wherein said peptide contains at least one motif selected from the group consisting of PPR, TP, and PPS.

4. A method for sequestering and retaining outgrowth endothelial cells (OEC) at a therapeutic site of interest, said method comprising introducing at said therapeutic site at least one peptide wherein said peptide comprises the amino acid sequence of SEQ ID NO:26 or a variant thereof, wherein said variant differs from SEQ ID NO:26 by one amino acid and wherein said variant binds OEC.

5. The method of claim 4, wherein said peptide has from about 11 to about 30 amino acids.

6. The method of claim 4, wherein said peptide contains at least one motif selected from the group consisting of PPR, TP, and PPS.

7. The method of claim 4, wherein said peptide is bound to an outgrowth endothelial cell.

8. The method of claim 4, wherein said therapeutic site of interest is selected from the group consisting of an area where angiogenesis is desired, an area of ischemic injury, an area of organ transplantation, and an area of vascular injury.

9. A kit comprising at least one of the peptides of claim 1.

10. A composition comprising at least one peptide for use in a method for sequestering and retaining outgrowth endothelial cells (OEC) at a therapeutic site of interest, said method comprising introducing at said therapeutic site at least one peptide, wherein said peptide comprises the amino acid sequence of SEQ ID NO:26 or a variant thereof, wherein said variant differs from SEQ ID NO:26 by one amino acid and wherein said variant binds OEC.

11. The method composition of claim 10, wherein said peptide is bound to an OEC.

12. The composition of claim 10, wherein said therapeutic site of interest is selected from the group consisting of an area where angiogenesis is desired, an area of ischemic injury, an area of organ transplantation, and an area of vascular injury.

13. The peptide of claim 1, wherein said peptide is attached to an implant.

14. The peptide of claim 13, wherein said peptide is bound to an OEC.

15. An implant coated with at least one peptide, wherein said peptide comprises the amino acid sequence of SEQ ID NO:26 or a variant thereof, wherein said variant differs from SEQ ID NO:26 by one amino acid and wherein said variant binds outgrowth endothelial cells (OEC).

16. The implant of claim 15, wherein said peptide contains at least one motif selected from the group consisting of PPR, TP, and PPS.

17. The implant of claim 15, wherein said implant further comprises OEC bound to said peptide.

18. The implant of claim 15, wherein said peptide binds at least 10% more to OEC than a different cell type.

19. The implant of claim 15, wherein said peptide binds at least 50% more to OEC than a different cell type.

20. The implant of claim 15, wherein said peptide has from about 11 to about 30 amino acids.

21. The peptide of claim 1, wherein said peptide binds at least 10% more to OEC than a different cell type.

22. The peptide of claim 1, wherein said peptide binds at least 50% more to OEC than a different cell type.

23. The method of claim 4, wherein said peptide binds at least 10% more to OEC than a different cell type.

24. The method of claim 4, wherein said peptide binds at least 50% more to OEC than a different cell type.

25. The method of claim 4, wherein said peptide is attached to an implant.

26. The composition of claim 10, wherein said peptide binds at least 10% more to OEC than a different cell type.

27. The composition of claim 10, wherein said peptide binds at least 50% more to OEC than a different cell type.

28. The composition of claim 10, wherein said peptide has from about 11 to about 30 amino acids.

29. The composition of claim 10, wherein said peptide contains at least one motif selected from the group consisting of PPR, TP, and PPS.

30. A pharmaceutical composition comprising at least one peptide according to claim 1 and a pharmaceutically acceptable carrier.

* * * * *

UNITED STATES PATENT AND TRADEMARK OFFICE
CERTIFICATE OF CORRECTION

PATENT NO. : 8,426,367 B2  
APPLICATION NO. : 12/530137  
DATED : April 23, 2013  
INVENTOR(S) : Patterson et al.

Page 1 of 1

It is certified that error appears in the above-identified patent and that said Letters Patent is hereby corrected as shown below:

In the Claims

Column 176, line 51 (Claim 11), after "The" and before "composition" delete "method".

Signed and Sealed this
Sixteenth Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,426,367 B2                                        Page 1 of 1
APPLICATION NO. : 12/530137
DATED             : April 23, 2013
INVENTOR(S)       : Patterson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 761 days.

Signed and Sealed this
Eighth Day of September, 2015

Michelle K. Lee
*Director of the United States Patent and Trademark Office*